(12) United States Patent
Greenfield et al.

(10) Patent No.: US 11,066,682 B2
(45) Date of Patent: Jul. 20, 2021

(54) METHODS AND COMPOSITIONS FOR IMPROVED PRODUCTION OF FATTY ACIDS AND DERIVATIVES THEREOF

(75) Inventors: Derek L. Greenfield, South San Francisco, CA (US); Louis G. Hom, San Carlos, CA (US); Fernando A. Sanchez-Riera, South San Francisco, CA (US); Zhihao Hu, Castro Valley, CA (US); Vikranth Arlagadda, San Bruno, CA (US); Eli S. Groban, San Francisco, CA (US); Scott A. Frykman, San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 71 days.

(21) Appl. No.: 14/007,857

(22) PCT Filed: Apr. 2, 2012

(86) PCT No.: PCT/US2012/031881
§ 371 (c)(1),
(2), (4) Date: Jan. 22, 2014

(87) PCT Pub. No.: WO2012/154329
PCT Pub. Date: Nov. 15, 2012

(65) Prior Publication Data
US 2014/0179940 A1  Jun. 26, 2014

Related U.S. Application Data

(60) Provisional application No. 61/470,989, filed on Apr. 1, 2011.

(51) Int. Cl.
| | | |
|---|---|---|
| *C12P 7/62* | (2006.01) | |
| *C12P 7/64* | (2006.01) | |
| *C07K 14/245* | (2006.01) | |
| *C07K 14/195* | (2006.01) | |
| *C07C 31/125* | (2006.01) | |
| *C07C 33/02* | (2006.01) | |
| *C07C 53/126* | (2006.01) | |
| *A61K 38/00* | (2006.01) | |

(52) U.S. Cl.
CPC .......... *C12P 7/6409* (2013.01); *C07C 31/125* (2013.01); *C07C 33/02* (2013.01); *C07C 53/126* (2013.01); *C07K 14/195* (2013.01); *C07K 14/245* (2013.01); *Y02E 50/10* (2013.01)

(58) Field of Classification Search
CPC ..... C12P 7/62; C12N 2501/60; C07K 14/245; A61K 39/00152
See application file for complete search history.

(56) References Cited

U.S. PATENT DOCUMENTS

| | | |
|---|---|---|
| 5,000,000 A | 3/1991 | Ingram et al. |
| 5,028,539 A | 7/1991 | Ingram et al. |
| 5,424,202 A | 6/1995 | Ingram et al. |
| 5,482,846 A | 1/1996 | Ingram et al. |
| 5,602,030 A | 2/1997 | Ingrahm et al. |
| 5,891,686 A * | 4/1999 | Dennis ................. C07K 14/225 435/135 |
| 5,939,250 A | 8/1999 | Short |
| 5,965,408 A | 10/1999 | Short |
| 2009/0117629 A1* | 5/2009 | Schmidt-Dannert ........ C12N 9/1029 435/134 |
| 2009/0163699 A1* | 6/2009 | Chamberlain ..... C07K 16/2896 530/387.3 |
| 2010/0242345 A1 | 9/2010 | Keasling et al. |
| 2010/0251601 A1* | 10/2010 | Hu ........................... C10L 1/02 44/313 |
| 2011/0072871 A1* | 3/2011 | Chen .................... C05G 3/0023 71/23 |
| 2011/0117613 A1 | 5/2011 | Hoshino et al. |
| 2011/0229942 A1* | 9/2011 | Campbell ................ C12N 1/20 435/126 |
| 2011/0237769 A1* | 9/2011 | Feher ....................... C08F 2/00 526/337 |
| 2012/0232007 A1* | 9/2012 | Bobrowicz ........ C07K 14/4715 514/7.7 |

FOREIGN PATENT DOCUMENTS

| | | |
|---|---|---|
| EP | 2 768 966 | 8/2014 |
| WO | WO-03/038106 | 5/2003 |
| WO | WO-2008/100251 | 8/2008 |
| WO | WO-2008/119082 A2 | 10/2008 |
| WO | WO-2009/078973 A2 | 6/2009 |

(Continued)

OTHER PUBLICATIONS

DiRusso et al. (1998)Fatty Acyl-CoA Binding Domain of the Transcription Factor FadR, J. Biol. Chem., vol. 273, pp. 33652-33659.*

Emst et al. (2010) J.Visual. Exp., Linearization of the Bradford Protein Assay, pp. 1-6.*

Fox et al. (2001) Fatty acid synthesis in pea root plastids is inhibited by the action of long-chain acyl-coenzyme as on metabolite transporters, Palnt Physiol., vol. 126, No. 3, pp. 1259-1265.*

(Continued)

*Primary Examiner* — Scarlett Y Goon
*Assistant Examiner* — Samuel W Liu
(74) *Attorney, Agent, or Firm* — Harness Dickey & Pierce P.L.C.

(57) ABSTRACT

The invention relates to compositions and methods, including polynucleotide sequences, amino acid sequences, and engineered host cells for producing fatty acids and derivates of fatty acids such as acyl-CoA, terminal olefins, fatty aldehydes, fatty alcohols, alkanes, alkenes, wax esters, ketones and internal olefins through altered expression of the transcription factor, fadR.

21 Claims, 30 Drawing Sheets
Specification includes a Sequence Listing.

(56) References Cited

FOREIGN PATENT DOCUMENTS

| WO | WO-2010/042664 | 4/2010 |
| WO | WO-2010/062480 A2 | 6/2010 |

OTHER PUBLICATIONS

Zhang et al. (2002) The FabR (YijC) Transcription Factor Regulates Unsaturated Fatty Acid Biosynthesis in *Escherichia coli*, J. Biol. Chem, vol. 277. No. 18, pp. 15558-15565.*
Communication issued on EP Appl. 12719914.9, dated Jun. 23, 2016.
Altschul et al. "Basic Local Alignment Search Tool," (1990) J. Mol. Biol. 215(3):403-410.
Altschul et al. "Protein Database Searches Using Compositionally Adjusted Substitution Matrices," (2005) FEBS J. 272(20):5101-5109.
Amann et al, "Tightly regulated tac promoter vectors useful for the expression of unfused and fused proteins in *Escherichia coli*," Gene, 69: 301-315 (1988).
Arkin et al., "An algorithm for protein engineering: Simulations of recursive ensemble mutagenesis," Proc. Natl. Acad. Sci. U.S.A., vol. 89, pp. 7811-7815 (1992).
Arnold, "Protein engineering for unusual environments," Curr. Opin. Biotech., 4: 450-455 (1993).
Baldari et al., "A novel leader peptide which allows efficient secretion of a fragment of human interleukin 1 beta in *Saccharomyces cerevisiae*," EMBO J., vol. 6, No. 1, pp. 229-234 (1987).
Bowie et al., "Deciphering the Message in Protein Sequences: Tolerance to Amino Acid Substitutions," Science, vol. 247 pp. 1306-1310 (1990).
Caldwell et al, "Randomization of Genes by PCR Mutagenesis," PCR Methods Applic., 2: 28-33 (1992).
Camilli et al., "Bacterial Small-Molecule Signaling Pathways," Science 311 pp. 1113-1116 (2006).
Campbell et al., "A New *Escherichia coli* metabolic competency: growth on fatty acids by a novel anaerobic .beta.-oxidation pathway," Mol. Microbiol., 47(3): 793-805 (2003).
Caviglia et al., Rat Long Chain Acyl-CoA Synthetase 5, but Not 1, 2, 3, or 4, Complements *Escherichia coli* fadD*, The Journal of Biological Chemistry, 279(12): 1163-1169 (2004).
Cronan et al., "FadR, transcriptional co-ordination of metabolic expediency," Mol. Microbiol., 29(4): 937-943 (1998).
Currie, "Source Apportionment of Atmospheric Particles", Characterization of Environmental Particles, J. Buffle and H.P. van Leeuwen, Eds., vol. I of the IUPAC Environmental Analytical Chemistry Series, Lewis Publishers, Inc., pp. 3-74 (1992).
Datsenko et al., "One-step Inactivation of Chromosomal Genes in *Escherichia coli* K-12 using PCR Products," Proc. Natl. Acad. Sci. U.S.A., 97(12): 6640-6645 (2000).
Delagrave et al., "Searching Sequence Space to Engineer Proteins: Exponential Ensemble Mutagenesis," Biotech. Res, 11: 1548-1552 (1993).
He et al., "*Nocardia* sp. Carboxylic Acid Reductase: Cloning, Expresssion and Characterization of a New Aldehyde Oxidoreductase Family," Appl. Environ. Microbiol., 70(3): 874-1881 (2004).
Heath et al., "Lipid Biosynthesis as a Target for Antibacterial Agents," Prog. Lipid Res. 40(6): 467-97 (2001).
International Search Report for PCT/US2012/031881, dated Aug. 29, 2012.
Iram et al., "The beta-oxidation systems of *Escherichia coli* and *Salmonella enterica* are not functionally equivalent," Journal of Bacteriology, vol. 188, No. 2, Jan. 2006, pp. 599-608.
Kaufman et al., "Translational efficiency of polycistronic mRNAs and their utilization to express heterologous genes in mammalian cells," EMBO J., 6: 187-195 (1987).
Kurjan et al., Structure of a Yeast Pheromone Gene (MFx): A Putative x-Factor precursor Contains Four Tandem Copies of Mature x-Factor, Cell, vol. 30, pp. 933-943 (1982).
Leung et al. "A Journal of Methods in Cell and Molecular Biology," Technique vol. 1, No. 1, Aug. 1989 pp. 11-15.
Lucklow et al. "High Level Expression of Nonfused Foreign Genes with Autographa californica Nuclear Polyhedrosis Virus Expression Vectors," (1989) Virology 170, pp. 31-39.
Maniatis et al., "Regulation of Inducible and Tissue-Specific Gene Expression," Science, vol. 236, pp. 1237-1245 (1987).
McKenzie et al., "Fast, easy and efficient: site-specific insertion of transgenes into Enterobacterial chromosomes using Tn7 without need for selection of the insertion event," BMC Microbiology 6: 39 (2006), 7 pages.
Murli et al., J. Bacteriol., 182: 1127-1135 (2000).
Needleman and Wunsch, J. Mol. Biol., 48: 444-453 (1970).
Raman et al., "Analysis of acyl coenzyme a binding to the transcription factor FadR and identification of amino acid residues in the carboxyl terminus required for ligand binding," J. Biol. Chem., vol. 270, pp. 1092-1097 (1995).
Reading et al., FEMS Microbiol. Lett. 254:1-11 (2006).
Reidhaar-Olson et al., "Combinatorial Cassette Mutagenesis as a Probe of the Informational Content of Protein Sequences," Science, 241: 53-57 (1988).
Rosenberg Multiple Sequence Alignment Accuracy and Evolutionary Distance Estimation, (2005) BMC Bioinformatics 6, 10 pages.
Sambrook et al., "Molecular Cloning: A Laboratory Manual," second edition, Cold Spring Harbor Laboratory (1989), 31 pages.
Schultz et al. "Expression and secretion in yeast of a 400-kDa envelope glycoprotein derived from Epstein-Barr virus," (1987) Gene 54 pp. 113-123.
Seed, Nature, An LFA-3 cDNA encodes a phospholipid-linked membrane protein homologous to its receptor CD, Nature, vol. 329, pp. 840-842 (1987).
Shockey et al., "*Arabidopsis* Contains Nine Long-Chain Acyl-Coenzyme A Synthetase Genes that Participate in Fatty Acid and Glycerolipid Metabolism," Plant. Physiol., 29:1710-1722 (2002).
Smith et al., "Production of Human Beta Interferon in Insect Cells Infected with a Vaculovirus Expression Vector," Mol. Cell Biol., vol. 3, No. 12, 2156-2165 (1983).
Smith et al., Single-step purification of polypeptides expressed in *Escherichia coli* as fusions with glutathione S-transferase, Gene, 67, pp. 31-40 (1988).
Stemmer, "DNA shuffling by random fragmentation and reassembly: In vitro recombination for molecular evolution," Proc. Natl. Acad. Sci. U.S.A., vol. 91 pp. 10747-10751 (1994).
Studier et al., Gene Expression Technology: Methods in Enzymology 185, Academic Press, San Diego, CA, pp. 60-89 (1990).
Venturi, "Regulation of quorum sensing in Pseudomonas," FEMS Microbiol. Rev., 30: 274-291 (2006).
Communication issued on EP Application 12719914.9, dated May 28, 2018.
Extended European Search Report in EP Patent Application No. 20166326.7, dated May 26, 2020 (13 pages).
Fuzhong Zhang, et al., "Enhancing fatty acid production by the expression of the regulatory transcription factor FadR," Metabolic Engineering, Nov. 1, 2012, vol. 14, No. 6, pp. 653-660.
Examination Report issued on European Application 12719914.9, dated Mar. 16, 2017.

* cited by examiner

| CATEGORY | GENE | NAME | ACCESSION | EC NUMBER | USE | ORGANISM |
|---|---|---|---|---|---|---|
| Please note that dependent upon the purpose genes may be overexpressed, modified, attenuated or deleted | | | | | | |
| 1. Fatty Acid Production Increase / Product Production Increase. | | | | | | |
| increase acyl-ACP or acyl-CoA
reduce catabolism of derivatives and intermediates
reduce feedback inhibition
attenuate other pathways that consume fatty acids | | | | | | |
| | accA | Acetyl-CoA carboxylase, subunit A (carboxyltransferase alpha) | AAC73296, NP_414727 | 6.4.1.2 | Increase Malonyl-CoA production | Escherichia coli, Lactococci |
| | accB | Acetyl-CoA carboxylase, subunit B (BCCP: biotin carboxyl carrier) | NP_417721 | 6.4.1.2 | Increase Malonyl-CoA production | Escherichia coli, Lactococci |
| | accC | Acetyl-CoA carboxylase, subunit C (biotin carboxylase) | NP_417722 | 6.4.1.2, 6.3.4.14 | Increase Malonyl-CoA production | Escherichia coli, Lactococci |
| | accD | Acetyl-CoA carboxylase, subunit D (carboxyltransferase beta) | NP_416819 | 6.4.1.2 | Increase Malonyl-CoA production | Escherichia coli, Lactococci |
| | accDA1 (dtsR1) | Acetyl-CoA carboxylase, fused subunits D and A (carboxyltransferase) | YP_224991 | 6.4.1.2 | Increase Malonyl-CoA production | Corynebacterium glutamicum |
| | accBC | Acetyl-CoA carboxylase, fused subunits B and C (BCCP: biotin carboxyl carrier protein and biotin carboxylase) | YP_224999 | 6.4.1.2, 6.3.4.14 | Increase Malonyl-CoA production | Corynebacterium glutamicum |

FIG. 1A

| CATEGORY | GENE | NAME | ACCESSION | EC NUMBER | USE | ORGANISM |
|---|---|---|---|---|---|---|
| | acc1 | Acetyl-CoA carboxylase (carboxyltransferase, BCCP: biotin carboxyl carrier protein and biotin carboxylase) | NP_014413 | 6.4.1.2, 6.3.4.14 | Increase Malonyl-CoA production | Saccharomyces cerevisiae |
| | birA | biotin protein ligase | YP_225000 | 6.3.4.15 | Increase Malonyl-CoA production | Corynebacterium glutamicum |
| | bpl1 | biotin protein ligase | NP_010140 | 6.3.4.15 | Increase Malonyl-CoA production | Saccharomyces cerevisiae |
| | aceE | pyruvate dehydrogenase, subunit E1 | NP_414656, AAC73226 | 1.2.4.1 | Increase Acetyl-CoA production | Escherichia coli |
| | aceF | pyruvate dehydrogenase, subunit E2 | NP_414657 | 2.3.1.12 | Increase Acetyl-CoA production | Escherichia coli |
| | ackA | acetate kinase | AAC75356, NP_416799 | 2.7.2.1 | Increase Acetyl-CoA production | Escherichia coli |
| | ackB | acetate kinase AckB | BAB81430 | 2.7.2.1 | Increase Acetyl-CoA production | Escherichia coli |
| | acpP | acyl carrier protein | AAC74178 | NONE | Increase fatty acyl-ACP/CoA production | Escherichia coli |
| | fadD | acyl-CoA synthase | AP_002424 | 2.3.1.86, 6.2.1.3 | Increase Fatty acid production | Escherichia coli W3110 |
| | adhE | alcohol dehydrogenase | CAA47743 | 1.1.1.1, 1.2.1.10 | Increase Acetyl-CoA production | Escherichia coli W3111 |
| | fabA | beta-hydroxydecanoyl thioester dehydratase/isomerase | NP_415474 | 4.2.1.60 | Increase fatty acyl-ACP/CoA production | E. coli K12 |

FIG. 1B

| CATEGORY | GENE | NAME | ACCESSION | EC NUMBER | USE | ORGANISM |
|---|---|---|---|---|---|---|
| | fabB | 3-oxoacyl-[acyl-carrier-protein] synthase I | BAA16180 | EC:2.3.1.41 | increase fatty acyl-ACP/CoA production | Escherichia coli |
| | fabD | [acyl-carrier-protein] S-malonyltransferase | AAC74176 | 2.3.1.39 | increase fatty acyl-ACP/CoA production | E. coli K12 |
| | fabF | 3-oxoacyl-[acyl-carrier-protein] synthase II | AAC74179 | 2.3.1.179 | increase fatty acyl-ACP/CoA production | E. coli K12 |
| | fabG | 3-oxoacyl-[acyl-carrier protein] reductase | AAC74177 | 1.1.1.100 | increase fatty acyl-ACP/CoA production | E. coli K12 |
| | fabH | 3-oxoacyl-[acyl-carrier-protein] synthase III | AAC74175 | 2.3.1.180 | increase fatty acyl-ACP/CoA production | E. coli K12 |
| | fabI | enoyl-[acyl-carrier-protein] reductase | NP_415804 | 1.3.1.9 | increase fatty acyl-ACP/CoA production | E. coli K12 |
| | fabR | Transcriptional Repressor | NP_418398 | NONE | modulate unsaturated fatty acid production | E. coli K12 |
| | fabV | enoyl-[acyl-carrier-protein] reductase | YP_001217283 | 1.3.1.9 | increase fatty acyl-ACP/CoA production | Vibrio cholerae |
| | fabZ | (3R)-hydroxymyristol acyl carrier protein dehydratase | NP_414722 | 4.2.1.- | increase fatty acyl-ACP/CoA production | E. coli K12 |

FIG. 1C

| CATEGORY | GENE | NAME | ACCESSION | EC NUMBER | USE | ORGANISM |
|---|---|---|---|---|---|---|
| | fadE | acyl-CoA dehydrogenase | AAC73325 | 1.3.99.3, 1.3.99.- | reduce fatty acid degradation | E. coli K13 |
| | frdA | fumarate reductase | NP_418578 | 1.3.1.6 | increase Acetyl-CoA production | Escherichia coli |
| | GST, gshB | Glutathione synthase | P04425 | 6.3.2.3 | increase Acyl-CoA | E. coli K12 |
| | gpsA | biosynthetic sn-glycerol 3-phosphate dehydrogenase | AAC76632, NP_418065 | EC: 1.1.1.94 | increase Acetyl-CoA production | E. coli K12 |
| | ldhA | lactate dehydrogenase | AAC74462, NP_415898 | EC: 1.1.1.27, 1.1.1.28 | increase Acetyl-CoA production | E. coli K12 |
| | panD | aspartate 1-decarboxylase | BAB96708 | 4.1.1.11 | increase Acyl-CoA | Escherichia coli W3110 |
| | panK a.k.a. coaA | pantothenate kinase | AAC76952 | 2.7.1.33 | increase Acetyl-CoA production | E.coli |
| | panK a.k.a. coaA, R106K | pantothenate kinase | AAC76952 | 2.7.1.33 | increase Acetyl-CoA production | E. coli |
| | pdh | Pyruvate dehydrogenase | BAB34380, AAC73226, NP_415392 | 1.2.4.1 | increase Acetyl-CoA production | |
| | pflB | formate acetyltransferase (pyruvate formate lyase) | AAC73989, P09373 | EC: 2.3.1.54 | increase Acetyl-CoA production | |
| | plsB | acyltransferase | AAC77011 | 2.3.1.15 | reduce limits on Acyl-CoA pool | E. coli K12 |
| | poxB | pyruvate oxidase | AAC73958, NP_415392 | 1.2.2.2 | increase Acetyl-CoA production | |
| | pta | phosphotransacetylase | AAC75357, NP_416800 | 2.3.1.8 | increase Acetyl-CoA production | |

FIG. 1D

| CATEGORY | GENE | NAME | ACCESSION | EC NUMBER | USE | ORGANISM |
|---|---|---|---|---|---|---|
| | udhA | pyridine nucleotide transhydrogenase | CAA46822 | 1.6.1.1 | conversion NADH to NADPH or vice versa | E. coli |
| | atoB | acetyl-CoA acetyltransferase | NP_416728 | 2.3.1.9 | acetoacetyl-CoA synthesis | E. coli |
| | atoC | transcriptional regulatory protein | NP_416724 | NONE | acetoacetyl-CoA synthesis | E. coli |
| | yqeF | acetyl-CoA acetyltransferase | NP_417321 | 2.3.1.9 | acetoacetyl-CoA synthesis | E. coli |
| | fadB | fused 3-hydroxybutyryl-CoA epimerase/delta(3)-cis-delta(2)-trans-enoyl-CoA isomerase/enoyl-CoA hydratase and 3-hydroxyacyl-CoA dehydrogenase | AP_003956 | 4.2.1.17, 5.1.2.3, 5.3.3.8, 1.1.1.35 | Block or reverse fatty acid degradation | E. coli |
| | fadJ | 3-hydroxyacyl-CoA dehydrogenase; K01692 enoyl-CoA hydratase; K01782 3-hydroxybutyryl-CoA epimerase | AAC75401 | 1.1.1.35, 4.2.1.17, 5.1.2.3 | Block or reverse fatty acid degradation | E. coli |
| | fadA | 3-ketoacyl-CoA thiolase | BAE77458 | 2.3.1.16 | Block or reverse fatty acid degradation | E. coli |
| | fadI | beta-ketoacyl-CoA thiolase | AAC75402 | 2.3.1.16 | Block or reverse fatty acid degradation | E. coli |
| | fadR | transcriptional regulatory protein | NP_415705 | NONE | Block or reverse fatty acid degradation | E. coli |

FIG. 1E

| CATEGORY | GENE | NAME | ACCESSION | EC NUMBER | USE | ORGANISM |
|---|---|---|---|---|---|---|
| | ydiO | acyl-coA dehydrogenase | YP_852786 | 1.3.99.- | Block or reverse fatty acid degradation | E. coli |
| | ter | transenoyl-CoA reductase | Q5EU90 | 1.3.1.8 | reverse fatty acid biosynthesis | Euglena gracialis |
| 2. Structure Control | | | | | | |
| 2A. Chain Length Control | | | | | | |
| 2. | tesA | thioesterase | P0ADA1 | 3.1.2.-, 3.1.1.5 | C18 Chain Length | |
| | tesA without leader sequence | thioesterase | AAC73596, NP_415027 | 3.1.2.-, 3.1.1.5 | C18:1 | E. coli |
| | tesA without leader | thioesterase | P0ADA1 | 3.1.2.-, 3.1.1.5 | <C18 Chain Length | E. coli |
| | fatB1 (umbellularia) | thioesterase | Q41635 | 3.1.2.14 | C12:0 | Umbellularia californica |
| | fatB2 (umbellularia)D ELETE umbellularia) | thioesterase | AAC49269 | 3.1.2.14 | C8:0 - C10:0 | Cuphea hookeriana |
| | fatB3 | thioesterase | AAC72881 | 3.1.2.14 | C14:0 - C16:0 | Cuphea hookeriana |
| | fatB (cinnamonum) | thioesterase | Q39473 | 3.1.2.14 | C14:0 | Cinnamomum camphora |
| | fatB[M141T]* | thioesterase | CAA85388 | 3.1.2.14 | C16:1 | Arabidopsis thaliana |
| | fatA1 (Helianthus) | thioesterase | AAL79361 | 3.1.2.14 | C18:1 | Helianthus annuus |

FIG. 1F

| CATEGORY | GENE | NAME | ACCESSION | EC NUMBER | USE | ORGANISM |
|---|---|---|---|---|---|---|
| | atfata (ARABIDOPSIS FATA ACYL-ACP THIOESTERASE) | thioesterase | NP_189147, NP_193041 | 3.1.2.14 | C18:1 | Arabidopsis thaliana |
| | fatA | thioesterase | CAC39106 | 3.1.2.14 | C18:1 | Brassica juncea |
| | fatA (cuphea) | thioesterase | AAC72883 | 3.1.2.14 | C18:1 | Cuphea hockeriana |
| | tes | thioesterase | YP_130990 | 3.1.2.14 | | Photbacterium profundum |
| | tesB | thioesterase | NP_414986 | 3.1.2.14 | | E. coli |
| | fadM | thioesterase | NP_414977 | 3.1.2.14 | | E. coli |
| | yciA | thioesterase | NP_415769 | 3.1.2.14 | | E. coli |
| | ybgC | thioesterase | NP_415264 | 3.1.2.14 | | E. coli |
| 2B. Branching Control | | | | | | |
| | attenuate FabH | | | | increase branched chain fatty acid derivatives | |
| | express FabH from S. glaucescens or S. coelicolor and knock out endogenous FabH | | | | | |

FIG. 1G

| CATEGORY | GENE | NAME | ACCESSION | EC NUMBER | USE | ORGANISM |
|---|---|---|---|---|---|---|
| | express FabH from B. subtilis and knock out endogenous FabH | | | | | |
| | bfk - E3 - dihydrolipoyl dehydrogenase subunit | | | EC 1.2.4.4 | | |
| | bkd - E1 - alpha/beta subunit | decarboxylase subunits of branched-chain a-ketoacid dehydrogenase complex | | EC 1.2.4.4 | | |
| | bkd - E2 - dihydrolipoyl transacetylase subunit | | | EC 1.2.4.4 | | |
| | bkdA1 | branched-chain a-ketoacid dehydrogenase a-subunit (E1a) | NP_628006 | EC 1.2.4.4 | make branched-chain acyl-CoA precursors | Streptomyces coelicolor |
| | bkdB1 | branched-chain a-ketoacid dehydrogenase a-subunit (E1b) | NP_628005 | EC 1.2.4.4 | make branched-chain acyl-CoA precursors | Streptomyces coelicolor |
| | bkdC1 | dihydrolipoyl transacetylase (E2) | NP_628004 | EC 2.3.1.168 | make branched-chain acyl-CoA precursors | Streptomyces coelicolor |

FIG. 1H

| CATEGORY | GENE | NAME | ACCESSION | EC NUMBER | USE | ORGANISM |
|---|---|---|---|---|---|---|
| | bkdA2 | branched-chain a-ketoacid dehydrogenase a-subunit (E1a) | NP_733618 | EC 1.2.4.4 | make branched-chain acyl-CoA precursors | Streptomyces coelicolor |
| | bkdB2 | branched-chain a-ketoacid dehydrogenase b-subunit (E1b) | NP_628019 | EC 1.2.4.4 | make branched-chain acyl-CoA precursors | Streptomyces coelicolor |
| | bkdC2 | dihydrolipoyl transacetylase (E2) | NP_628018 | EC 2.3.1.168 | make branched-chain acyl-CoA precursors | Streptomyces coelicolor |
| | bkdA | branched-chain a-ketoacid dehydrogenase a-subunit (E1a) | BAC72074 | EC 1.2.4.4 | make branched-chain acyl-CoA precursors | Streptomyces avermitilis |
| | bkdB | branched-chain a-ketoacid dehydrogenase b-subunit (E1b) | BAC72075 | EC 1.2.4.4 | make branched-chain acyl-CoA precursors | Streptomyces avermitilis |
| | bkdC | dihydrolipoyl transacetylase (E2) | BAC72076 | EC 2.3.1.168 | make branched-chain acyl-CoA precursors | Streptomyces avermitilis |
| | bkdF | branched-chain a-ketoacid dehydrogenase a-subunit (E1a) | BAC72088 | EC 1.2.4.4 | make branched-chain acyl-CoA precursors | Streptomyces avermitilis |
| | bkdG | branched-chain a-ketoacid dehydrogenase b-subunit (E1b) | BAC72089 | EC 1.2.4.4 | make branched-chain acyl-CoA precursors | Streptomyces avermitilis |
| | bkdH | dihydrolipoyl transacetylase (E2) | BAC72090 | EC 2.3.1.168 | make branched-chain acyl-CoA precursors | Streptomyces avermitilis |

FIG. 11

| CATEGORY | GENE | NAME | ACCESSION | EC NUMBER | USE | ORGANISM |
|---|---|---|---|---|---|---|
| | bkdAA | branched-chain a-ketoacid dehydrogenase a-subunit (E1a) | NP_390285 | EC 1.2.4.4 | make branched-chain acyl-CoA precursors | Bacillus subtilis |
| | bkdAB | branched-chain a-ketoacid dehydrogenase b-subunit (E1b) | NP_390284 | EC 1.2.4.4 | make branched-chain acyl-CoA precursors | Bacillus subtilis |
| | bkdB | dihydrolipoyl transacetylase (E2) | NP_390283 | EC 2.3.1.168 | make branched-chain acyl-CoA precursors | Bacillus subtilis |
| | bkdA1 | branched-chain a-ketoacid dehydrogenase a-subunit (E1a) | AAA65614 | EC 1.2.4.4 | make branched-chain acyl-CoA precursors | Pseudomonas putida |
| | bkdA2 | branched-chain a-ketoacid dehydrogenase b-subunit (E1b) | AAA65615 | EC 1.2.4.4 | make branched-chain acyl-CoA precursors | Pseudomonas putida |
| | bkdC | dihydrolipoyl transacetylase (E2) | AAA65617 | EC 2.3.1.168 | make branched-chain acyl-CoA precursors | Pseudomonas putida |
| | lpd | dihydrolipoamide dehydrogenase (E3) | P09063 | 1.8.1.4 | make branched-chain acyl-CoA precursors | Pseudomonas putida |
| | lpd | dihydrolipoamide dehydrogenase (E3) | NP_414658 | 1.8.1.4 | make branched-chain acyl-CoA precursors | Escherichia coli |
| | ilvE | branched-chain amino acid aminotransferase | YP_026247 | 2.6.1.42 | make branched a-ketoacids | Escherichia coli |
| | ilvE | branched-chain amino acid aminotransferase | AAF34406 | 2.6.1.42 | make branched a-ketoacids | Lactococcus lactis |

FIG. 1J

| CATEGORY | GENE | NAME | ACCESSION | EC NUMBER | USE | ORGANISM |
|---|---|---|---|---|---|---|
| | ilvE | branched-chain amino acid aminotransferase | NP_746648 | 2.6.1.42 | make branched a-ketoacids | Pseudomonas putida |
| | ilvE | branched-chain amino acid aminotransferase | NP_629657 | 2.6.1.42 | make branched a-ketoacids | Streptomyces coelicolor |
| | ccr | crotonyl-CoA reductase | NP_630556 | 1.6.5.5,1.1.1.1 | Converting crotonyl-CoA to butyryl-CoA | Streptomyces coelicolor |
| | ccr | crotonyl-CoA reductase | AAD53915 | 1.6.5.5,1.1.1.1 | Converting crotonyl-CoA to butyryl-CoA | Streptomyces cinnamonensis |
| | IcmA, isobutyryl-CoA mutase | isobutyryl-CoA mutase, subunit A | NP_629554 | 5.4.99.2 | converting butyryl-CoA to isobutyryl-CoA | Streptomyces coelicolor |
| | IcmA, isobutyryl-CoA mutase | isobutyryl-CoA mutase, subunit A | AAC08713 | 5.4.99.2 | converting butyryl-CoA to isobutyryl-CoA | Streptomyces cinnamonensis |
| | IcmB, isobutyryl-CoA mutase | isobutyryl-CoA mutase, subunit B | NP_630904 | 5.4.99.2 | converting butyryl-CoA to isobutyryl-CoA | Streptomyces coelicolor |
| | IcmB, isobutyryl-CoA mutase | isobutyryl-CoA mutase, subunit B | CAB59633 | 5.4.99.2 | converting butyryl-CoA to isobutyryl-CoA | Streptomyces cinnamonensis |

FIG. 1K

| CATEGORY | GENE | NAME | ACCESSION | EC NUMBER | USE | ORGANISM |
|---|---|---|---|---|---|---|
| FabH, ACPs and fabF genes with specificity for branched chain acyl-CoAs | | | | | | |
| | IivE | branched-chain amino acid aminotransferase | CAC12788 | EC2.6.1.42 | branched chain amino acid amino transferase | Staphylococcus carnosus |
| | FabH1 | beta-ketoacyl-ACP synthase III | NP_626634 | 2.3.1.180 | initiation of branched-chain fatty acid biosynthesis | Streptomyces coelicolor |
| | FabH3 | beta-ketoacyl-ACP synthase III | NP_823466 | 2.3.1.180 | initiation of branched-chain fatty acid biosynthesis | Streptomyces avermitilis |
| | FabH_A | beta-ketoacyl-ACP synthase III | NP_389015 | 2.3.1.180 | initiation of branched-chain fatty acid biosynthesis | Bacillus subtilis |
| | FabH_B | beta-ketoacyl-ACP synthase III | NP_388898 | 2.3.1.180 | initiation of branched-chain fatty acid biosynthesis | Bacillus subtilis |

FIG. 1L

| CATEGORY | GENE | NAME | ACCESSION | EC NUMBER | USE | ORGANISM |
|---|---|---|---|---|---|---|
| | SmalDRAFT_08 18 | beta-ketoacyl-ACP synthase III | ZP_01643059 | 2.3.1.180 | Initiation of branched-chain fatty acid biosynthesis | Stenotrophomonas maltophilia |
| | FabH | beta-ketoacyl-ACP synthase III | YP_123672 | 2.3.1.180 | Initiation of branched-chain fatty acid biosynthesis | Legionella pneumophila |
| | FabH | beta-ketoacyl-ACP synthase III | NP_415609 | 2.3.1.180 | Initiation of branched-chain fatty acid biosynthesis | Escherichia coli |
| To Produce Cyclic Fatty Acids | | | | | | |
| | AnsJ | dehydratase (putative) | not available | not available | cyclohexylcarbonyl-CoA biosynthesis | Streptomyces collinus |
| | AnsK | CoA ligase (putative) | not available | not available | cyclohexylcarbonyl-CoA biosynthesis | Streptomyces collinus |
| | AnsL | dehydrogenase (putative) | not available | not available | cyclohexylcarbonyl-CoA biosynthesis | Streptomyces collinus |
| | ChcA | enoyl-CoA reductase | U72144 | EC 1.3.1.34 | cyclohexylcarbonyl-CoA biosynthesis | Streptomyces collinus |
| | AnsM | oxidoreductase (putative) | not available | not available | cyclohexylcarbonyl-CoA biosynthesis | Streptomyces collinus |

FIG. 1M

| CATEGORY | GENE | NAME | ACCESSION | EC NUMBER | USE | ORGANISM |
|---|---|---|---|---|---|---|
| | PlmJ | dehydratase (putative) | AAQ84158 | not available | cyclohexylcarbonyl-CoA biosynthesis | Streptomyces sp. HK803 |
| | PlmK | CoA ligase (putative) | AAQ84158 | not available | cyclohexylcarbonyl-CoA biosynthesis | Streptomyces sp. HK803 |
| | PlmL | dehydrogenase (putative) | AAQ84159 | not available | cyclohexylcarbonyl-CoA biosynthesis | Streptomyces sp. HK803 |
| | ChcA | enoyl-CoA reductase | AAQ84160 | EC 1.3.1.34 | cyclohexylcarbonyl-CoA biosynthesis | Streptomyces sp. HK803 |
| | PlmM | oxidoreductase (putative) | AAQ84161 | not available | cyclohexylcarbonyl-CoA biosynthesis | Streptomyces sp. HK803 |
| | ChcB | enoyl-CoA isomerase | AF268489 | not available | cyclohexylcarbonyl-CoA biosynthesis | Streptomyces collinus |
| | ChcB/CaiD | enoyl-CoA isomerase | NP_629292 | 4.2.1.- | cyclohexylcarbonyl-CoA biosynthesis | Streptomyces coelicolor |
| | ChcB/CaiD | enoyl-CoA isomerase | NP_824296 | 4.2.1.- | cyclohexylcarbonyl-CoA biosynthesis | Streptomyces avermitilis |

FIG. 1N

| CATEGORY | GENE | NAME | ACCESSION | EC NUMBER | USE | ORGANISM |
|---|---|---|---|---|---|---|
| 2C. Saturation Level Control | | | | | | |
| | Sfa | Suppressor of FabA | AAN79592, AAC44390 | NONE | increase monounsaturated fatty acids | E.coli |
| | also see FabA and FabB in sec. 1 | | | | produce unsaturated fatty acids | |
| | GnsA | suppressors of the secG null mutation | ABD18647.1 | NONE | increase unsaturated fatty acid esters | E.coli |
| | GnsB | suppressors of the secG null mutation | AAC74076.1 | NONE | increase unsaturated fatty acid esters | E.coli |
| | also see section 2A - items with 0 are unsaturated (no double bonds) and with :1 are saturated (1 double bond) | | | | | |
| | fabB | 3-oxoacyl-[acyl-carrier-protein] synthase I | BAA15180 | EC:2.3.1.41 | modulate unsaturated fatty acid production | Escherichia coli |

FIG. 10

| CATEGORY | GENE | NAME | ACCESSION | EC NUMBER | USE | ORGANISM |
|---|---|---|---|---|---|---|
| | fabK | trans-2-enoyl-ACP reductase II | AAF98273 | 1.3.1.9 | modulate unsaturated fatty acid production | Streptococcus pneumoniae |
| | fabL | enoyl-(acyl carrier protein) reductase | AAU39821 | 1.3.1.9 | modulate unsaturated fatty acid production | Bacillus licheniformis DSM 13 |
| | fabM | trans-2, cis-3-decenoyl-ACP isomerase | DAA05501 | 4.2.1.17 | modulate unsaturated fatty acid production | Streptococcus mutans |
| | des | D5 fatty acyl desaturase | O34653 | 1.14.19 | modulate unsaturated fatty acid production | Bacillus subtilis |
| 3. Final Product Output | | | | | | |
| 3A. Wax Output | | | | | | |
| | AT3G51970 | long-chain-alcohol O-fatty-acyltransferase | NP_190765 | 2.3.1.26 | wax production | Arabidopsis thaliana |
| | | thioesterase (see chain length control section) | | | increase fatty acid production | |
| | | fatty alcohol forming acyl-CoA reductase | | 1.1.1.* | convert acyl-coa to fatty alcohol | |
| | acr1 | acyl-CoA reductase (ACR1) | YP_047869 | 1.2.1.42 | convert acyl-coa to fatty alcohol | Acinetobacter sp. ADP1 |
| | yqhD | alcohol dehydrogenase | AP_003562 | 1.1.-.- | increase | E. coli W3110 |
| | ELO1 | Fatty acid elongase | BAD98251 | 2.3.1.- | produce very long chain length fatty acids | Pichia angusta |

FIG. 1P

| CATEGORY | GENE | NAME | ACCESSION | EC NUMBER | USE | ORGANISM |
|---|---|---|---|---|---|---|
| | plsC | acyltransferase | AAA16514 | 2.3.1.51 | | Saccharomyces cerevisiae |
| | DAGAT/DGAT | diacylglycerol acyltransferase | AAF19262 | 2.3.1.20 | wax production | Arabidopsis thaliana |
| | hWS | acyl-CoA wax alcohol acyltransferase | AAX48018 | 2.3.1.20 | wax production | Homo sapiens |
| | aft1 | bifunctional wax ester synthase/acyl-CoA:diacylglycerol acyltransferase | AAO17391 | 2.3.1.20 | wax production | Acinetobacter sp. ADP1 |
| | WS377 | wax ester synthase | ABO21021 | 2.3.1.20 | wax production | Marinobacter hydrocarbonoclasticus |
| | mWS | wax ester synthase (simmondsia) | AAD38041 | 2.3.1.- | wax production | Simmondsia chinensis |
| 3B. Fatty Alcohol Output | | | | | | |
| | | various thioesterases (refer to Sec. 2A) | | | hydrolyse fatty acyl-CoA/ACP | |
| | acr1 | acyl-CoA reductase | YP_047869 | 1.2.1.42 | reduce fatty acyl-CoA to fatty aldehydes | Acinetobacter sp. ADP1 |
| | yqhD | alcohol dehydrogenase | AP_003562 | 1.1.-.- | reduce fatty aldehydes to fatty alcohols | Escherichia coli W3110 |
| | alrA | alcohol dehydrogenase | CAG70252 | 1.1.-.- | reduce fatty aldehydes to fatty alcohols | Acinetobacter sp. ADP1 |

FIG. 1Q

| CATEGORY | GENE | NAME | ACCESSION | EC NUMBER | USE | ORGANISM |
|---|---|---|---|---|---|---|
| | BmFAR | FAR (fatty alcohol forming acyl-CoA reductase) | BAC79425 | 1.1.1.* | reduce fatty acyl-CoA to fatty alcohol | Bombyx mori |
| | GTNG_1865 | Long-chain aldehyde dehydrogenase | YP_001125970 | 1.2.1.3 | reduce fatty aldehydes to fatty alcohols | Geobacillus thermodenitrificans NG80-2 |
| | AAR | Acyl-ACP reductase | YP_400611 | 1.2.1.42 | reduce fatty acyl-ACP/CoA to fatty aldehydes | Synechococcus elongatus |
| | carB | Fatty acid reductase | YP_889972 | 6.2.1.3, 1.2.1.42 | reduce fatty acids to fatty aldehyde | Mycobacterium smegmatis |
| | FadD | acyl-CoA synthetase | NP_416319 | 6.2.1.3 | activates fatty acids to fatty acyl-CoAs | E. coli K12 |
| To make Butanol | | | | | | |
| | atoB | acetyl-CoA acetyltransferase | YP_049388 | 2.3.1.9 | produce | Erwinia carotovora |
| | hbd | Beta-hydroxybutyryl-CoA dehydrogenase | BAD51424 | 1.1.1.157 | produce | Butyrivibrio fibrisolvens |
| | CPE0095 | crotonase | BAB79801 | 4.2.1.55 | produce | Clostridium perfringens |
| | bcd | butyryl-CoA dehydrogenase | AAM14583 | 1.3.99.2 | produce | Clostridium beijerinckii |
| | ALDH | coenzyme A-acylating aldehyde dehydrogenase | AAT66436 | 1.2.1.3 | produce | Clostridium beijerinckii |
| | AdhE | aldehyde-alcohol dehydrogenase | AAN80172 | 1.1.1.1 1.2.1.10 | produce | Escherichia coli CFT073 |

3C. Fatty Alcohol Acetyl Ester Output

FIG. 1R

| CATEGORY | GENE | NAME | ACCESSION | EC NUMBER | USE | ORGANISM |
|---|---|---|---|---|---|---|
| | thioesterase | see chain length control section | | | produce | |
| | acr1 | acyl-CoA reductase | YP_047869 | 1.2.1.42 | produce | *Acinetobacter sp. ADP1* |
| | yqhD | alcohol dehydrogenase | AP_003562 | 1.1.-.- | produce | *E. Coli K12* |
| | AAT | alcohol O-acetyltransferase | AAG13130 | 2.3.1.84 | produce | *Fragaria x ananassa* |
| | | | | | | |
| 4. Export | | | | | | |
| | AtMRP5 | Arabidopsis thaliana multidrug resistance-associated | NP_171908 | NONE | export products | *Arabidopsis thaliana* |
| | AmiS2 | ABC transporter AmiS2 | JC5491 | NONE | export products | *Rhodococcus sp.* |
| | AtPGP1 | ARABIDOPSIS THALIANA P GLYCOPROTEIN1 | NP_181228 | NONE | export products | *Arabidopsis thaliana* |
| | AcrA | putative multidrug-efflux transport protein acrA | CAF23274 | NONE | export products | *Candidatus Protochlamydia amoebophila UWE25* |
| | AcrB | probable multidrug-efflux transport protein, acrB | CAF23275 | NONE | export products | *Candidatus Protochlamydia amoebophila UWE25* |
| | TolC | Outer membrane protein [Cell envelope biogenesis, | ABD59001 | NONE | export products | *Francisella tularensis subsp. novicida* |
| | AcrE | transmembrane protein affects septum formation and cell membrane permeability | YP_312213 | NONE | export products | *Shigella sonnei Ss046* |
| | AcrF | Acriflavine resistance protein F | P24181 | NONE | export products | *Escherichia coli* |
| | tll1619 | multidrug efflux transporter | NP_682409.1 | NONE | export products | *Thermosynechococcus elongatus BP-1]* |
| | tll0139 | multidrug efflux transporter | NP_680930.1 | NONE | export products | *Thermosynechococcus elongatus BP-1]* |

FIG. 1S

| CATEGORY | GENE | NAME | ACCESSION | EC NUMBER | USE | ORGANISM |
|---|---|---|---|---|---|---|
| 5. Fermentation | | | | | | |
| | replication checkpoint genes | | | | increase output efficiency | |
| | umuD | DNA polymerase V, subunit | YP_310132 | 3.4.21.- | increase output efficiency | *Shigella sonnei Ss046* |
| | umuC | DNA polymerase V, subunit | ABC42261 | 2.7.7.7 | increase output efficiency | *Escherichia coli* |
| | NADH:NADPH transhydrogenase (alpha and beta subunits) (pntA, pntB) | | P07001, P0AB70 | 1.6.1.2 | increase output efficiency | *Shigella flexneri* |

FIG. 1T

SEQUENCE LISTING

```
<160> NUMBER OF SEQ ID NOS: 23

<210> SEQ ID NO 1
<211> LENGTH: 239
<212> TYPE: PRT
<213> ORGANISM: Escherichia coli

<400> SEQUENCE: 1

Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
    50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95

Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
            180                 185                 190

Tyr His Lys Leu Ser Ala Leu Cys Ser Glu Gly Ala His Asp Gln Val
        195                 200                 205

Tyr Glu Thr Val Arg Arg Tyr Gly His Glu Ser Gly Glu Ile Trp His
    210                 215                 220

Arg Met Gln Lys Asn Leu Pro Gly Asp Leu Ala Ile Gln Gly Arg
```

<210> SEQ ID NO 2
<211> LENGTH: 473
<212> TYPE: PRT
<213> ORGANISM: Marinobacter hydrocarbonoclasticus

<400> SEQUENCE: 2

Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

```
Leu Gln Leu Met Ser Gly Leu Gly Gly Arg Met Arg Pro Val Phe Asn
    370             375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
            405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
            435                 440                 445

Val Tyr Thr Gly Glu Ala Leu Asp Glu Leu Glu Ser Leu Ile Leu Pro
450                 455                 460

Pro Lys Lys Arg Ala Arg Thr Arg Lys
465                 470

<210> SEQ ID NO 3
<211> LENGTH: 455
<212> TYPE: PRT
<213> ORGANISM: Marinobacter hydrocarbonoclasticus

<400> SEQUENCE: 3

Met Thr Pro Leu Asn Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45

Gln Lys Thr Glu Val Thr Ala Pro Phe Asn Gln Arg Leu Ser Tyr Arg
50                  55                  60

Leu Gly Gln Pro Val Trp Val Glu Asp Glu His Leu Asp Leu Glu His
65                  70                  75                  80

His Phe Arg Phe Glu Ala Leu Pro Thr Pro Gly Arg Ile Arg Glu Leu
                85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125

Ala Leu Tyr Thr Lys Val His His Ser Leu Val Asp Gly Val Ser Ala
130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Asp Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
                245                 250                 255

Ala Tyr Gly Thr Thr Val Asn Asp Val Val Thr Ala Met Cys Ala Ala
            260                 265                 270
```

Ala Leu Arg Thr Tyr Leu Met Asn Gln Asp Ala Leu Pro Glu Lys Pro
            275                 280                 285

Leu Val Ala Phe Val Pro Val Ser Leu Arg Arg Asp Asp Ser Ser Gly
        290                 295                 300

Gly Asn Gln Val Gly Val Ile Leu Ala Ser Leu His Thr Asp Val Gln
305                 310                 315                 320

Asp Ala Gly Glu Arg Leu Leu Lys Ile His His Gly Met Glu Ala
                325                 330                 335

Lys Gln Arg Tyr Arg His Met Ser Pro Glu Glu Ile Val Asn Tyr Thr
                340                 345                 350

Ala Leu Thr Leu Ala Pro Ala Ala Phe His Leu Leu Thr Gly Leu Ala
            355                 360                 365

Pro Lys Trp Gln Thr Phe Asn Val Val Ile Ser Asn Val Pro Gly Pro
        370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
                420                 425                 430

Pro Ser Leu Gln Arg Met Leu Asp Tyr Leu Glu Gln Gly Leu Ala Glu
            435                 440                 445

Leu Glu Leu Asn Ala Gly Leu
        450                 455

<210> SEQ ID NO 4
<211> LENGTH: 457
<212> TYPE: PRT
<213> ORGANISM: Alcanivorax borkumensis

<400> SEQUENCE: 4

Met Lys Ala Leu Ser Pro Val Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Gly Pro Lys Tyr Val Ser Glu Leu Ala Gln Gln Met Arg
        35                  40                  45

Asp Tyr Cys His Pro Val Ala Pro Phe Asn Gln Arg Leu Thr Arg Arg
    50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu
                85                  90                  95

Leu Ser Leu Val Ser Ala Glu His Ser Asn Leu Leu Asp Arg Glu Arg
            100                 105                 110

Pro Met Trp Glu Ala His Leu Ile Glu Gly Ile Arg Gly Arg Gln Phe
        115                 120                 125

Ala Leu Tyr Tyr Lys Ile His His Ser Val Met Asp Gly Ile Ser Ala
    130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala

```
            180                 185                 190
Ser Ile Ser Lys Gln Ala Ala Thr Val Pro Gly Leu Ala Arg Glu Val
        195                 200                 205
Tyr Lys Val Thr Gln Lys Ala Lys Lys Asp Glu Asn Tyr Val Ser Ile
    210                 215                 220
Phe Gln Ala Pro Asp Thr Ile Leu Asn Asn Thr Ile Thr Gly Ser Arg
225                 230                 235                 240
Arg Phe Ala Ala Gln Ser Phe Pro Leu Pro Arg Leu Lys Val Ile Ala
                245                 250                 255
Lys Ala Tyr Asn Cys Thr Ile Asn Thr Val Val Leu Ser Met Cys Gly
            260                 265                 270
His Ala Leu Arg Glu Tyr Leu Ile Ser Gln His Ala Leu Pro Asp Glu
        275                 280                 285
Pro Leu Ile Ala Met Val Pro Met Ser Leu Arg Gln Asp Asp Ser Thr
    290                 295                 300
Gly Gly Asn Gln Ile Gly Met Ile Leu Ala Asn Leu Gly Thr His Ile
305                 310                 315                 320
Cys Asp Pro Ala Asn Arg Leu Arg Val Ile His Asp Ser Val Glu Glu
                325                 330                 335
Ala Lys Ser Arg Phe Ser Gln Met Ser Pro Glu Ile Leu Asn Phe
            340                 345                 350
Thr Ala Leu Thr Met Ala Pro Thr Gly Leu Asn Leu Thr Gly Leu
        355                 360                 365
Ala Pro Lys Trp Arg Ala Phe Asn Val Val Ile Ser Asn Ile Pro Gly
    370                 375                 380
Pro Lys Glu Pro Leu Tyr Trp Asn Gly Ala Gln Leu Gln Gly Val Tyr
385                 390                 395                 400
Pro Val Ser Ile Ala Leu Asp Arg Ile Ala Leu Asn Ile Thr Leu Thr
                405                 410                 415
Ser Tyr Val Asp Gln Met Glu Phe Gly Leu Ile Ala Cys Arg Arg Thr
            420                 425                 430
Leu Pro Ser Met Gln Arg Leu Leu Asp Tyr Leu Glu Gln Ser Ile Arg
        435                 440                 445
Glu Leu Glu Ile Gly Ala Gly Ile Lys
    450                 455

<210> SEQ ID NO 5
<211> LENGTH: 451
<212> TYPE: PRT
<213> ORGANISM: Alcanivorax borkumensis

<400> SEQUENCE: 5

Met Ala Arg Lys Leu Ser Ile Met Asp Ser Gly Trp Leu Met Met Glu
1               5                   10                  15
Thr Arg Glu Thr Pro Met His Val Gly Gly Leu Ala Leu Phe Ala Ile
            20                  25                  30
Pro Glu Gly Ala Pro Glu Asp Tyr Val Glu Ser Ile Tyr Arg Tyr Leu
        35                  40                  45
Val Asp Val Asp Ser Ile Cys Arg Pro Phe Asn Gln Lys Ile Gln Ser
    50                  55                  60
His Leu Pro Leu Tyr Leu Asp Ala Thr Trp Val Glu Asp Lys Asn Phe
65                  70                  75                  80
Asp Ile Asp Tyr His Val Arg His Ser Ala Leu Pro Arg Pro Gly Arg
                85                  90                  95
```

Val Arg Glu Leu Leu Ala Leu Val Ser Arg Leu His Ala Gln Arg Leu
            100                 105                 110

Asp Pro Ser Arg Pro Leu Trp Glu Ser Tyr Leu Ile Glu Gly Leu Glu
        115                 120                 125

Gly Asn Arg Phe Ala Leu Tyr Thr Lys Met His His Ser Met Val Asp
    130                 135                 140

Gly Val Ala Gly Met His Leu Met Gln Ser Arg Leu Ala Thr Cys Ala
145                 150                 155                 160

Glu Asp Arg Leu Pro Ala Pro Trp Ser Gly Trp Asp Ala Glu Lys
                165                 170                 175

Lys Pro Arg Lys Ser Arg Gly Ala Ala Ala Asn Ala Gly Met Lys
            180                 185                 190

Gly Thr Met Asn Asn Leu Arg Arg Gly Gly Gln Leu Val Asp Leu
        195                 200                 205

Leu Arg Gln Pro Lys Asp Gly Asn Val Lys Thr Ile Tyr Arg Ala Pro
    210                 215                 220

Lys Thr Gln Leu Asn Arg Arg Val Thr Gly Ala Arg Arg Phe Ala Ala
225                 230                 235                 240

Gln Ser Trp Ser Leu Ser Arg Ile Lys Ala Ala Gly Lys Gln His Gly
                245                 250                 255

Gly Thr Val Asn Asp Ile Phe Leu Ala Met Cys Gly Gly Ala Leu Arg
            260                 265                 270

Arg Tyr Leu Leu Ser Gln Asp Ala Leu Ser Asp Gln Pro Leu Val Ala
        275                 280                 285

Gln Val Pro Val Ala Leu Arg Ser Ala Asp Gln Ala Gly Glu Gly Gly
    290                 295                 300

Asn Ala Ile Thr Thr Val Gln Val Ser Leu Gly Thr His Ile Ala Gln
305                 310                 315                 320

Pro Leu Asn Arg Leu Ala Ala Ile Gln Asp Ser Met Lys Ala Val Lys
                325                 330                 335

Ser Arg Leu Gly Asp Met Gln Lys Ser Glu Ile Asp Val Tyr Thr Val
            340                 345                 350

Leu Thr Asn Met Pro Leu Ser Leu Gly Gln Val Thr Gly Leu Ser Gly
        355                 360                 365

Arg Val Ser Pro Met Phe Asn Leu Val Ile Ser Asn Val Pro Gly Pro
    370                 375                 380

Lys Glu Thr Leu His Leu Asn Gly Ala Glu Met Leu Ala Thr Tyr Pro
385                 390                 395                 400

Val Ser Leu Val Leu His Gly Tyr Ala Leu Asn Ile Thr Val Val Ser
                405                 410                 415

Tyr Lys Asn Ser Leu Glu Phe Gly Val Ile Gly Cys Arg Asp Thr Leu
            420                 425                 430

Pro His Ile Gln Arg Phe Leu Val Tyr Leu Glu Glu Ser Leu Val Glu
        435                 440                 445

Leu Glu Pro
    450

<210> SEQ ID NO 6
<211> LENGTH: 455
<212> TYPE: PRT
<213> ORGANISM: Marinobacter aquaeolei

<400> SEQUENCE: 6

Met Thr Pro Leu Asn Pro Thr Asp Gln Leu Phe Leu Trp Leu Glu Lys
1               5                   10                  15

```
Arg Gln Gln Pro Met His Val Gly Gly Leu Gln Leu Phe Ser Phe Pro
             20                  25                  30

Glu Gly Ala Pro Asp Asp Tyr Val Ala Gln Leu Ala Asp Gln Leu Arg
         35                  40                  45

Gln Lys Thr Glu Val Thr Ala Pro Phe Asn Gln Arg Leu Ser Tyr Arg
     50                  55                  60

Leu Gly Gln Pro Val Trp Val Glu Asp Glu His Leu Asp Leu Glu His
 65                  70                  75                  80

His Phe Arg Phe Glu Ala Leu Pro Thr Pro Gly Arg Ile Arg Glu Leu
                 85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125

Ala Leu Tyr Thr Lys Val His His Ser Leu Val Asp Gly Val Ser Ala
    130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Gly Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
    210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
                245                 250                 255

Ala Tyr Gly Thr Thr Val Asn Asp Val Val Thr Ala Met Cys Ala Ala
            260                 265                 270

Ala Leu Arg Thr Tyr Leu Met Asn Gln Asp Ala Leu Pro Glu Lys Pro
        275                 280                 285

Leu Val Ala Phe Val Pro Val Ser Leu Arg Arg Asp Asp Ser Ser Gly
    290                 295                 300

Gly Asn Gln Val Gly Val Ile Leu Ala Ser Leu His Thr Asp Val Gln
305                 310                 315                 320

Glu Ala Gly Glu Arg Leu Leu Lys Ile His His Gly Met Glu Glu Ala
                325                 330                 335

Lys Gln Arg Tyr Arg His Met Ser Pro Glu Glu Ile Val Asn Tyr Thr
            340                 345                 350

Ala Leu Thr Leu Ala Pro Ala Ala Phe His Leu Leu Thr Gly Leu Ala
        355                 360                 365

Pro Lys Trp Gln Thr Phe Asn Val Val Ile Ser Asn Val Pro Gly Pro
    370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
            420                 425                 430
```

Pro Ser Leu Gln Arg Met Leu Asp Tyr Leu Glu Gln Gly Leu Ala Glu
            435                 440                 445

Leu Glu Leu Asn Ala Gly Leu
    450                 455

<210> SEQ ID NO 7
<211> LENGTH: 473
<212> TYPE: PRT
<213> ORGANISM: Marinobacter aquaeolei

<400> SEQUENCE: 7

Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45

Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

```
Lys Ser Ala Leu Thr Gln Tyr Thr Met Leu Met Ser Pro Tyr Ile
            355                 360                 365

Leu Gln Leu Met Ser Gly Leu Gly Gly Arg Met Arg Pro Val Phe Asn
370                 375                 380

Val Thr Ile Ser Asn Val Pro Gly Pro Glu Asp Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
                420                 425                 430

Gly Phe Thr Gly Cys Arg Asp Thr Leu Pro Ser Met Gln Lys Leu Ala
                435                 440                 445

Val Tyr Thr Gly Glu Ala Leu Asp Glu Leu Glu Ser Leu Ile Leu Pro
            450                 455                 460

Pro Lys Lys Arg Ala Arg Thr Arg Lys
465                 470

<210> SEQ ID NO 8
<211> LENGTH: 1173
<212> TYPE: PRT
<213> ORGANISM: Mycobacterium smegmatis

<400> SEQUENCE: 8

Met Thr Ser Asp Val His Asp Ala Thr Asp Gly Val Thr Glu Thr Ala
1               5                   10                  15

Leu Asp Asp Glu Gln Ser Thr Arg Ile Ala Glu Leu Tyr Ala Thr
            20                  25                  30

Asp Pro Glu Phe Ala Ala Ala Pro Leu Pro Ala Val Val Asp Ala
                35                  40                  45

Ala His Lys Pro Gly Leu Arg Leu Ala Glu Ile Leu Gln Thr Leu Phe
        50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
```

```
                245                 250                 255
Leu Ala Met Ile Leu Tyr Thr Ser Gly Ser Thr Gly Ala Pro Lys Gly
            260                 265                 270
Ala Met Tyr Thr Glu Ala Met Val Ala Arg Leu Trp Thr Met Ser Phe
            275                 280                 285
Ile Thr Gly Asp Pro Thr Pro Val Ile Asn Val Asn Phe Met Pro Leu
            290                 295                 300
Asn His Leu Gly Gly Arg Ile Pro Ile Ser Thr Ala Val Gln Asn Gly
305                 310                 315                 320
Gly Thr Ser Tyr Phe Val Pro Glu Ser Asp Met Ser Thr Leu Phe Glu
                325                 330                 335
Asp Leu Ala Leu Val Arg Pro Thr Glu Leu Gly Leu Val Pro Arg Val
            340                 345                 350
Ala Asp Met Leu Tyr Gln His His Leu Ala Thr Val Asp Arg Leu Val
            355                 360                 365
Thr Gln Gly Ala Asp Glu Leu Thr Ala Glu Lys Gln Ala Gly Ala Glu
        370                 375                 380
Leu Arg Glu Gln Val Leu Gly Gly Arg Val Ile Thr Gly Phe Val Ser
385                 390                 395                 400
Thr Ala Pro Leu Ala Ala Glu Met Arg Ala Phe Leu Asp Ile Thr Leu
                405                 410                 415
Gly Ala His Ile Val Asp Gly Tyr Gly Leu Thr Glu Thr Gly Ala Val
            420                 425                 430
Thr Arg Asp Gly Val Ile Val Arg Pro Pro Val Ile Asp Tyr Lys Leu
            435                 440                 445
Ile Asp Val Pro Glu Leu Gly Tyr Phe Ser Thr Asp Lys Pro Tyr Pro
        450                 455                 460
Arg Gly Glu Leu Leu Val Arg Ser Gln Thr Leu Thr Pro Gly Tyr Tyr
465                 470                 475                 480
Lys Arg Pro Glu Val Thr Ala Ser Val Phe Asp Arg Asp Gly Tyr Tyr
                485                 490                 495
His Thr Gly Asp Val Met Ala Glu Thr Ala Pro Asp His Leu Val Tyr
            500                 505                 510
Val Asp Arg Arg Asn Asn Val Leu Lys Leu Ala Gln Gly Glu Phe Val
        515                 520                 525
Ala Val Ala Asn Leu Glu Ala Val Phe Ser Gly Ala Ala Leu Val Arg
        530                 535                 540
Gln Ile Phe Val Tyr Gly Asn Ser Glu Arg Ser Phe Leu Leu Ala Val
545                 550                 555                 560
Val Val Pro Thr Pro Glu Ala Leu Glu Gln Tyr Asp Pro Ala Ala Leu
                565                 570                 575
Lys Ala Ala Leu Ala Asp Ser Leu Gln Arg Thr Ala Arg Asp Ala Glu
            580                 585                 590
Leu Gln Ser Tyr Glu Val Pro Ala Asp Phe Ile Val Glu Thr Glu Pro
        595                 600                 605
Phe Ser Ala Ala Asn Gly Leu Leu Ser Gly Val Gly Lys Leu Leu Arg
    610                 615                 620
Pro Asn Leu Lys Asp Arg Tyr Gly Gln Arg Leu Glu Gln Met Tyr Ala
625                 630                 635                 640
Asp Ile Ala Ala Thr Gln Ala Asn Gln Leu Arg Glu Leu Arg Arg Ala
                645                 650                 655
Ala Ala Thr Gln Pro Val Ile Asp Thr Leu Thr Gln Ala Ala Ala Thr
            660                 665                 670
```

```
Ile Leu Gly Thr Gly Ser Glu Val Ala Ser Asp Ala His Phe Thr Asp
            675                 680                 685

Leu Gly Gly Asp Ser Leu Ser Ala Leu Thr Leu Ser Asn Leu Leu Ser
        690                 695                 700

Asp Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
            755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
            835                 840                 845

Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
            915                 920                 925

Ala Met Gly Ile Pro Asp Phe Glu Glu Asp Gly Asp Ile Arg Thr Val
        930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
            965                 970                 975

Gly Leu Pro Val Ala Thr Phe Arg Ser Asp Met Ile Leu Ala His Pro
        980                 985                 990

Arg Tyr Arg Gly Gln Val Asn Val Pro Asp Met Phe Thr Arg Leu Leu
        995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080
```

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 9
<211> LENGTH: 341
<212> TYPE: PRT
<213> ORGANISM: Acinetobacter baylyi

<400> SEQUENCE: 9

Met Ala Thr Thr Asn Val Ile His Ala Tyr Ala Ala Met Gln Ala Gly
1               5                   10                  15

Glu Ala Leu Val Pro Tyr Ser Phe Asp Ala Gly Glu Leu Gln Pro His
                20                  25                  30

Gln Val Glu Val Lys Val Glu Tyr Cys Gly Leu Cys His Ser Asp Val
            35                  40                  45

Ser Val Leu Asn Asn Glu Trp His Ser Ser Val Tyr Pro Val Val Ala
        50                  55                  60

Gly His Glu Val Ile Gly Thr Ile Thr Gln Leu Gly Ser Glu Ala Lys
65                  70                  75                  80

Gly Leu Lys Ile Gly Gln Arg Val Gly Ile Gly Trp Thr Ala Glu Ser
                85                  90                  95

Cys Gln Ala Cys Asp Gln Cys Ile Ser Gly Gln Gln Val Leu Cys Thr
            100                 105                 110

Gly Glu Asn Thr Ala Thr Ile Ile Gly His Ala Gly Gly Phe Ala Asp
        115                 120                 125

Lys Val Arg Ala Gly Trp Gln Trp Val Ile Pro Leu Pro Asp Glu Leu
    130                 135                 140

Asp Pro Thr Ser Ala Gly Pro Leu Leu Cys Gly Gly Ile Thr Val Phe
145                 150                 155                 160

Asp Pro Ile Leu Lys His Gln Ile Gln Ala Ile His His Val Ala Val
                165                 170                 175

Ile Gly Ile Gly Gly Leu Gly His Met Ala Ile Lys Leu Leu Lys Ala
            180                 185                 190

Trp Gly Cys Glu Ile Thr Ala Phe Ser Ser Asn Pro Asn Lys Thr Asp
        195                 200                 205

Glu Leu Lys Ala Met Gly Ala Asp His Val Val Asn Ser Arg Asp Asp
    210                 215                 220

Ala Glu Ile Lys Ser Gln Gln Gly Lys Phe Asp Leu Leu Leu Ser Thr
225                 230                 235                 240

Val Asn Val Pro Leu Asn Trp Asn Ala Tyr Leu Asn Thr Leu Ala Pro
                245                 250                 255

Asn Gly Thr Phe His Phe Leu Gly Val Val Met Glu Pro Ile Pro Val
            260                 265                 270

Pro Val Gly Ala Leu Leu Gly Gly Ala Lys Ser Leu Thr Ala Ser Pro
        275                 280                 285

```
Thr Gly Ser Pro Ala Ala Leu Arg Lys Leu Leu Glu Phe Ala Ala Arg
    290                 295                 300

Lys Asn Ile Ala Pro Gln Ile Glu Met Tyr Pro Met Ser Glu Leu Asn
305                 310                 315                 320

Glu Ala Ile Glu Arg Leu His Ser Gly Gln Ala Arg Tyr Arg Ile Val
                325                 330                 335

Leu Lys Ala Asp Phe
            340

<210> SEQ ID NO 10
<211> LENGTH: 339
<212> TYPE: PRT
<213> ORGANISM: Escherichia coli

<400> SEQUENCE: 10

Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
        195                 200                 205

Leu Ala Met Gly Ala Asp Lys Val Val Asn Ser Arg Asp Pro Gln Ala
    210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285

Thr Pro Tyr Glu Leu Arg Lys Leu Met Arg Phe Ala Ala Arg Ser Lys
    290                 295                 300

Val Ala Pro Thr Thr Glu Leu Phe Pro Met Ser Lys Ile Asn Asp Ala
```

```
                        305                 310                 315                 320
Ile Gln His Val Arg Asp Gly Lys Ala Arg Tyr Arg Val Val Leu Lys
                325                 330                 335

Ala Asp Phe

<210> SEQ ID NO 11
<211> LENGTH: 208
<212> TYPE: PRT
<213> ORGANISM: Escherichia coli

<400> SEQUENCE: 11

Met Met Asn Phe Asn Asn Val Phe Arg Trp His Leu Pro Phe Leu Phe
1               5                   10                  15

Leu Val Leu Leu Thr Phe Arg Ala Ala Ala Asp Thr Leu Leu Leu Ile
            20                  25                  30

Leu Gly Asp Ser Leu Ser Ala Gly Tyr Arg Met Ser Ala Ser Ala Ala
        35                  40                  45

Trp Pro Ala Leu Leu Asn Asp Lys Trp Gln Ser Lys Thr Ser Val Val
    50                  55                  60

Asn Ala Ser Ile Ser Gly Asp Thr Ser Gln Gln Gly Leu Ala Arg Leu
65                  70                  75                  80

Pro Ala Leu Leu Lys Gln His Gln Pro Arg Trp Val Leu Val Glu Leu
                85                  90                  95

Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
    130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Lys Gln Leu Gln Pro Leu Val Asn His Asp Ser
        195                 200                 205

<210> SEQ ID NO 12
<211> LENGTH: 209
<212> TYPE: PRT
<213> ORGANISM: Escherichia coli

<400> SEQUENCE: 12

Met Val Asp Met Lys Thr Thr His Thr Ser Leu Pro Phe Ala Gly His
1               5                   10                  15

Thr Leu His Phe Val Glu Phe Asp Pro Ala Asn Phe Cys Glu Gln Asp
            20                  25                  30

Leu Leu Trp Leu Pro His Tyr Ala Gln Leu Gln His Ala Gly Arg Lys
        35                  40                  45

Arg Lys Thr Glu His Leu Ala Gly Arg Ile Ala Ala Val Tyr Ala Leu
    50                  55                  60

Arg Glu Tyr Gly Tyr Lys Cys Val Pro Ala Ile Gly Glu Leu Arg Gln
65                  70                  75                  80

Pro Val Trp Pro Ala Glu Val Tyr Gly Ser Ile Ser His Cys Gly Thr
                85                  90                  95
```

Thr Ala Leu Ala Val Ser Arg Gln Pro Ile Gly Ile Asp Ile Glu
            100                 105                 110

Glu Ile Phe Ser Val Gln Thr Ala Arg Glu Leu Thr Asp Asn Ile Ile
            115                 120                 125

Thr Pro Ala Glu His Glu Arg Leu Ala Asp Cys Gly Leu Ala Phe Ser
        130                 135                 140

Leu Ala Leu Thr Leu Ala Phe Ser Ala Lys Glu Ser Ala Phe Lys Ala
145                 150                 155                 160

Ser Glu Ile Gln Thr Asp Ala Gly Phe Leu Asp Tyr Gln Ile Ile Ser
                165                 170                 175

Trp Asn Lys Gln Gln Val Ile Ile His Arg Glu Asn Glu Met Phe Ala
            180                 185                 190

Val His Trp Gln Ile Lys Glu Lys Ile Val Ile Thr Leu Cys Gln His
        195                 200                 205

Asp

<210> SEQ ID NO 13
<211> LENGTH: 12397
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
cactatacca attgagatgg gctagtcaat gataattact agtccttttc ctttgagttg      60
tgggtatctg taaattctgc tagacctttg ctggaaaact tgtaaattct gctagaccct     120
ctgtaaattc cgctagacct tgtgtgtttt ttttgtttta tattcaagtg gttataattt     180
atagaataaa gaaagaataa aaaagataaa aagaataga tcccagccct gtgtataact      240
cactacttta gtcagttccg cagtattaca aaaggatgtc gcaaacgctg tttgctcctc     300
tacaaaacag accttaaaac cctaaaggcg tcggcatccg cttacagaca agctgtgacc     360
gtctccggga gctgcatgtg tcagaggttt tcaccgtcat caccgaaacg cgcgaggcag     420
cagatcaatt cgcgcgcgaa ggcgaagcgg catgcattta cgttgacacc atcgaatggt     480
gcaaaacctt tcgcggtatg gcatgatagc gcccggaaga gagtcaattc agggtggtga     540
atgtgaaacc agtaacgtta tacgatgtcg cagagtatgc cggtgtctct tatcagaccg     600
tttcccgcgt ggtgaaccag gccagccacg tttctgcgaa aacgcgggaa aaagtggaag     660
cggcgatggc ggagctgaat tacattccca accgcgtggc acaacaactg gcgggcaaac     720
agtcgttgct gattggcgtt gccacctcca gtctggccct gcacgcgccg tcgcaaattg     780
tcgcggcgat taaatctcgc gccgatcaac tgggtgccag cgtggtggtg tcgatggtag     840
aacgaagcgg cgtcgaagcc tgtaaagcgg cggtgcacaa tcttctcgcg caacgcgtca     900
gtgggctgat cattaactat ccgctggatg accaggatgc cattgctgtg gaagctgcct     960
gcactaatgt tccggcgtta tttcttgatg tctctgacca gacacccatc aacagtatta    1020
ttttctccca tgaagacggt acgcgactgg gcgtggagca tctggtcgca ttgggtcacc    1080
agcaaatcgc gctgttagcg ggcccattaa gttctgtctc ggcgcgtctg cgtctggctg    1140
gctggcataa atatctcact cgcaatcaaa ttcagccgat agcggaacgg gaaggcgact    1200
ggagtgccat gtccggtttt caacaaacca tgcaaatgct gaatgagggc atcgttccca    1260
ctgcgatgct ggttgccaac gatcagatgg cgctgggcgc aatgcgcgcc attaccgagt    1320

```
ccgggctgcg cgttggtgcg gatatctcgg tagtgggata cgacgatacc gaagacagct   1380
catgttatat cccgccgtta accaccatca aacaggattt tcgcctgctg ggcaaacca    1440 gcgtggaccg cttgctgcaa ctctctcagg gccaggcggt gaagggcaat cagctgttgc   1500
ccgtctcact ggtgaaaaga aaaccaccc tggcgcccaa tacgcaaacc gcctctcccc    1560
gcgcgttggc cgattcatta atgcagctgg cacgacaggt ttcccgactg aaagcgggc    1620 agtgagcgca acgcaattaa tgtaagttag cgcgaattga tctggtttga cagcttatca   1680
tcgactgcac ggtgcaccaa tgcttctggc gtcaggcagc catcggaagc tgtggtatgg   1740
ctgtgcaggt cgtaaatcac tgcataattc gtgtcgctca aggcgcactc ccgttctgga   1800
taatgttttt tgcgccgaca tcataacggt tctggcaaat attctgaaat gagctgttga   1860
caattaatca tccggctcgt ataatgtgtg gaattgtgag cggataacaa tttcacacag   1920
gaaacagcgc cgctgagaaa aagcgaagcg gcactgctct ttaacaattt atcagacaat   1980
ctgtgtgggc actcgaccgg aattatcgat taactttatt attaaaaatt aaagaggtat   2040
atattaatgt atcgattaaa taaggaggaa taaaccatga cgagcgatgt tcacgacgcg   2100
accgacggcg ttaccgagac tgcactggat gatgagcaga gcactcgtcg tattgcagaa   2160
ctgtacgcaa cggacccaga gttcgcagca gcagctcctc tgccggccgt tgtcgatgcg   2220
gcgcacaaac cgggcctgcg tctggcggaa atcctgcaga ccctgttcac cggctacggc   2280
gatcgtccgg cgctgggcta tcgtgcacgt gagctggcga cggacgaagg cggtcgtacg   2340
gtcacgcgtc tgctgccgcg cttcgatacc ctgacctatg cacaggtgtg gagccgtgtt   2400
caagcagtgg ctgcagcgtt gcgtcacaat ttcgcacaac cgatttaccc gggcgacgcg   2460
gtcgcgacta tcggctttgc gagcccggac tatttgacgc tggatctggt gtgcgcgtat   2520
ctgggcctgg tcagcgttcc tttgcagcat aacgctccgg tgtctcgcct ggccccgatt   2580
ctggccgagg tggaaccgcg tattctgacg gtgagcgcag aatacctgga cctggcggtt   2640
gaatccgtcc gtgatgtgaa ctccgtcagc cagctggttg ttttcgacca tcatccggaa   2700
gtggacgatc accgtgacgc actggctcgc gcacgcgagc agctggccgg caaaggtatc   2760
gcagttacga ccctggatgc gatcgcagac gaaggcgcag gtttgccggc tgagccgatt   2820
tacacggcgg atcacgatca gcgtctggcc atgattctgt ataccagcgg ctctacgggt   2880
gctccgaaag gcgcgatgta caccgaagcg atggtggctc gcctgtggac tatgagctt    2940 atcacgggcg acccgacccc ggttatcaac gtgaacttca tgccgctgaa ccatctgggc   3000
ggtcgtatcc cgattagcac cgccgtgcag aatggcggta ccagctactt cgttccggaa   3060
agcgacatga gcacgctgtt tgaggatctg gccctggtcc gccctaccga actgggtctg   3120
gtgccgcgtg ttgcggacat gctgtaccag catcatctgg cgaccgtgga tcgcctggtg   3180
acccagggcg cggacgaact gactgcggaa aagcaggccg gtgcggaact gcgtgaacag   3240
gtcttgggcg tcgtgttat caccggtttt gtttccaccg cgccgttggc ggcagagatg   3300
cgtgcttttc tggatatcac cttgggtgca cacatcgttg acggttacgg tctgaccgaa   3360
accggtgcgg tcacccgtga tggtgtgatt gttcgtcctc cggtcattga ttacaagctg   3420
atcgatgtgc cggagctggg ttacttctcc accgacaaac cgtacccgcg tggcgagctg   3480
ctggttcgta gccaaacgtt gactccgggt tactacaagc gcccagaagt caccgcgtcc   3540
gttttcgatc gcgacggcta ttaccacacc ggcgacgtga tggcagaaac cgcgccagac   3600
cacctggtgt atgtggaccg ccgcaacaat gttctgaagc tggcgcaagg tgaatttgtc   3660
```

```
gccgtggcta acctggaggc cgttttcagc ggcgctgctc tggtccgcca gattttcgtg    3720
tatggtaaca gcgagcgcag cttttctgttg gctgttgttg tccctacccc ggaggcgctg    3780
gagcaatacg accctgccgc attgaaagca gccctggcgg attcgctgca gcgtacggcg    3840
cgtgatgccg agctgcagag ctatgaagtg ccggcggact tcattgttga gactgagcct    3900
tttagcgctg cgaacggtct gctgagcggt gttggcaagt tgctgcgtcc gaatttgaag    3960
gatcgctacg gtcagcgttt ggagcagatg tacgcggaca tcgcggctac gcaggcgaac    4020
caattgcgtg aactgcgccg tgctgcggct actcaaccgg tgatcgacac gctgacgcaa    4080
gctgcggcga ccatcctggg taccggcagc gaggttgcaa gcgacgcaca ctttactgat    4140
ttgggcggtg attctctgag cgcgctgacg ttgagcaact tgctgtctga cttctttggc    4200
tttgaagtcc cggttggcac gattgttaac ccagcgacta atctggcaca gctggcgcaa    4260
catatcgagg cgcagcgcac ggcgggtgac cgccgtccat cctttacgac ggtccacggt    4320
gcggatgcta cggaaatccg tgcaagcgaa ctgactctgg acaaattcat cgacgctgag    4380
actctgcgcg cagcacctgg tttgccgaag gttacgactg agccgcgtac ggtcctgttg    4440
agcggtgcca atggttggtt gggccgcttc ctgaccctgc agtggctgga acgtttggca    4500
ccggttggcg gtaccctgat caccattgtg cgcggtcgtg acgatgcagc ggcacgtgca    4560
cgtttgactc aggcttacga tacggaccca gagctgtccc gccgcttcgc tgagttggcg    4620
gatcgccact gcgtgtggt ggcaggtgat atcggcgatc cgaatctggg cctgaccccg    4680
gagatttggc accgtctggc agcagaggtc gatctggtcg ttcatccagc ggccctggtc    4740
aaccacgtcc tgccgtaccg ccagctgttt ggtccgaatg ttgttggcac cgccgaagtt    4800
atcaagttgg ctctgaccga gcgcatcaag cctgttacct acctgtccac ggttagcgtc    4860
gcgatgggta ttcctgattt tgaggaggac ggtgacattc gtaccgtcag cccggttcgt    4920
ccgctggatg gtggctatgc aaatggctat ggcaacagca gtgggctgg cgaggtgctg    4980
ctgcgcgagg cacatgacct gtgtggcctg ccggttgcga cgtttcgtag cgacatgatt    5040
ctggcccacc cgcgctaccg tggccaagtg aatgtgccgg acatgttcac ccgtctgctg    5100
ctgtccctgc tgatcacggg tgtggcaccg cgttccttct acattggtga tggcgagcgt    5160
ccgcgtgcac actacccggg cctgaccgtc gattttgttg cggaagcggt tactaccctg    5220
ggtgctcagc aacgtgaggg ttatgtctcg tatgacgtta tgaatccgca cgatgacggt    5280
attagcttgg atgtctttgt ggactggctg attcgtgcgg ccacccaat tgaccgtgtt    5340
gacgactatg atgactgggt gcgtcgtttt gaaaccgccgt tgaccgcctt gccggagaaa    5400
cgtcgtgcgc agaccgttct gccgctgctg catgcctttc gcgcgccaca ggcgccgttg    5460
cgtggcgccc ctgaaccgac cgaagtgttt catgcagcgg tgcgtaccgc taaagtcggt    5520
ccgggtgata ttccgcacct ggatgaagcc ctgatcgaca agtacatccg tgacctgcgc    5580
gagttcggtc tgatttagaa ttccataatt gctgttagga gatatatatg gcggacacgt    5640
tattgattct gggtgatagc ctgagcgccg ggtatcgaat gtctgccagc gcggcctggc    5700
ctgccttgtt gaatgataag tggcagagta aaacgtcggt agttaatgcc agcatcagcg    5760
gcgacacctc gcaacaagga ctggcgcgcc ttccggctct gctgaaacag catcagccgc    5820
gttgggtgct ggttgaactg ggcggctgtg acggtttgcg tggttttcag ccacagcaaa    5880
ccgagcaaac gctgcgccag attttgcagg atgtcaaagc cgccaacgct cttccattgt    5940
taatgcaaat acgtctgcct tacaactatg gtcgtcgtta taatgaagcc tttagcgcca    6000
tttaccccaa actcgccaaa gagtttgatg ttccgctgct gccctttttt atggaagagg    6060
```

```
tctgcctcaa gccacaatgg atgcaggatg acggtattca tcccaaccgc gacgcccagc   6120
cgtttattgc cgactggatg gcgaagcagt tgcagccttt aaccaatcat gactcataag   6180
cttctaagga aataatagga gattgaaaat ggcaacaact aatgtgattc atgcttatgc   6240
tgcaatgcag gcaggtgaag cactcgtgcc ttattcgttt gatgcaggcg aactgcaacc   6300
acatcaggtt gaagttaaag tcgaatattg tgggctgtgc cattccgatg tctcggtact   6360
caacaacgaa tggcattctt cggtttatcc agtcgtggca ggtcatgaag tgattggtac   6420
gattacccaa ctgggaagtg aagccaaagg actaaaaatt ggtcaacgtg ttggtattgg   6480
ctggacggca gaaagctgtc aggcctgtga ccaatgcatc agtggtcagc aggtattgtg   6540
cacgggcgaa ataccgcaa ctattattgg tcatgctggt ggctttgcag ataaggttcg   6600
tgcaggctgg caatgggtca ttcccctgcc gacgaactc gatccgacca gtgctggtcc   6660
tttgctgtgt ggcggaatca cagtatttga tccaatttta aaacatcaga ttcaggctat   6720
tcatcatgtt gctgtgattg gtatcggtgg tttgggacat atggccatca agctacttaa   6780
agcatggggc tgtgaaatta ctgcgtttag ttcaaatcca aacaaaaccg atgagctcaa   6840
agctatgggg gccgatcacg tggtcaatag ccgtgatgat gccgaaatta aatcgcaaca   6900
gggtaaattt gatttactgc tgagtacagt taatgtgcct ttaaactgga atgcgtatct   6960
aaacacactg gcacccaatg gcactttcca tttttgggc gtggtgatgg aaccaatccc   7020
tgtacctgtc ggtgcgctgc taggaggtgc caaatcgcta acagcatcac caactggctc   7080
gcctgctgcc ttacgtaagc tgctcgaatt tgcggcacgt aagaatatcg cacctcaaat   7140
cgagatgtat cctatgtcgg agctgaatga ggccatcgaa cgcttacatt cgggtcaagc   7200
acgttatcgg attgtactta aagccgattt ttaacctagg gataatagag gttaagagcg   7260
gccagatgcc acattcctac gattacgatg ccatagtaat aggttccggc cccggcggcg   7320
aaggcgctgc aatgggcctg gttaagcaag gtgcgcgcgt cgcagttatc gagcgttatc   7380
aaaatgttgg cggcggttgc acccactggg gcaccatccc gtcgaaagct ctccgtcacg   7440
ccgtcagccg cattatagaa ttcaatcaaa acccacttta cagcgaccat tcccgactgc   7500
tccgctcttc ttttgccgat atccttaacc atgccgataa cgtgattaat caacaaacgc   7560
gcatgcgtca gggattttac gaacgtaatc actgtgaaat attgcaggga aacgctcgct   7620 tgttgacga gcatacgttg gcgctggatt gcccggacgg cagcgttgaa cactaaccg   7680 ctgaaaaatt tgttattgcc tgcggctctc gtccatatca tccaacagat gttgatttca   7740
cccatccacg catttacgac agcgactcaa ttctcagcat gcaccacgaa ccgcgccatg   7800
tacttatcta tggtgctgga gtgatcggct gtgaatatgc gtcgatcttc gcggtatgg   7860 atgtaaaagt ggatcgatc aacacccgcg atcgcctgct ggcatttctc gatcaagaga   7920
tgtcagattc tctctcctat cacttctgga acagtggcgt agtgattcgt cacaacgaag   7980
agtacgagaa gatcgaaggc tgtgacgatg gtgtgatcat gcatctgaag tcgggtaaaa   8040
aactgaaagc tgactgcctg ctctatgcca acggtcgcac cggtaatacc gattcgctgg   8100
cgttacagaa cattgggcta gaaactgaca gccgcggaca gctgaaggtc aacagcatgt   8160
atcagaccgc acagccacac gtttacgcgg tgggcgacgt gattggttat ccgagcctgg   8220
cgtcggcggc ctatgaccag gggcgcattg ccgcgcaggc gctggtaaaa ggcgaagcca   8280
ccgcacatct gattgaagat atccctaccg gtatttacac catcccggaa atcagctctg   8340
tgggcaaaac cgaacagcag ctgaccgcaa tgaaagtgcc atatgaagtg ggccgcgccc   8400
```

```
agtttaaaca tctggcacgc gcacaaatcg tcggcatgaa cgtgggcacg ctgaaaattt    8460
tgttccatcg ggaaacaaaa gagattctgg gtattcactg cttttggcgag cgcgctgccg   8520 aaattattca tatcggtcag gcgattatgg aacagaaagg tggcggcaac actattgagt   8580
acttcgtcaa caccacctttt aactacccga cgatggcgga agcctatcgg gtagctgcgt  8640
taaacggttt aaaccgcctg ttttaaactt tatcgaaatg gccatccatt cttggtttaa    8700
acggtctcca gcttggctgt tttgcggat gagagaagat tttcagcctg atacagatta   8760
aatcagaacg cagaagcggt ctgataaaac agaatttgcc tggcggcagt agcgcggtgg  8820
tcccacctga ccccatgccg aactcagaag tgaaacgccg tagcgccgat ggtagtgtgg   8880
ggtctcccca tgcgagagta gggaactgcc aggcatcaaa taaaacgaaa ggctcagtcg   8940
aaagactggg cctttcgttt tatctgttgt ttgtcggtga acgctctcct gacgcctgat   9000
gcggtatttt ctccttacgc atctgtgcgg tatttcacac cgcatatggt gcactctcag   9060
tacaatctgc tctgatgccg catagttaag ccagccccga cacccgccaa cacccgctga   9120
cgagcttagt aaagccctcg ctagatttta atgcggatgt tgcgattact tcgccaacta   9180
ttgcgataac aagaaaaagc cagccttttca tgatatatct cccaatttgt gtagggctta   9240
ttatgcacgc ttaaaaataa taaaagcaga cttgacctga tagtttggct gtgagcaatt   9300
atgtgcttag tgcatctaac gcttgagtta agccgcgccg cgaagcggcg tcggcttgaa   9360
cgaattgtta gacattattt gccgactacc ttggtgatct cgcctttcac gtagtggaca   9420
aattcttcca actgatctgc gcgcgaggcc aagcgatctt cttcttgtcc aagataagcc   9480
tgtctagctt caagtatgac gggctgatac tgggccggca ggcgctccat tgcccagtcg   9540
gcagcgacat ccttcggcgc gattttgccg gttactgcgc tgtaccaaat gcgggacaac   9600
gtaagcacta catttcgctc atcgccagcc cagtcgggcg gcgagttcca tagcgttaag   9660
gtttcattta gcgcctcaaa tagatcctgt tcaggaaccg gatcaaagag ttcctccgcc   9720
gctggaccta ccaaggcaac gctatgttct cttgctttg tcagcaagat agccagatca   9780
atgtcgatcg tggctggctc gaagatacct gcaagaatgt cattgcgctg ccattctcca   9840
aattgcagtt cgcgcttagc tggataacgc cacggaatga tgtcgtcgtg cacaacaatg   9900
gtgacttcta cagcgcggag aatctcgctc tctccagggg aagccgaagt ttccaaaagg   9960
tcgttgatca aagctcgccg cgttgtttca tcaagcctta cggtcaccgt aaccagcaaa  10020
tcaatatcac tgtgtggctt caggccgcca tccactgcgg agccgtacaa atgtacggcc   10080
agcaacgtcg gttcgagatg gcgctcgatg acgccaacta cctctgatag ttgagtcgat  10140
acttcggcga tcaccgcttc cctcatgatg tttaactttg ttttagggcg actgccctgc   10200
tgcgtaacat cgttgctgct ccataacatc aaacatcgac ccacggcgta acgcgcttgc   10260
tgcttggatg cccgaggcat agactgtacc ccaaaaaaac agtcataaca agccatgaaa   10320
accgccactg cgccgttacc accgctgcgt tcggtcaagg ttctggacca gttgcgtgag   10380
cgcatacgct acttgcatta cagcttacga accgaacagg cttatgtcca ctgggttcgt   10440
gccttcatcc gtttccacgg tgtgcgtcac ccggcaacct tgggcagcag cgaagtcgag   10500
gcatttctgt cctggctggc gaacgagcgc aaggtttcgg tctccacgca tcgtcaggca  10560
ttggcggcct tgctgttctt ctacggcaag gtgctgtgca cggatctgcc ctggcttcag   10620
gagatcggaa gacctcggcc gtcgcggcgc ttgccggtgg tgctgacccc ggatgaagtg   10680
gttcgcatcc tcggttttct ggaaggcgag catcgtttgt tcgcccagct tctgtatgga   10740
acgggcatgc ggatcagtga gggtttgcaa ctgcgggtca aggatctgga tttcgatcac   10800
```

```
ggcacgatca tcgtgcggga gggcaagggc tccaaggatc gggccttgat gttacccgag    10860
agcttggcac ccagcctgcg cgagcagggg aattaattcc cacggttttt gctgcccgca    10920
aacgggctgt tctggtgttg ctagtttgtt atcagaatcg cagatccggc ttcagccggt    10980
ttgccggctg aaagcgctat ttcttccaga attgccatga ttttttcccc acgggaggcg    11040
tcactggctc ccgtgttgtc ggcagctttg attcgataag cagcatcgcc tgtttcaggc    11100
tgtctatgtg tgactgttga gctgtaacaa gttgtctcag gtgttcaatt tcatgttcta    11160
gttgctttgt tttactggtt tcacctgttc tattaggtgt tacatgctgt tcatctgtta    11220
cattgtcgat ctgttcatgg tgaacagctt tgaatgcacc aaaaactcgt aaaagctctg    11280
atgtatctat cttttttaca ccgttttcat ctgtgcatat ggacagtttt ccctttgata    11340
tgtaacggtg aacagttgtt ctactttgt ttgttagtct tgatgcttca ctgatagata    11400
caagagccat aagaacctca gatccttccg tatttagcca gtatgttctc tagtgtggtt    11460
cgttgttttt gcgtgagcca tgagaacgaa ccattgagat catacttact ttgcatgtca    11520
ctcaaaaatt ttgcctcaaa actggtgagc tgaattttg cagttaaagc atcgtgtagt    11580
gttttcttta gtccgttatg taggtaggaa tctgatgtaa tggttgttgg tattttgtca    11640
ccattcattt ttatctggtt gttctcaagt tcggttacga gatccatttg tctatctagt    11700
tcaacttgga aaatcaacgt atcagtcggg cggcctcgct tatcaaccac caatttcata    11760
ttgctgtaag tgtttaaatc tttacttatt ggtttcaaaa cccattggtt aagccttta    11820 aactcatggt agttattttc aagcattaac atgaacttaa attcatcaag gctaatctct    11880
atatttgcct tgtgagtttt cttttgtgtt agttcttta ataaccactc ataaatcctc    11940
atagagtatt tgttttcaaa agacttaaca tgttccagat tatattttat gaattttttt    12000
aactggaaaa gataaggcaa tatctcttca ctaaaaacta attctaattt ttcgcttgag    12060
aacttggcat agtttgtcca ctggaaaatc tcaaagcctt taaccaaagg attcctgatt    12120
tccacagttc tcgtcatcag ctctctggtt gctttagcta atacaccata agcatttcc     12180 ctactgatgt tcatcatctg agcgtattgg ttataagtga acgataccgt ccgttctttc    12240
cttgtagggt tttcaatcgt ggggttgagt agtgccacac agcataaaat tagcttggtt    12300
tcatgctccg ttaagtcata gcgactaatc gctagttcat ttgctttgaa aacaactaat    12360
tcagacatac atctcaattg gtctaggtga tttaat                              12397
```

<210> SEQ ID NO 14
<211> LENGTH: 3227
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
gacgaaaggg cctcgtgata cgcctatttt tataggttaa tgtcatgata ataatggttt      60
cttagacgtc aggtggcact tttcggggaa atgtgcgcgg aaccccatt tgtttatttt     120 tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gttttgtctc acccagaaac gctggtgaaa gtaaaagatg    300
ctgaagatca gttgggtgca cgagtgggtt acatcgaact ggatctcaac agcggtaaga    360
```

```
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt tgtgcatccg aagatcagca   1140
gttcaacctg ttgatagtac gtactaagct ctcatgtttc acgtactaag ctctcatgtt   1200
taacgtacta agctctcatg tttaacgaac taaaccctca tggctaacgt actaagctct   1260
catggctaac gtactaagct ctcatgtttg aacaataaaa ttaatataaa tcagcaactt   1320
aaatagcctc taaggtttta agttttataa gaaaaaaaag aatatataag gcttttaaag   1380
ctagctttta aggtttcacc atgttctttc ctgcgttatc ccctgattct gtggataacc   1440
gtattaccgc ctttgagtga gctgataccg ctcgccgcag ccgaacgacc gagcgcagcg   1500
agtcagtgag cgaggaagcg gaagagcgcc caatacgcaa accgcctctc cccgcgcgtt   1560
ggccgattca ttaagacagc tgtctcttat acacatctca accctgaagc tcttgttggc   1620
tagtgcgtag tcgttggcaa gctttccgct gtttctgcat tcttacgttt taggatgcat   1680
atggcggccg cataacttcg tatagcatac attatacgaa gttatctaga gttgcatgcc   1740
tgcaggtccg cttattatca cttattcagg cgtagcaacc aggcgtttaa gggcaccaat   1800
aactgcctta aaaaaattac gccccgcccc tgccactcatc gcagtactgt tgtaattcat   1860
taagcattct gccgacatgg aagccatcac aaacggcatg atgaacctga atcgccagcg   1920
gcatcagcac cttgtcgcct tgcgtataat atttgcccat ggtgaaaacg ggggcgaaga   1980
agttgtccat attggccacg tttaaatcaa aactggtgaa actcacccag ggattggctg   2040
agacgaaaaa catattctca ataaacccct tagggaaata ggccaggttt tcaccgtaac   2100
acgccacatc ttgcgaatat atgtgtagaa actgccggaa atcgtcgtgg tattcactcc   2160
agagcgatga aaacgtttca gtttgctcat ggaaaacggt gtaacaaggg tgaacactat   2220
cccatatcac cagctcaccg tctttcattg ccatacggaa ttccggatga gcattcatca   2280
ggcgggcaag aatgtgaata aaggccggat aaaacttgtg cttatttttc tttacggtct   2340
ttaaaaaggc cgtaatatcc agctgaacgg tctggttata ggtacattga gcaactgact   2400
gaaatgcctc aaaatgttct ttacgatgcc attgggatat atcaacggtg gtatatccag   2460
tgattttttt ctccatttta gcttccttag ctcctgaaaa tctcgataac tcaaaaaata   2520
cgcccggtag tgatcttatt tcattatggt gaaagttgga acctcttacg tgccgatcaa   2580
cgtctcattt tcgccaaaag ttggcccagg cttcccggt atcaacaggg acaccaggat   2640
ttatttattc tgcgaagtga tcttccgtca caggtattta ttcgactcta gataacttcg   2700
tatagcatac attatacgaa gttatggatc cagcttatcg ataccgtcaa acaaatcata   2760
```

```
aaaaatttat tgctttcag gaaaattttt ctgtataata gattcaattg cgatgacgac    2820
gaacacgcat taaggaggtg aagagctcga attcgagcca atatgcgaga acacccgaga    2880
aaattcatcg atgatggttg agatgtgtat aagagacagc tgtcgtaata gcgaagaggc    2940
ccgcaccgat cgcccttccc aacagttgcg cagcctgaat ggcgaatggc gcctgatgcg    3000
gtattttctc cttacgcatc tgtgcggtat ttcacaccgc atatggtgca ctctcagtac    3060
aatctgctct gatgccgcat agttaagcca gccccgacac ccgccaacac ccgctgacgc    3120
gccctgacgg gcttgtctgc tcccggcatc cgcttacaga caagctgtga ccgtctccgg    3180
gagctgcatg tgtcagaggt tttcaccgtc atcaccgaaa cgcgcga                 3227
```

<210> SEQ ID NO 15
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 15

```
gcagttattg gtgcccttaa acgcctggtt gctacgcctg                           40
```

<210> SEQ ID NO 16
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 16

```
cccagggctt cccggtatca acagggacac cagg                                 34
```

<210> SEQ ID NO 17
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 17

```
atggtcatta aggcgcaaag cccgg                                           25
```

<210> SEQ ID NO 18
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 18

```
gagaccccac actaccatcc tcgagttatc gcccctgaat ggctaaatca ccc            53
```

<210> SEQ ID NO 19
<211> LENGTH: 27
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 19
ctcgaggatg gtagtgtggg gtctccc                                          27

<210> SEQ ID NO 20
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
gagaccgttt ctcgaattta aatatgatac gctcgagctt cgtctgtttc tactggtatt      60
ggcacaaac                                                              69

<210> SEQ ID NO 21
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (34)..(40)
<223> OTHER INFORMATION: a, c, t, g, unknown or other

<400> SEQUENCE: 21
tgaaagatta aatttnhhar nddhddnwag gagnnnnnnn atggtcatta aggcgcaaag      60
cccgg                                                                 65

<210> SEQ ID NO 22
<211> LENGTH: 12206
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
cactatacca attgagatgg gctagtcaat gataattact agtcctttc ctttgagttg       60 tgggtatctg taaattctgc tagacctttg ctggaaaact tgtaaattct gctagaccct    120
ctgtaaattc cgctagacct tgtgtgtttt tttttgttta tattcaagtg gttataattt    180
atagaataaa gaaagaataa aaaagataaa aagaataga tcccagccct gtgtataact     240
cactacttta gtcagttccg cagtattaca aaaggatgtc gcaaacgctg tttgctcctc    300
tacaaaacag accttaaaac cctaaaggcg tcggcatccg cttacagaca agctgtgacc    360
```

```
gtctccggga gctgcatgtg tcagaggttt tcaccgtcat caccgaaacg cgcgaggcag    420
cagatcaatt cgcgcgcgaa ggcgaagcgg catgcattta cgttgacacc atcgaatggt    480
gcaaaacctt tcgcggtatg gcatgatagc gcccggaaga gagtcaattc agggtggtga    540
atgtgaaacc agtaacgtta tacgatgtcg cagagtatgc cggtgtctct tatcagaccg    600
tttcccgcgt ggtgaaccag gccagccacg tttctgcgaa aacgcgggaa aaagtggaag    660
cggcgatggc ggagctgaat tacattccca accgcgtggc acaacaactg gcgggcaaac    720
agtcgttgct gattggcgtt gccacctcca gtctggccct gcacgcgccg tcgcaaattg    780
tcgcggcgat taaatctcgc gccgatcaac tgggtgccag cgtggtggtg tcgatggtag    840
aacgaagcgg cgtcgaagcc tgtaaagcgg cggtgcacaa tcttctcgcg caacgcgtca    900
gtgggctgat cattaactat ccgctggatg accaggatgc cattgctgtg gaagctgcct    960
gcactaatgt tccggcgtta tttcttgatg tctctgacca gacacccatc aacagtatta   1020 tttttctccca tgaagacggt acgcgactgg gcgtggagca tctggtcgca ttgggtcacc   1080
agcaaatcgc gctgttagcg ggcccattaa gttctgtctc ggcgcgtctg cgtctggctg   1140
gctggcataa atatctcact cgcaatcaaa ttcagccgat agcggaacgg gaaggcgact   1200
ggagtgccat gtccggtttt caacaaacca tgcaaatgct gaatgagggc atcgttccca   1260
ctgcgatgct ggttgccaac gatcagatgg cgctgggcgc aatgcgcgcc attaccgagt   1320
ccgggctgcg cgttggtgcg gatatctcgg tagtgggata cgacgatacc gaagacagct   1380
catgttatat cccgccgtta accaccatca acaggatttt cgcctgctg gggcaaacca   1440 gcgtggaccg cttgctgcaa ctctctcagg gccaggcggt gaagggcaat cagctgttgc   1500
ccgtctcact ggtgaaaaga aaaccaccc tggcgcccaa tacgcaaacc gcctctcccc   1560
gcgcgttggc cgattcatta atgcagctgg cacgacaggt ttcccgactg gaaagcgggc   1620
agtgagcgca acgcaattaa tgtaagttag cgcgaattga tctggtttga cagcttatca   1680
tcgactgcac ggtgcaccaa tgcttctggc gtcaggcagc catcggaagc tgtggtatgg   1740
ctgtgcaggt cgtaaatcac tgcataattc gtgtcgctca aggcgcactc ccgttctgga   1800
taatgttttt tgcgccgaca tcataacggt tctggcaaat attctgaaat gagctgttga   1860
caattaatca tccggctcgt ataatgtgtg gaattgtgag cggataacaa tttcacacag   1920
gaaacagcgc cgctgagaaa aagcgaagcg gcactgctct ttaacaattt atcagacaat   1980
ctgtgtgggc actcgaccgg aattatcgat taactttatt attaaaaatt aaagaggtat   2040
atattaatgt atcgattaaa taaggaggaa taaaccatga cgagcgatgt tcacgacgcg   2100
accgacggcg ttaccgagac tgcactggat gatgagcaga gcactcgtcg tattgcagaa   2160
ctgtacgcaa cggacccaga gttcgcagca gcagctcctc tgccggccgt tgtcgatgcg   2220
gcgcacaaac cgggcctgcg tctggcggaa atcctgcaga ccctgttcac cggctacggc   2280
gatcgtccgg cgctgggcta tcgtgcacgt gagctggcga cggacgaagg cggtcgtacg   2340
gtcacgcgtc tgctgccgcg cttcgatacc ctgacctatg cacaggtgtg gagccgtgtt   2400
caagcagtgg ctgcagcgtt gcgtcacaat ttcgcacaac cgatttaccc gggcgacgcg   2460
gtcgcgacta tcgctttgc gagcccggac tatttgacgc tggatctggt gtgcgcgtat   2520
ctgggcctgg tcagcgttcc tttgcagcat aacgctccgg tgtctcgcct ggccccgatt   2580
ctggccgagg tggaaccgcg tattctgacg gtgagcgcag aatacctgga cctgcggtt   2640 gaatccgtcc gtgatgtgaa ctccgtcagc cagctggttg ttttcgacca tcatccggaa   2700
```

```
gtggacgatc accgtgacgc actggctcgc gcacgcgagc agctggccgg caaaggtatc    2760
gcagttacga ccctggatgc gatcgcagac gaaggcgcag gtttgccggc tgagccgatt    2820
tacacggcgg atcacgatca gcgtctggcc atgattctgt ataccagcgg ctctacgggt    2880
gctccgaaag gcgcgatgta caccgaagcg atggtggctc gcctgtggac tatgagcttt    2940
atcacgggcg acccgacccc ggttatcaac gtgaacttca tgccgctgaa ccatctgggc    3000
ggtcgtatcc cgattagcac cgccgtgcag aatggcggta ccagctactt cgttccggaa    3060
agcgacatga gcacgctgtt tgaggatctg gccctggtcc gccctaccga actgggtctg    3120
gtgccgcgtg ttgcggacat gctgtaccag catcatctgg cgaccgtgga tcgcctggtg    3180
acccagggcg cggacgaact gactgcggaa aagcaggccg gtgcggaact gcgtgaacag    3240
gtcttgggcg gtcgtgttat caccggtttt gtttccaccg cgccgttggc ggcagagatg    3300
cgtgcttttc tggatatcac cttgggtgca cacatcgttg acggttacgg tctgaccgaa    3360
accggtgcgg tcacccgtga tggtgtgatt gttcgtcctc cggtcattga ttacaagctg    3420
atcgatgtgc cggagctggg ttacttctcc accgacaaac cgtacccgcg tggcgagctg    3480
ctggttcgta gccaaacgtt gactccgggt tactacaagc gcccagaagt caccgcgtcc    3540
gttttcgatc gcgacggcta ttaccacacc ggcgacgtga tggcagaaac cgcgccagac    3600
cacctggtgt atgtggaccg ccgcaacaat gttctgaagc tggcgcaagg tgaatttgtc    3660
gccgtggcta acctggaggc cgttttcagc ggcgctgctc tggtccgcca gattttcgtg    3720
tatggtaaca gcgagcgcag ctttctgttg gctgttgttg tccctacccc ggaggcgctg    3780
gagcaatacg accctgccgc attgaaagca gccctggcgg attcgctgca gcgtacggcg    3840
cgtgatgccg agctgcagag ctatgaagtg ccggcggact tcattgttga gactgagcct    3900
tttagcgctg cgaacggtct gctgagcggt gttggcaagt gctgcgtcc gaatttgaag    3960 gatcgctacg gtcagcgttt ggagcagatg tacgcggaca tcgcggctac gcaggcgaac    4020
caattgcgtg aactgcgccg tgctgcggct actcaaccgg tgatcgacac gctgacgcaa    4080
gctgcggcga ccatcctggg taccggcagc gaggttgcaa gcgacgcaca ctttactgat    4140
ttgggcggtg attctctgag cgcgctgacg ttgagcaact tgctgtctga cttcttttggc    4200 tttgaagtcc cggttggcac gattgttaac ccagcgacta atctggcaca gctggcgcaa    4260
catatcgagg cgcagcgcac ggcgggtgac cgccgtccat cctttacgac ggtccacggt    4320
gcggatgcta cggaaatccg tgcaagcgaa ctgactctgg acaaattcat cgacgctgag    4380
actctgcgcg cagcacctgg tttgccgaag gttacgactg agccgcgtac ggtcctgttg    4440
agcggtgcca atggttggtt gggccgcttc ctgaccctgc agtggctgga acgtttggca    4500
ccggttggcg gtaccctgat caccattgtg cgcggtcgtg acgatgcagc ggcacgtgca    4560
cgtttgactc aggcttacga tacggaccca gagctgtccc gccgcttcgc tgagttggcg    4620
gatcgccact tgcgtgtggt ggcaggtgat atcggcgatc gaatctgggg cctgaccccg    4680
gagatttggc accgtctggc agcagaggtc gatctggtcg ttcatccagc ggccctggtc    4740
aaccacgtcc tgccgtaccg ccagctgttt ggtccgaatg ttgttggcac cgccgaagtt    4800
atcaagttgg ctctgaccga gcgcatcaag cctgttacct acctgtccac ggttagcgtc    4860
gcgatgggta ttcctgattt tgaggaggac ggtgacattc gtaccgtcag cccggttcgt    4920
ccgctggatg gtggctatgc aaatggctat ggcaacagca gtgggctgg cgaggtgctg    4980 ctgcgcgagg cacatgaccc tgtgtggcct gccggttgcga cgtttcgtag cgacatgatt    5040
ctggcccacc cgcgctaccg tggccaagtg aatgtgccgg acatgttcac ccgtctgctg    5100
```

```
ctgtccctgc tgatcacggg tgtggcaccg cgttccttct acattggtga tggcgagcgt    5160
ccgcgtgcac actacccggg cctgaccgtc gattttgttg cggaagcggt tactaccctg    5220
ggtgctcagc aacgtgaggg ttatgtctcg tatgacgtta tgaatccgca cgatgacggt    5280
attagcttgg atgtctttgt ggactggctg attcgtgcgg gccacccaat tgaccgtgtt    5340
gacgactatg atgactgggt gcgtcgtttt gaaaccgcgt tgaccgcctt gccggagaaa    5400
cgtcgtgcgc agaccgttct gccgctgctg catgcctttc gcgcgccaca ggcgccgttg    5460
cgtggcgccc ctgaaccgac cgaagtgttt catgcagcgg tgcgtaccgc taaagtcggt    5520
ccgggtgata ttccgcacct ggatgaagcc ctgatcgaca agtacatccg tgacctgcgc    5580
gagttcggtc tgatttagaa ttctttagcg ttaagaagga gatatatatg gcggacacgt    5640
tattgattct gggtgatagc ctgagcgccg ggtatcgaat gtctgccagc gcggcctggc    5700
ctgccttgtt gaatgataag tggcagagta aacgtcggt  agttaatgcc agcatcagcg    5760
gcgacacctc gcaacaagga ctggcgcgcc ttccggctct gctgaaacag catcagccgc    5820
gttgggtgct ggttgaactg ggcggcaatg acggtttgcg tggttttcag ccacagcaaa    5880
ccgagcaaac gctgcgccag attttgcagg atgtcaaagc cgccaacgct gaaccattgt    5940
taatgcaaat acgtctgcct tacaactatg gtcgtcgtta taatgaagcc tttagcgcca    6000
tttaccccaa actcgccaaa gagtttgatg ttccgctgct gcccttttt  atggaagagg    6060
tctgcctcaa gccacaatgg atgcaggatg acggtattca tcccaaccgc gacgcccagc    6120
cgtttattgc cgactggatg gcgaagcagt tgcagccttt agtaaatcat gactcataag    6180
cttctaagga ataatagga  gattgaaaat ggcaacaact aatgtgattc atgcttatgc    6240
tgcaatgcag gcaggtgaag cactcgtgcc ttattcgttt gatgcaggcg aactgcaacc    6300
acatcaggtt gaagttaaag tcgaatattg tgggctgtgc cattccgatg tctcggtact    6360
caacaacgaa tggcattctt cggtttatcc agtcgtggca ggtcatgaag tgattggtac    6420
gattacccaa ctgggaagtg aagccaaagg actaaaaatt ggtcaacgtg ttggtattgg    6480
ctggacggca gaaagctgtc aggcctgtga ccaatgcatc agtggtcagc aggtattgtg    6540
cacgggcgaa ataccgcaa  ctattattgg tcatgctggt ggctttgcag ataaggttcg    6600
tgcaggctgg caatgggtca ttcccctgcc cgacgaactc gatccgacca gtgctggtcc    6660
tttgctgtgt ggcggaatca cagtatttga tccaattta  aaacatcaga ttcaggctat    6720
tcatcatgtt gctgtgattg gtatcggtgg tttgggacat atggccatca agctacttaa    6780
agcatggggc tgtgaaatta ctgcgtttag ttcaaatcca acaaaaccg  atgagctcaa    6840
agctatgggg gccgatcacg tggtcaatag ccgtgatgat gccgaaatta atcgcaaca     6900
gggtaaattt gatttactgc tgagtacagt taatgtgcct ttaaactgga atgcgtatct    6960
aaacacactg gcacccaatg gcactttcca ttttttgggc gtggtgatgg aaccaatccc    7020
tgtacctgtc ggtgcgctgc taggaggtgc caaatcgcta acagcatcac caactggctc    7080
gcctgctgcc ttacgtaagc tgctcgaatt tgcggcacgt aagaatatcg cacctcaaat    7140
cgagatgtat cctatgtcgg agctgaatga ggccatcgaa cgcttacatt cgggtcaagc    7200
acgttatcgg attgtactta agccgatttt ttaacctagg atcagtatct ggtaggagat    7260
cacggatgaa acgtgcagtg attactggcc tgggcattgt ttccagcatc ggtaataacc    7320
agcaggaagt cctggcatct ctgcgtgaag acgttcagg  gatcactttc tctcaggagc    7380
tgaaggattc cggcatgcgt agccacgtct ggggcaacgt aaaactggat accactggcc    7440
```

```
tcattgaccg caaagttgtg cgctttatga gcgacgcatc catttatgca ttcctttcta    7500
tggagcaggc aatcgctgat gcgggcctct ctccggaagc ttaccagaat aacccgcgcg    7560
ttggcctgat tgcaggttcc ggcggcggct ccccgcgttt ccaggtgttc ggcgctgacg    7620
caatgcgcgg cccgcgcggc ctgaaagcgg ttggcccgta tgtggtcacc aaagcgatgg    7680
catccggcgt ttctgcctgc ctcgccaccc cgtttaaaat tcatggcgtt aactactcca    7740
tcagctccgc gtgtgcgact tccgcacact gtatcggtaa cgcagtagag cagatccaac    7800
tgggcaaaca ggacatcgtg tttgctggcg gcggcgaaga gctgtgctgg gaaatggctt    7860
gcgaattcga cgcaatgggt gcgctgtcta ctaaatacaa cgacaccccg gaaaaagcct    7920
cccgtactta cgacgctcac cgtgacggtt tcgttatcgc tggcggcggc ggtatggtag    7980
tggttgaaga gctggaacac gcgctggcgc gtggtgctca catctatgct gaaatcgttg    8040
gctacggcgc aacctctgat ggtgcagaca tggttgctcc gtctggcgaa ggcgcagtac    8100
gctgcatgaa gatggcgatg catggcgttg atacccccaat cgattacctg aactcccacg    8160
gtacttcgac tccggttggc gacgtgaaag agctggcagc tatccgtgaa gtgttcggcg    8220
ataagagccc ggcgatttct gcaaccaaag ggatgaccgg tcactctctg ggcgctgctg    8280
gcgtacagga agctatctac tctctgctga tgctggaaca cggctttatc gccccgagca    8340
tcaacattga agagctggac gagcaggctg cgggtctgaa catcgtgacc gaaacgaccg    8400
atcgcgaact gaccaccgtt atgtctaaca gcttcggctt cggcggcacc aacgccacgc    8460
tggtaatgcg caagctgaaa gattaaattt aaatgctatg tctcgagaaa cggtctccag    8520
cttggctgtt ttggcggatg agagaagatt ttcagcctga tacagattaa atcagaacgc    8580
agaagcggtc tgataaaaca gaatttgcct ggcggcagta gcgcggtggt cccacctgac    8640
cccatgccga actcagaagt gaaacgccgt agcgccgatg gtagtgtggg gtctccccat    8700
gcgagagtag ggaactgcca ggcatcaaat aaaacgaaag gctcagtcga aagactgggc    8760
ctttcgtttt atctgttgtt tgtcggtgaa cgctctcctg acgccgatgc cggtattttc    8820
tccttacgca tctgtgcggt atttcacacc gcatatggtg cactctcagt acaatctgct    8880
ctgatgccgc atagttaagc cagccccgac acccgccaac acccgctgac gagcttagta    8940
aagccctcgc tagattttaa tgcggatgtt gcgattactt cgccaactat tgcgataaca    9000
agaaaaagcc agcctttcat gatatatctc ccaatttgtg tagggcttat tatgcacgct    9060
taaaaataat aaaagcagac ttgacctgat agtttggctg tgagcaatta tgtgcttagt    9120
gcatctaacg cttgagttaa gccgcgccgc gaagcggcgt cggcttgaac gaattgttag    9180
acattatttg ccgactacct tggtgatctc gcctttcacg tagtggacaa attcttccaa    9240
ctgatctgcg cgcgaggcca agcgatcttc ttcttgtcca agataagcct gtctagcttc    9300
aagtatgacg ggctgatact gggccggcag gcgctccatt gcccagtcgg cagcgacatc    9360
cttcggcgcg attttgccgg ttactgcgct gtaccaaatg cgggacaacg taagcactac    9420
atttcgctca tcgccagccc agtcgggcgg cgagttccat agcgttaagg tttcatttag    9480
cgcctcaaat agatcctgtt caggaaccgg atcaaagagt tcctccgccg ctggacctac    9540
caaggcaacg ctatgttctc ttgcttttgt cagcaagata gccagatcaa tgtcgatcgt    9600
ggctggctcg aagatacctg caagaatgtc attgcgctgc cattctccaa attgcagttc    9660
gcgcttagct ggataacgcc acggaatgat gtcgtcgtgc acaacaatgg tgacttctac    9720
agcgcggaga atctcgctct ctccagggga agccgaagtt tccaaaaggt cgttgatcaa    9780
agctcgccgc gttgtttcat caagccttac ggtcaccgta accagcaaat caatatcact    9840
```

```
gtgtggcttc aggccgccat ccactgcgga gccgtacaaa tgtacggcca gcaacgtcgg    9900
ttcgagatgg cgctcgatga cgccaactac ctctgatagt tgagtcgata cttcggcgat    9960
caccgcttcc ctcatgatgt ttaactttgt tttagggcga ctgccctgct gcgtaacatc   10020
gttgctgctc cataacatca aacatcgacc cacggcgtaa cgcgcttgct gcttggatgc   10080
ccgaggcata gactgtaccc caaaaaaaca gtcataacaa gcatgaaaaa ccgccactgc   10140
gccgttacca ccgctgcgtt cggtcaaggt tctggaccag ttgcgtgagc gcatacgcta   10200
cttgcattac agcttacgaa ccgaacaggc ttatgtccac tgggttcgtg ccttcatccg   10260
tttccacggt gtgcgtcacc cggcaacctt gggcagcagc gaagtcgagg catttctgtc   10320
ctggctggcg aacgagcgca aggtttcggt ctccacgcat cgtcaggcat tggcggcctt   10380
gctgttcttc tacggcaagg tgctgtgcac ggatctgccc tggcttcagg agatcggaag   10440
acctcggccg tcgcggcgct tgccggtggt gctgaccccg gatgaagtgg ttcgcatcct   10500
cggttttctg gaaggcgagc atcgtttgtt cgcccagctt ctgtatggaa cgggcatgcg   10560
gatcagtgag ggtttgcaac tgcgggtcaa ggatctggat ttcgatcacg gcacgatcat   10620
cgtgcgggga ggcaagggct ccaaggatcg ggccttgatg ttacccgaga gcttggcacc   10680
cagcctgcgc gagcagggga attaattccc acgggttttg ctgcccgcaa acgggctgtt   10740
ctggtgttgc tagtttgtta tcagaatcgc agatccggct tcagccggtt tgccggctga   10800
aagcgctatt tcttccagaa ttgccatgat ttttccca cgggaggcgt cactggctcc   10860
cgtgttgtcg gcagctttga ttcgataagc agcatcgcct gtttcaggct gtctatgtgt   10920
gactgttgag ctgtaacaag ttgtctcagg tgttcaattt catgttctag ttgctttgtt   10980
ttactggttt cacctgttct attaggtgtt acatgctgtt catctgttac attgtcgatc   11040
tgttcatggt gaacagcttt gaatgcacca aaaactcgta aaagctctga tgtatctatc   11100 tttttacac cgtttttcatc tgtgcatatg gacagttttc cctttgatat gtaacggtga   11160
acagttgttc tactttttgtt tgttagtctt gatgcttcac tgatagatac aagagccata   11220
agaacctcag atccttccgt atttagccag tatgttctct agtgtggttc gttgttttg   11280 cgtgagccat gagaacgaac cattgagatc atacttactt tgcatgtcac tcaaaaattt   11340
tgcctcaaaa ctggtgagct gaattttgc agttaaagca tcgtgtagtg ttttcttag   11400 tccgttatgt aggtaggaat ctgatgtaat ggttgttggt attttgtcac cattcatttt   11460
tatctggttg ttctcaagtt cggttacgag atccatttgt ctatctagtt caacttggaa   11520
aatcaacgta tcagtcgggc ggcctcgctt atcaaccacc aatttcatat tgctgtaagt   11580
gtttaaatct ttacttattg gtttcaaaac ccattggtta agccttttaa actcatggta   11640 gttatttttca agcattaaca tgaacttaaa ttcatcaagg ctaatctcta tatttgcctt   11700
gtgagttttc ttttgtgtta gttctttttaa taaccactca taaatcctca tagagtattt   11760
gttttcaaaa gacttaacat gttccagatt atattttatg aatttttta actggaaaag   11820 ataaggcaat atctcttcac taaaaactaa ttctaatttt tcgcttgaga acttggcata   11880
gtttgtccac tggaaaatct caaagccttt aaccaaagga ttcctgattt ccacagttct   11940
cgtcatcagc tctctggttg ctttagctaa tacaccataa gcattttccc tactgatgtt   12000
catcatctga gcgtattggt tataagtgaa cgataccgtc cgttctttcc ttgtagggtt   12060
ttcaatcgtg gggttgagta gtgccacaca gcataaaatt agcttggttt catgctccgt   12120
taagtcatag cgactaatcg ctagttcatt tgctttgaaa acaactaatt cagacataca   12180
```
tctcaattgg tctaggtgat tttaat                                          12206

<210> SEQ ID NO 23
<211> LENGTH: 14893
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
cactatacca attgagatgg gctagtcaat gataattact agtccttttc ctttgagttg        60
tgggtatctg taaattctgc tagacctttg ctggaaaact tgtaaattct gctagaccct       120
ctgtaaattc cgctagacct ttgtgtgttt tttttgttta tattcaagtg gttataattt       180
atagaataaa gaaagaataa aaaaagataa aagaataga tcccagccct gtgtataact        240
cactacttta gtcagttccg cagtattaca aaaggatgtc gcaaacgctg tttgctcctc       300
tacaaaacag accttaaaac cctaaaggcg tcggcatccg cttacagaca agctgtgacc       360
gtctccggga gctgcatgtg tcagaggttt tcaccgtcat caccgaaacg cgcgaggcag       420
cagatcaatt cgcgcgcgaa ggcgaagcgg catgcattta cgttgacacc atcgaatggt       480
gcaaaacctt tcgcggtatg gcatgatagc gcccggaaga gagtcaattc agggtggtga       540
atgtgaaacc agtaacgtta tacgatgtcg cagagtatgc cggtgtctct tatcagaccg       600
tttcccgcgt ggtgaaccag gccagccacg tttctgcgaa aacgcgggaa aaagtggaag       660
cggcgatggc ggagctgaat tacattccca accgcgtggc acaacaactg gcgggcaaac       720
agtcgttgct gattggcgtt gccacctcca gtctggccct gcacgcgccg tcgcaaattg       780
tcgcggcgat taaatctcgc gccgatcaac tgggtgccag cgtggtggtg tcgatggtag       840
aacgaagcgg cgtcgaagcc tgtaaagcgg cggtgcacaa tcttctcgcg caacgcgtca       900
gtgggctgat cattaactat ccgctggatg accaggatgc cattgctgtg gaagctgcct       960
gcactaatgt tccggcgtta tttcttgatg tctctgacca gacacccatc aacagtatta      1020
ttttctccca tgaagacggt acgcgactgg gcgtggagca tctggtcgca ttgggtcacc      1080
agcaaatcgc gctgttagcg ggcccattaa gttctgtctc ggcgcgtctg cgtctggctg      1140
gctggcataa atatctcact cgcaatcaaa ttcagccgat agcggaacgg gaaggcgact      1200
ggagtgccat gtccggtttt caacaaacca tgcaaatgct gaatgagggc atcgttccca      1260
ctgcgatgct ggttgccaac gatcagatgg cgctgggcgc aatgcgcgcc attaccgagt      1320
ccgggctgcg cgttggtgcg gatatctcgg tagtgggata cgacgatacc gaagacagct      1380
catgttatat cccgccgtta accaccatca aacaggattt tcgcctgctg ggcaaaccaa      1440
gcgtggaccg cttgctgcaa ctctctcagg gccaggcggt gaagggcaat cagctgttgc      1500
ccgtctcact ggtgaaaaga aaaccaccc tggcgcccaa tacgcaaacc gcctctcccc        1560
gcgcgttggc cgattcatta atgcagctgg cacgacaggt ttcccgactg gaaagcgggc      1620
agtgagcgca acgcaattaa tgtaagttag cgcgaattga tctggtttga cagcttatca      1680
tcgactgcac ggtgcaccaa tgcttctggc gtcaggcagc catcggaagc tgtggtatgg      1740
ctgtgcaggt cgtaaatcac tgcataattc gtgtcgctca aggcgcactc ccgttctgga      1800
taatgttttt tgcgccgaca tcataacggt tctggcaaat attctgaaat gagctgttga      1860
caattaatca tccggctcgt ataatgtgtg gaattgtgag cggataacaa tttcacacag      1920
gaaacagcgc cgctgagaaa aagcgaagcg gcactgctct taacaatttt atcagacaat      1980

```
ctgtgtgggc actcgaccgg aattatcgat taactttatt attaaaaatt aaagaggtat      2040
atattaatgt atcgattaaa taaggaggaa taaaccatga cgagcgatgt tcacgacgcg      2100
accgacggcg ttaccgagac tgcactggat gatgagcaga gcactcgtcg tattgcagaa      2160
ctgtacgcaa cggacccaga gttcgcagca gcagctcctc tgccggccgt tgtcgatgcg      2220
gcgcacaaac cgggcctgcg tctggcggaa atcctgcaga ccctgttcac cggctacggc      2280
gatcgtccgg cgctgggcta tcgtgcacgt gagctggcga cggacgaagg cggtcgtacg      2340
gtcacgcgtc tgctgccgcg cttcgatacc ctgacctatg cacaggtgtg gagccgtgtt      2400
caagcagtgg ctgcagcgtt gcgtcacaat ttcgcacaac cgatttaccc gggcgacgcg      2460
gtcgcgacta tcggctttgc gagcccggac tatttgacgc tggatctggt gtgcgcgtat      2520
ctgggcctgg tcagcgttcc tttgcagcat aacgctccgg tgtctcgcct ggccccgatt      2580
ctggccgagg tggaaccgcg tattctgacg gtgagcgcag aatacctgga cctggcggtt      2640
gaatccgtcc gtgatgtgaa ctccgtcagc cagctggttg ttttcgacca tcatccggaa      2700
gtggacgatc accgtgacgc actggctcgc gcacgcgagc agctggccgg caaaggtatc      2760
gcagttacga ccctggatgc gatcgcagac gaaggcgcag gtttgccggc tgagccgatt      2820
tacacggcgg atcacgatca gcgtctggcc atgattctgt ataccagcgg ctctacgggt      2880
gctccgaaag gcgcgatgta caccgaagcg atggtggctc gcctgtggac tatgagcttt      2940
atcacgggcg acccgacccc ggttatcaac gtgaacttca tgccgctgaa ccatctgggc      3000
ggtcgtatcc cgattagcac cgccgtgcag aatggcggta ccagctactt cgttccggaa      3060
agcgacatga gcacgctgtt tgaggatctg gccctggtcc gccctaccga actgggtctg      3120
gtgccgcgtg ttgcggacat gctgtaccag catcatctgg cgaccgtgga tcgcctggtg      3180
acccagggcg cggacgaact gactgcggaa aagcaggccg gtgcggaact gcgtgaacag      3240
gtcttgggcg tcgtgttat caccggtttt gtttccaccg cgccgttggc ggcagagatg      3300
cgtgcttttc tggatatcac cttgggtgca cacatcgttg acggttacgg tctgaccgaa      3360
accggtgcgg tcacccgtga tggtgtgatt gttcgtcctc cggtcattga ttacaagctg      3420
atcgatgtgc cggagctggg ttacttctcc accgacaaac cgtacccgcg tggcgagctg      3480
ctggttcgta gccaaacgtt gactccgggt tactacaagc gcccagaagt caccgcgtcc      3540
gttttcgatc gcgacggcta ttaccacacc ggcgacgtga tggcagaaac cgcgccagac      3600
cacctggtgt atgtggaccg ccgcaacaat gttctgaagc tggcgcaagg tgaatttgtc      3660
gccgtggcta acctggaggc cgttttcagc ggcgctgctc tggtccgcca gattttcgtg      3720
tatggtaaca gcgagcgcag ctttctgttg gctgttgttg tccctacccc ggaggcgctg      3780
gagcaatacg accctgccgc attgaaagca gccctggcgg attcgctgca gcgtacggcg      3840
cgtgatgccg agctgcagag ctatgaagtg ccggcggact tcattgttga gactgagcct      3900
tttagcgctg cgaacggtct gctgagcggt gttggcaagt gctgcgtcc gaatttgaag      3960 gatcgctacg gtcagcgttt ggagcagatg tacgcggaca tcgcggctac gcaggcgaac      4020
caattgcgtg aactgcgccg tgctgcggct actcaaccgg tgatcgacac gctgacgcaa      4080
gctgcggcga ccatcctggg taccggcagc gaggttgcaa gcgacgcaca ctttactgat      4140
ttgggcggtg attctctgag cgcgctgacg ttgagcaact tgctgtctga cttctttggc      4200
tttgaagtcc cggttggcac gattgttaac ccagcgacta atctggcaca gctggcgcaa      4260
catatcgagg cgcagcgcac ggcgggtgac cgccgtccat cctttacgac ggtccacggt      4320
```

```
gcggatgcta cggaaatccg tgcaagcgaa ctgactctgg acaaattcat cgacgctgag    4380
actctgcgcg cagcacctgg tttgccgaag gttacgactg agccgcgtac ggtcctgttg    4440
agcggtgcca atggttggtt gggccgcttc ctgaccctgc agtggctgga acgtttggca    4500
ccggttggcg gtaccctgat caccattgtg cgcggtcgtg acgatgcagc ggcacgtgca    4560
cgtttgactc aggcttacga tacggaccca gagctgtccc gccgcttcgc tgagttggcg    4620
gatcgccact tgcgtgtggt ggcaggtgat atcggcgatc cgaatctggg cctgaccccg    4680
gagatttggc accgtctggc agcagaggtc gatctggtcg ttcatccagc ggccctggtc    4740
aaccacgtcc tgccgtaccg ccagctgttt ggtccgaatg ttgttggcac cgccgaagtt    4800
atcaagttgg ctctgaccga gcgcatcaag cctgttacct acctgtccac ggttagcgtc    4860
gcgatgggta ttcctgattt tgaggaggac ggtgacattc gtaccgtcag cccggttcgt    4920
ccgctggatg gtggctatgc aaatggctat ggcaacagca gtgggctgg cgaggtgctg    4980
ctgcgcgagg cacatgacct gtgtggcctg ccggttgcga cgtttcgtag cgacatgatt    5040
ctggcccacc cgcgctaccg tggccaagtg aatgtgccgg acatgttcac ccgtctgctg    5100
ctgtccctgc tgatcacggg tgtggcaccg cgttccttct acattggtga tggcgagcgt    5160
ccgcgtgcac actacccggg cctgaccgtc gattttgttg cggaagcggt tactaccctg    5220
ggtgctcagc aacgtgaggg ttatgtctcg tatgacgtta tgaatccgca cgatgacggt    5280
attagcttgg atgtctttgt ggactggctg attcgtgcgg ccacccaat tgaccgtgtt    5340
gacgactatg atgactgggt gcgtcgtttt gaaaccgcgt tgaccgcctt gccggagaaa    5400
cgtcgtgcgc agaccgttct gccgctgctg catgcctttc gcgcgccaca ggcgccgttg    5460
cgtggcgccc ctgaaccgac cgaagtgttt catgcagcgg tgcgtaccgc taaagtcggt    5520
ccgggtgata ttccgcacct ggatgaagcc ctgatcgaca agtacatccg tgacctgcgc    5580
gagttcggtc tgatttagaa ttctttagcg ttaagaagga gatatatatg gcggacacgt    5640
tattgattct gggtgatagc ctgagcgccg ggtatcgaat gtctgccagc gcggcctggc    5700
ctgccttgtt gaatgataag tggcagagta aaacgtcggt agttaatgcc agcatcagcg    5760
gcgacacctc gcaacaagga ctggcgcgcc ttccggctct gctgaaacag catcagccgc    5820
gttgggtgct ggttgaactg ggcggcaatg acggtttgcg tggttttcag ccacagcaaa    5880
ccgagcaaac gctgcgccag attttgcagg atgtcaaagc cgccaacgct gaaccattgt    5940
taatgcaaat acgtctgcct tacaactatg gtcgtcgtta taatgaagcc tttagcgcca    6000
tttaccccaa actcgccaaa gagtttgatg ttccgctgct gcccttttt atggaagagg    6060
tctgcctcaa gccacaatgg atgcaggatg acggtattca tcccaaccgc gacgcccagc    6120
cgtttattgc cgactggatg gcgaagcagt tgcagccttt agtaaatcat gactcataag    6180
cttctaagga aataatagga gattgaaaat ggcaacaact aatgtgattc atgcttatgc    6240
tgcaatgcag gcaggtgaag cactcgtgcc ttattcgttt gatgcaggcg aactgcaacc    6300
acatcaggtt gaagttaaag tcgaatattg tgggctgtgc cattccgatg tctcggtact    6360
caacaacgaa tggcattctt cggtttatcc agtcgtggca ggtcatgaag tgattggtac    6420
gattacccaa ctgggaagtg aagccaaagg actaaaaatt ggtcaacgtg ttggtattgg    6480
ctggacggca gaaagctgtc aggcctgtga ccaatgcatc agtggtcagc aggtattgtg    6540
cacgggcgaa ataccgcaa ctattattgg tcatgctggt ggctttgcag ataaggttcg    6600
tgcaggctgg caatgggtca ttcccctgcc cgacgaactc gatccgacca gtgctggtcc    6660
tttgctgtgt ggcggaatca cagtatttga tccaatttta aaacatcaga ttcaggctat    6720
```

```
tcatcatgtt gctgtgattg gtatcggtgg tttgggacat atggccatca agctacttaa    6780
agcatggggc tgtgaaatta ctgcgtttag ttcaaatcca acaaaaccg atgagctcaa     6840 agctatgggg gccgatcacg tggtcaatag ccgtgatgat gccgaaatta atcgcaaca    6900 gggtaaattt gatttactgc tgagtacagt taatgtgcct ttaaactgga atgcgtatct    6960
aaacacactg gcacccaatg gcactttcca ttttttgggc gtggtgatgg aaccaatccc    7020
tgtacctgtc ggtgcgctgc taggaggtgc caaatcgcta acagcatcac caactggctc    7080
gcctgctgcc ttacgtaagc tgctcgaatt tgcggcacgt aagaatatcg cacctcaaat    7140
cgagatgtat cctatgtcgg agctgaatga ggccatcgaa cgcttacatt cgggtcaagc    7200
acgttatcgg attgtactta agccgatttt ttaacctagg atcagtatct ggtaggagat    7260
cacggatgaa acgtgcagtg attactggcc tgggcattgt ttccagcatc ggtaataacc    7320
agcaggaagt cctggcatct ctgcgtgaag gacgttcagg gatcactttc tctcaggagc    7380
tgaaggattc cggcatgcgt agccacgtct ggggcaacgt aaaactggat accactggcc    7440
tcattgaccg caaagttgtg cgctttatga gcgacgcatc catttatgca ttcctttcta    7500
tggagcagga aatcgctgat gcgggcctct ctccggaagc ttaccagaat aacccgcgcg    7560
ttggcctgat tgcaggttcc ggcggcggct ccccgcgttt ccaggtgttc ggcgctgacg    7620
caatgcgcgg cccgcgcggc ctgaaagcgg ttggcccgta tgtggtcacc aaagcgatgg    7680
catccggcgt ttctgcctgc ctcgccaccc cgtttaaaat tcatggcgtt aactactcca    7740
tcagctccgc gtgtgcgact tccgcacact gtatcggtaa cgcagtagag cagatccaac    7800
tgggcaaaca ggacatcgtg tttgctggcg gcggcgaaga gctgtgctgg gaaatggctt    7860
gcgaattcga cgcaatgggt gcgctgtcta ctaaatacaa cgacaccccg gaaaaagcct    7920
cccgtactta cgacgctcac cgtgacggtt tcgttatcgc tggcggcggc ggtatggtag    7980
tggttgaaga gctggaacac gcgctggcgc gtggtgctca catctatgct gaaatcgttg    8040
gctacggcgc aacctctgat ggtgcagaca tggttgctcc gtctggcgaa ggcgcagtac    8100
gctgcatgaa gatggcgatg catggcgttg atacccccaat cgattacctg aactcccacg    8160
gtacttcgac tccggttggc gacgtgaaag agctggcagc tatccgtgaa gtgttcggcg    8220
ataagagccc ggcgatttct gcaaccaaag ggatgaccgg tcactctctg ggcgctgctg    8280
gcgtacagga agctatctac tctctgctga tgctggaaca cggctttatc gccccgagca    8340
tcaacattga agagctggac gagcaggctg cgggtctgaa catcgtgacc gaaacgaccg    8400
atcgcgaact gaccaccgtt atgtctaaca gcttcggctt cggcggcacc aacgccacgc    8460
tggtaatgcg caagctgaaa gattaaattt ctaaaattca gttaggaggt atttgatggt    8520
cattaaggcc caaagcccgg cgggtttcgc ggaagagtac attattgaaa gtatctggaa    8580
taaccgcttc cctcccggga ctattttgcc cgcagaacgt gaactttcag aattaattgg    8640
cgtaacgcgt actacgttac gtgaagtgtt acagcgtctg gcacgagatg gctggttgac    8700
cattcaacat ggcaagccga cgaaggtgaa taatttctgg gaaacttccg gtttaaatat    8760
ccttgaaaca ctggcgcgac tggatcacga agtgtgccg cagcttattg ataatttgct    8820
gtcggtgcgt accaatattt ccactatttt tattcgcacc gcgtttcgtc agcatcccga    8880
taaagcgcag gaagtgctgg ctaccgctaa tgaagtggcc gatcacgccg atgcctttgc    8940
cgagctggat tacaacatat tccgcggcct ggcgtttgct tccggcaacc cgatttacgg    9000
tctgattctt aacggggatga aagggctgta tacgcgtatt ggtcgtcact atttcgccaa    9060
```

```
tccggaagcg cgcagtctgg cgctgggctt ctaccacaaa ctgtcggcgt tgtgcagtga    9120
aggcgcgcac gatcaggtgt acgaaacagt gcgtcgctat gggcatgaga gtggcgagat    9180
ttggcaccgg atgcagaaaa atctgccggg tgatttagcc attcaggggc gataactcga    9240
ggatggtagt gtggggtctc cccatgcgag agtagggaac tgccaggcat caaataaaac    9300
gaaaggctca gtcgaaagac tgggcctttc gttttatctg ttgtttgtcg gtgaacgctc    9360
tcctgagtag gacaaatccg ccgggagcgg atttgaacgt tgcgaagcaa cggcccggag    9420
ggtggcgggc aggacgcccg ccataaactg ccaggcatca aattaagcag aaggccatcc    9480
tgacggatgg cctttttgcg tggccagtgc caagcttgca tgcagattgc agcattacac    9540
gtcttgagcg attgtgtagg ctggagctgc ttcgaagttc ctatactttc tagagaatag    9600
gaacttcgga ataggaactt caagatcccc ttattagaag aactcgtcaa gaaggcgata    9660
gaaggcgatg cgctgcgaat cgggagcggc gataccgtaa agcacgagga agcggtcagc    9720
ccattcgccg ccaagctctt cagcaatatc acgggtagcc aacgctatgt cctgatagcg    9780
gtccgccaca cccagccggc cacagtcgat gaatccagaa aagcggccat tttccaccat    9840
gatattcggc aagcaggcat cgccatgggt cacgacgaga tcctcgccgt cgggcatgcg    9900
cgccttgagc ctggcgaaca gttcggctgg cgcgagcccc tgatgctctt cgtccagatc    9960
atcctgatcg acaagaccgg cttccatccg agtacgtgct cgctcgatgc gatgtttcgc   10020
ttggtggtcg aatgggcagg tagccggatc aagcgtatgc agccgccgca ttgcatcagc   10080
catgatggat actttctcgg caggagcaag gtgagatgac aggagatcct gccccggcac   10140
ttcgcccaat agcagccagt cccttcccgc ttcagtgaca acgtcgagca cagctgcgca   10200
aggaacgccc gtcgtggcca gccacgatag ccgcgctgcc tcgtcctgca gttcattcag   10260
ggcaccggac aggtcggtct tgacaaaaag aaccgggcgc ccctgcgctg acagccggaa   10320
cacggcggca tcagagcagc cgattgtctg ttgtgcccag tcatagccga atagcctctc   10380
cacccaagcg gccggagaac ctgcgtgcaa tccatcttgt tcaatcatgc gaaacgatcc   10440
tcatcctgtc tcttgatcag atcttgatcc cctgcgccat cagatccttg gcggcaagaa   10500
agccatccag tttactttgc agggcttccc aaccttacca gagggcgccc cagctggcaa   10560
ttccggttcg cttgctgtcc ataaaaccgc ccagtctagc tatcgccatg taagcccact   10620
gcaagctacc tgctttctct ttgcgcttgc gttttccctt gtccagatag cccagtagct   10680
gacattcatc cggggtcagc accgtttctg cggactggct ttctacgtgt tccgcttcct   10740
ttagcagccc ttgcgccctg agtgcttgcg gcagcgtgag cttcaaaagc gctctgaagt   10800
tcctatactt tctagagaat aggaacttcg aactgcaggt cgacggatcc ccggaattaa   10860
ttctcatgtt tgacagctta tcactgatca gtgaattaat ggcgatgacg catcctcacg   10920
ataatatccg ggtaggcgca atcactttcg tctctactcc gttacaaagc gaggctgggt   10980
atttcccggc ctttctgtta tccgaaatcc actgaaagca cagcggctgg ctgaggagat   11040
aaataataaa cgagggggctg tatgcacaaa gcatcttctg ttgagttaag aacgagtatc   11100
gagatggcac atagccttgc tcaaattgga atcaggtttg tgccaatacc agtagaaaca   11160
gacgaagctc gagcgtatca tatttaaatt cgagaaacgg tctccagctt ggctgttttg   11220
gcggatgaga gaagattttc agcctgatac agattaaatc agaacgcaga agcggtctga   11280
taaaacagaa tttgcctggc ggcagtagcg cggtggtccc acctgacccc atgccgaact   11340
cagaagtgaa acgccgtagc gccgatggta gtgtggggtc tccccatgcg agagtaggga   11400
actgccaggc atcaaataaa acgaaaggct cagtcgaaag actgggcctt tcgttttatc   11460
```

```
tgttgtttgt cggtgaacgc tctcctgacg cctgatgcgg tattttctcc ttacgcatct    11520
gtgcggtatt tcacaccgca tatggtgcac tctcagtaca atctgctctg atgccgcata    11580
gttaagccag ccccgacacc cgccaacacc cgctgacgag cttagtaaag ccctcgctag    11640
attttaatgc ggatgttgcg attacttcgc caactattgc gataacaaga aaaagccagc    11700
ctttcatgat atatctccca atttgtgtag ggcttattat gcacgcttaa aaataataaa    11760
agcagacttg acctgatagt ttggctgtga gcaattatgt gcttagtgca tctaacgctt    11820
gagttaagcc gcgccgcgaa gcggcgtcgg cttgaacgaa ttgttagaca ttatttgccg    11880
actaccttgg tgatctcgcc tttcacgtag tggacaaatt cttccaactg atctgcgcgc    11940
gaggccaagc gatcttcttc ttgtccaaga taagcctgtc tagcttcaag tatgacgggc    12000
tgatactggg ccggcaggcg ctccattgcc cagtcggcag cgacatcctt cggcgcgatt    12060
ttgccggtta ctgcgctgta ccaaatgcgg gacaacgtaa gcactacatt tcgctcatcg    12120
ccagcccagt cgggcggcga gttccatagc gttaaggttt catttagcgc ctcaaataga    12180
tcctgttcag gaaccggatc aaagagttcc tccgccgctg gacctaccaa ggcaacgcta    12240
tgttctcttg cttttgtcag caagatagcc agatcaatgt cgatcgtggc tggctcgaag    12300
atacctgcaa gaatgtcatt gcgctgccat tctccaaatt gcagttcgcg cttagctgga    12360
taacgccacg gaatgatgtc gtcgtgcaca acaatggtga cttctacagc gcggagaatc    12420
tcgctctctc caggggaagc cgaagtttcc aaaaggtcgt tgatcaaagc tcgccgcgtt    12480
gtttcatcaa gccttacggt caccgtaacc agcaaatcaa tatcactgtg tggcttcagg    12540
ccgccatcca ctgcggagcc gtacaaatgt acggccagca acgtcggttc gagatggcgc    12600
tcgatgacgc caactacctc tgatagttga gtcgatactt cggcgatcac cgcttccctc    12660
atgatgttta actttgtttt agggcgactg ccctgctgcg taacatcgtt gctgctccat    12720
aacatcaaac atcgacccac ggcgtaacgc gcttgctgct tggatgcccg aggcatagac    12780
tgtaccccaa aaaacagtc ataacaagcc atgaaaaccg ccactgcgcc gttaccaccg    12840
ctgcgttcgg tcaaggttct ggaccagttg cgtgagcgca tacgctactt gcattacagc    12900
ttacgaaccg aacaggctta tgtccactgg gttcgtgcct tcatccgttt ccacggtgtg    12960
cgtcacccgg caaccttggg cagcagcgaa gtcgaggcat ttctgtcctg gctggcgaac    13020
gagcgcaagg tttcggtctc cacgcatcgt caggcattgg cggccttgct gttcttctac    13080
ggcaaggtgc tgtgcacgga tctgccctgg cttcaggaga tcggaagacc tcggccgtcg    13140
cggcgcttgc cggtggtgct gaccccggat gaagtggttc gcatcctcgg ttttctggaa    13200
ggcgagcatc gtttgttcgc ccagcttctg tatggaacgg gcatgcggat cagtgagggt    13260
ttgcaactgc gggtcaagga tctggatttc gatcacggca cgatcatcgt gcgggagggc    13320
aagggctcca aggatcgggc cttgatgtta cccgagagct ggcacccag cctgcgcgag    13380
caggggaatt aattcccacg ggttttgctg cccgcaaacg ggctgttctg tgttgctag     13440
tttgttatca gaatcgcaga tccggcttca gccggtttgc cggctgaaag cgctatttct    13500
tccagaattg ccatgatttt ttccccacgg gaggcgtcac tggctcccgt gttgtcggca    13560
gctttgattc gataagcagc atcgcctgtt tcaggctgtc tatgtgtgac tgttgagctg    13620
taacaagttg tctcaggtgt tcaatttcat gttctagttg cttkgttttta ctggtttcac    13680
ctgttctatt aggtgttaca tgctgttcat ctgttacatt gtcgatctgt tcatggtgaa    13740
cagctttgaa tgcaccaaaa actcgtaaaa gctctgatgt atctatcttt tttacaccgt    13800
```

```
tttcatctgt gcatatggac agttttccct ttgatatgta acggtgaaca gttgttctac  13860
ttttgtttgt tagtcttgat gcttcactga tagataacaag agccataaga acctcagatc  13920
cttccgtatt tagccagtat gttctctagt gtggttcgtt gttttttgcgt gagccatgag  13980 aacgaaccat tgagatcata cttactttgc atgtcactca aaaattttgc ctcaaaactg  14040
gtgagctgaa tttttgcagt taaagcatcg tgtagtgttt ttcttagtcc gttatgtagg  14100
taggaatctg atgtaatggt tgttggtatt ttgtcaccat tcatttttat ctggttgttc  14160
tcaagttcgg ttacgagatc catttgtcta tctagttcaa cttggaaaat caacgtatca  14220
gtcgggcggc ctcgcttatc aaccaccaat ttcatattgc tgtaagtgtt taaatcttta  14280
cttattggtt tcaaaaccca ttggttaagc cttttaaact catggtagtt attttcaagc  14340
attaacatga acttaaattc atcaaggcta atctctatat ttgccttgtg agttttcttt  14400
tgtgttagtt cttttaataa ccactcataa atcctcatag agtatttgtt ttcaaaagac  14460
ttaacatgtt ccagattata ttttatgaat ttttttaact ggaaaagata aggcaatatc  14520
tcttcactaa aaactaattc taattttttcg cttgagaact tggcatagtt tgtccactgg  14580
aaaatctcaa agcctttaac caaaggattc ctgatttcca cagttctcgt catcagctct  14640
ctggttgctt tagctaatac accataagca ttttccctac tgatgttcat catctgagcg  14700
tattggttat aagtgaacga taccgtccgt tctttccttg tagggttttc aatcgtgggg  14760
ttgagtagtg ccacacagca taaaattagc ttggtttcat gctccgttaa gtcatagcga  14820
ctaatcgcta gttcatttgc tttgaaaaca actaattcag acatacatct caattggtct  14880
aggtgatttt aat                                                      14893
```

METHODS AND COMPOSITIONS FOR IMPROVED PRODUCTION OF FATTY ACIDS AND DERIVATIVES THEREOF

CROSS-REFERENCE TO RELATED APPLICATIONS

This application claims priority benefit to U.S. Application Ser. No. 61/470,989, filed Apr. 1, 2011, which is expressly incorporated by reference herein in its entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 28, 2012, is named LS034PCT.txt and is 104,756 bytes in size.

BACKGROUND OF THE INVENTION

Crude petroleum is a limited, natural resource found in the Earth in liquid, gaseous, and solid forms. Although crude petroleum is a valuable resource, it is discovered and extracted from the Earth at considerable financial and environmental costs. Moreover, in its natural form, crude petroleum extracted from the Earth has few commercial uses. Crude petroleum is a mixture of hydrocarbons (e.g., paraffins (or alkanes), olefins (or alkenes), alkynes, napthenes (or cycloalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.). Hence, crude petroleum must be refined and purified at considerable cost before it can be used commercially.

Crude petroleum is also a primary source of raw materials for producing petrochemicals. The two main classes of raw materials derived from petroleum are short chain olefins (e.g., ethylene and propylene) and aromatics (e.g., benzene and xylene isomers). These raw materials are derived from longer chain hydrocarbons in crude petroleum by cracking it at considerable expense using a variety of methods, such as catalytic cracking, steam cracking, or catalytic reforming. These raw materials can be used to make petrochemicals such as monomers, solvents, detergents, and adhesives, which otherwise cannot be directly refined from crude petroleum.

Petrochemicals, in turn, can be used to make specialty chemicals, such as plastics, resins, fibers, elastomers, pharmaceuticals, lubricants, and gels. Particular specialty chemicals that can be produced from petrochemical raw materials include fatty acids, hydrocarbons (e.g., long chain, branched chain, saturated, unsaturated, etc.), fatty aldehydes, fatty alcohols, esters, ketones, lubricants, etc.

Due to the inherent challenges posed by petroleum, there is a need for a renewable petroleum source that does not need to be explored, extracted, transported over long distances, or substantially refined like crude petroleum. There is also a need for a renewable petroleum source which can be produced economically without creating the type of environmental damage produced by the petroleum industry and the burning of petroleum-based fuels. For similar reasons, there is also a need for a renewable source of chemicals which are typically derived from petroleum.

One method of producing renewable petroleum is by engineering microorganisms to produce renewable petroleum products. Some microorganisms have long been known to possess a natural ability to produce petroleum products (e.g., yeast to produce ethanol). More recently, the development of advanced biotechnologies has made it possible to metabolically engineer an organism to produce bioproducts and biofuels. Bioproducts (e.g., chemicals) and biofuels (e.g., biodiesel) are renewable alternatives to petroleum-based chemicals and fuels, respectively. Bioproducts and biofuels can be derived from renewable sources, such as plant matter, animal matter, and organic waste matter, which are collectively known as biomass.

Biofuels can be substituted for any petroleum-based fuel (e.g., gasoline, diesel, aviation fuel, heating oil, etc.), and offer several advantages over petroleum-based fuels. Biofuels do not require expensive and risky exploration or extraction. Biofuels can be produced locally and therefore do not require transportation over long distances. In addition, biofuels can be made directly and require little or no additional refining. Furthermore, the combustion of biofuels causes less of a burden on the environment since the amount of harmful emissions (e.g., green house gases, air pollution, etc.) released during combustion is reduced as compared to the combustion of petroleum-based fuels. Moreover, biofuels maintain a balanced carbon cycle because biofuels are produced from biomass, a renewable, natural resource. Although combustion of biofuels releases carbon (e.g., as carbon dioxide), this carbon will be recycled during the production of biomass (e.g., the cultivation of crops), thereby balancing the carbon cycle, which is not achieved with the use of petroleum based fuels.

Biologically derived chemicals offer similar advantages over petrochemicals that biofuels offer over petroleum-based fuels. In particular, biologically derived chemicals can be converted from biomass to the desired chemical product directly without extensive refining, unlike petrochemicals, which must be produced by refining crude petroleum to recover raw materials which are then processed further into the desired petrochemical.

Hydrocarbons have many commercial uses. For example, shorter chain alkanes are used as fuels. Methane and ethane are the main constituents of natural gas. Longer chain alkanes (e.g., from five to sixteen carbons) are used as transportation fuels (e.g., gasoline, diesel, or aviation fuel). Alkanes having more than sixteen carbon atoms are important components of fuel oils and lubricating oils. Even longer alkanes, which are solid at room temperature, can be used, for example, as a paraffin wax. Alkanes that contain approximately thirty-five carbons are found in bitumen, which is used for road surfacing. In addition, longer chain alkanes can be cracked to produce commercially useful shorter chain hydrocarbons.

Like short chain alkanes, short chain alkenes are used in transportation fuels. Longer chain alkenes are used in plastics, lubricants, and synthetic lubricants. In addition, alkenes are used as a feedstock to produce alcohols, esters, plasticizers, surfactants, tertiary amines, enhanced oil recovery agents, fatty acids, thiols, alkenylsuccinic anhydrides, epoxides, chlorinated alkanes, chlorinated alkenes, waxes, fuel additives, and drag flow reducers.

Esters have many commercial uses. For example, biodiesel, an alternative fuel, is comprised of esters (e.g., fatty acid methyl ester, fatty acid ethyl esters, etc.). Some low molecular weight esters are volatile with a pleasant odor which makes them useful as fragrances or flavoring agents. In addition, esters are used as solvents for lacquers, paints, and varnishes. Furthermore, some naturally occurring substances, such as waxes, fats, and oils are comprised of esters. Esters are also used as softening agents in resins and plastics, plasticizers, flame retardants, and additives in gasoline and oil. In addition, esters can be used in the manufacture of polymers, films, textiles, dyes, and pharmaceuticals.

Aldehydes are used to produce many specialty chemicals. For example, aldehydes are used to produce polymers, resins (e.g., Bakelite), dyes, flavorings, plasticizers, perfumes, pharmaceuticals, and other chemicals, some of which may be used as solvents, preservatives, or disinfectants. In addition, certain natural and synthetic compounds, such as vitamins and hormones, are aldehydes, and many sugars contain aldehyde groups. Fatty aldehydes can be converted to fatty alcohols by chemical or enzymatic reduction.

Fatty alcohols have many commercial uses. Worldwide annual sales of fatty alcohols and their derivatives are in excess of U.S. $1 billion. The shorter chain fatty alcohols are used in the cosmetic and food industries as emulsifiers, emollients, and thickeners. Due to their amphiphilic nature, fatty alcohols behave as nonionic surfactants, which are useful in personal care and household products, such as, for example, detergents. In addition, fatty alcohols are used in waxes, gums, resins, pharmaceutical salves and lotions, lubricating oil additives, textile antistatic and finishing agents, plasticizers, cosmetics, industrial solvents, and solvents for fats.

Acyl-CoA synthase (ACS) esterifies free fatty acids to acyl-CoA by a two-step mechanism. The free fatty acid first is converted to an acyl-AMP intermediate (an adenylate) through the pyrophosphorolysis of ATP. The activated carbonyl carbon of the adenylate is then coupled to the thiol group of CoA, releasing AMP and the acyl-CoA final product (Shockey et al., Plant. Physiol., 129: 1710-1722 (2002)).

FadR is a key regulatory factor involved in fatty acid degradation and fatty acid biosynthesis pathways (Cronan et al., Mol. Microbiol, 29(4): 937-943 (1998)). The E. coli ACS enzyme FadD and the fatty acid transport protein FadL are essential components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which can bind to the transcription factor FadR and derepress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products (Caviglia et al., J. Biol. Chem., 279(12): 1163-1169 (2004)).

There remains a need for methods and compositions for enhancing the production of biologically derived chemicals, such as fatty acids and fatty acid derivatives. This invention provides such methods and compositions. The invention further provides products derived from the fatty acids and derivatives thereof produced by the methods described herein, such as fuels, surfactants, and detergents.

BRIEF SUMMARY OF THE INVENTION

The invention provides improved methods of producing a fatty acid or a fatty acid derivative in a host cell. The method comprises (a) providing a host cell which is genetically engineered to have an altered level of expression of a FadR polypeptide as compared to the level of expression of the FadR polypeptide in a corresponding wild-type host cell, (b) culturing the engineered host cell in a culture medium under conditions permissive for the production of a fatty acid or a fatty acid derivative, and (c) isolating the fatty acid or fatty acid derivative from the engineered host cell. As a result of this method, one or more of the titer, yield, or productivity of the fatty acid or fatty acid derivative produced by the engineered host cell is increased relative to that of the corresponding wild-type host cell.

Also provided are fatty acids and fatty acid derivatives, such as an acyl-CoA, a fatty aldehyde, a short chain alcohol, a long chain alcohol, a fatty alcohol, a hydrocarbon, or an ester, produced by the methods of the invention. Further provided are biofuel compositions and surfactant compositions comprising a fatty acid or a fatty acid derivative produced by the methods of the invention.

BRIEF DESCRIPTION OF THE SEVERAL VIEWS OF THE DRAWING(S)

FIG. 1 is a chart of exemplary genes suitable for use in practicing the invention. Polypeptide and/or polynucleotide accession numbers are from the National Center for Biotechnology Information (NCBI) database, and enzyme EC numbers are from the Nomenclature Committee of the International Union of Biochemistry and Molecular Biology (NC-IUBMB).

Figure 7:
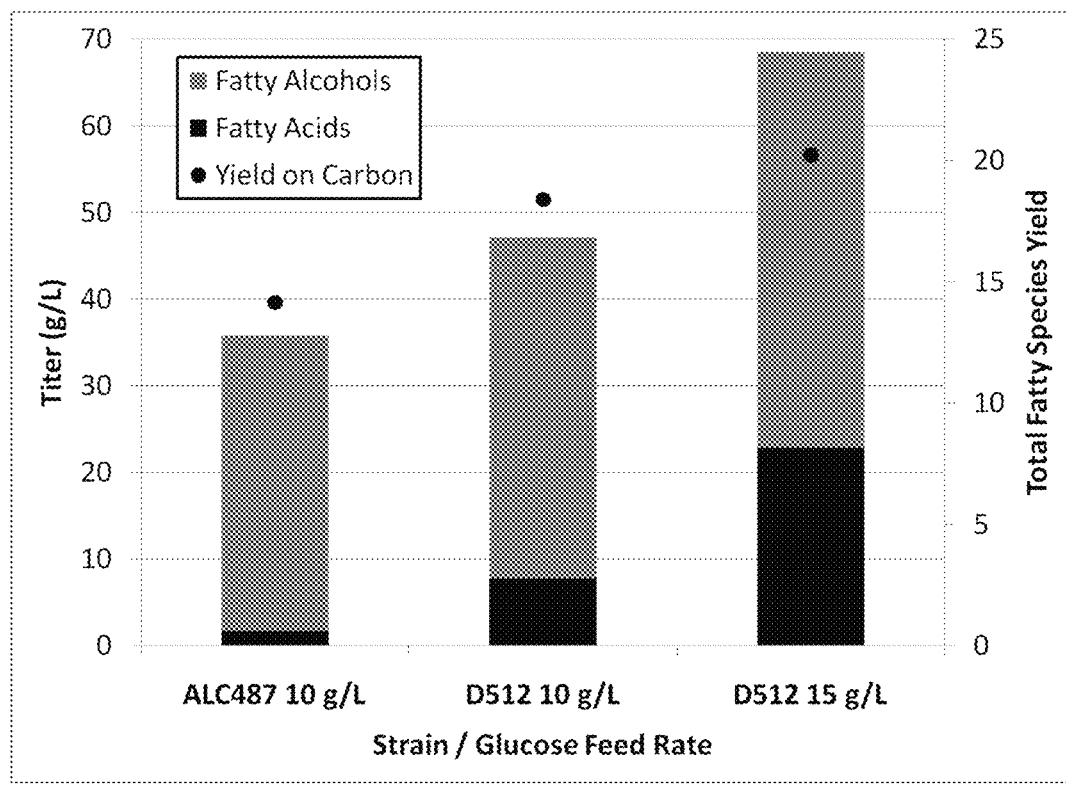

FIG. 7 is a graph of fatty acid and fatty alcohol production and total fatty species yield in 5 L bioreactor fermentations of the control ALC487 strain fed at a glucose rate of 10 g/L/hr or the D512 strain having altered expression of wild-type FadR fed at a glucose rate of 10 g/L/hr or 15 g/L/hr. The bars represent fatty alcohol or fatty acid titer, and the circles represent total fatty species yield on carbon.

Figure 8:
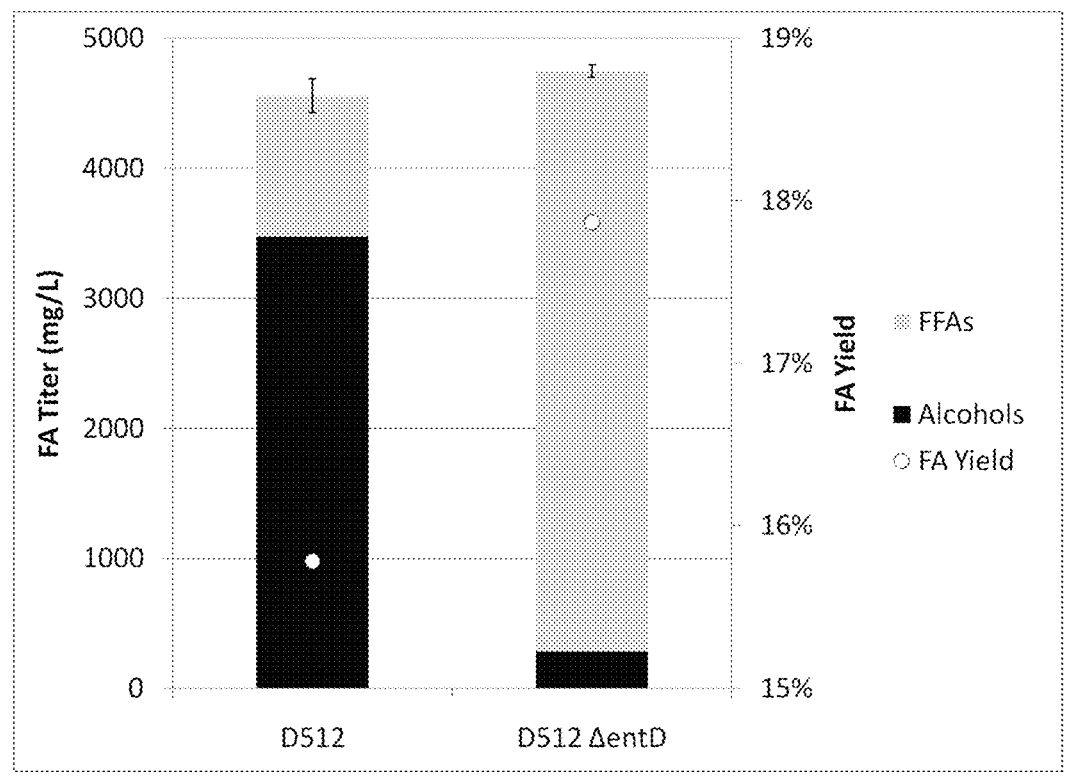

FIG. 8 is a graph of fatty acid and fatty alcohol production and total fatty species yield in shake flask fermentations of the D512 strain or a D512 strain in which the entD gene was deleted. The bars represent fatty acid or fatty alcohol titer, and the circles represent fatty acid yield.

Figure 9:
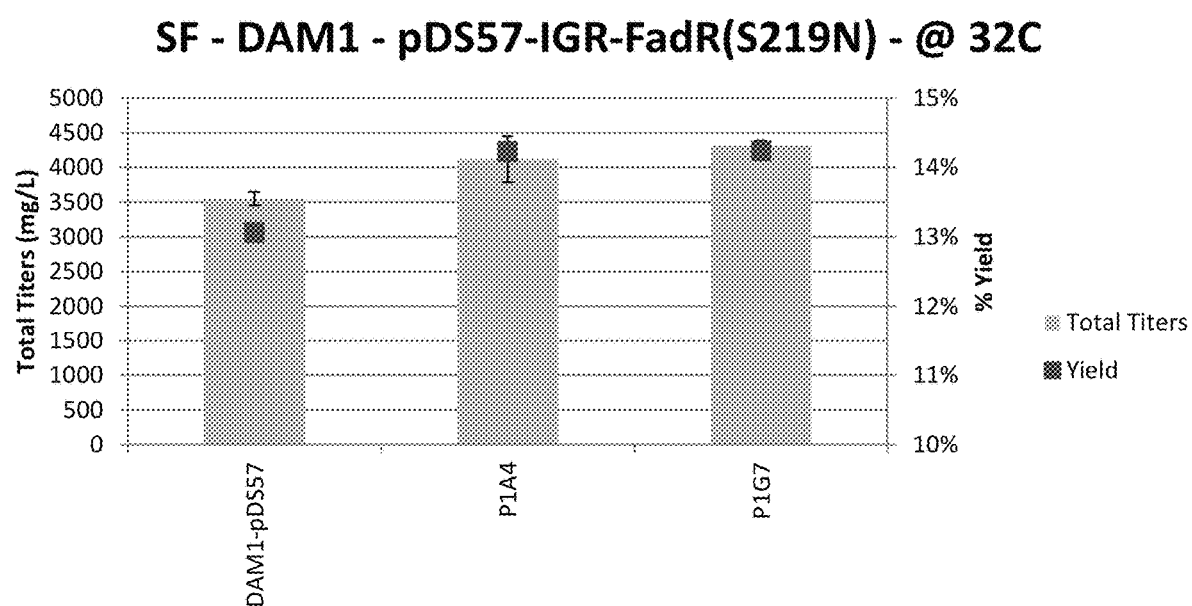

FIG. 9 is a graph of total fatty species (fatty acids and fatty acid methyl ester (FAME)) titers and yields in two ribosome binding site (RBS) library E. coli strains having altered expression of mutant FadR[S219N] (i.e., P1A4 and P1G7) as compared to the total fatty species titers and yields in the parental E. coli strain (DAM1-pDS57) in shake flask (SF) fermentations at 32° C. The bars represent total fatty species titers after 56 hours of culture, and the squares represent total fatty species yield after 56 hours of culture.

Figure 10:
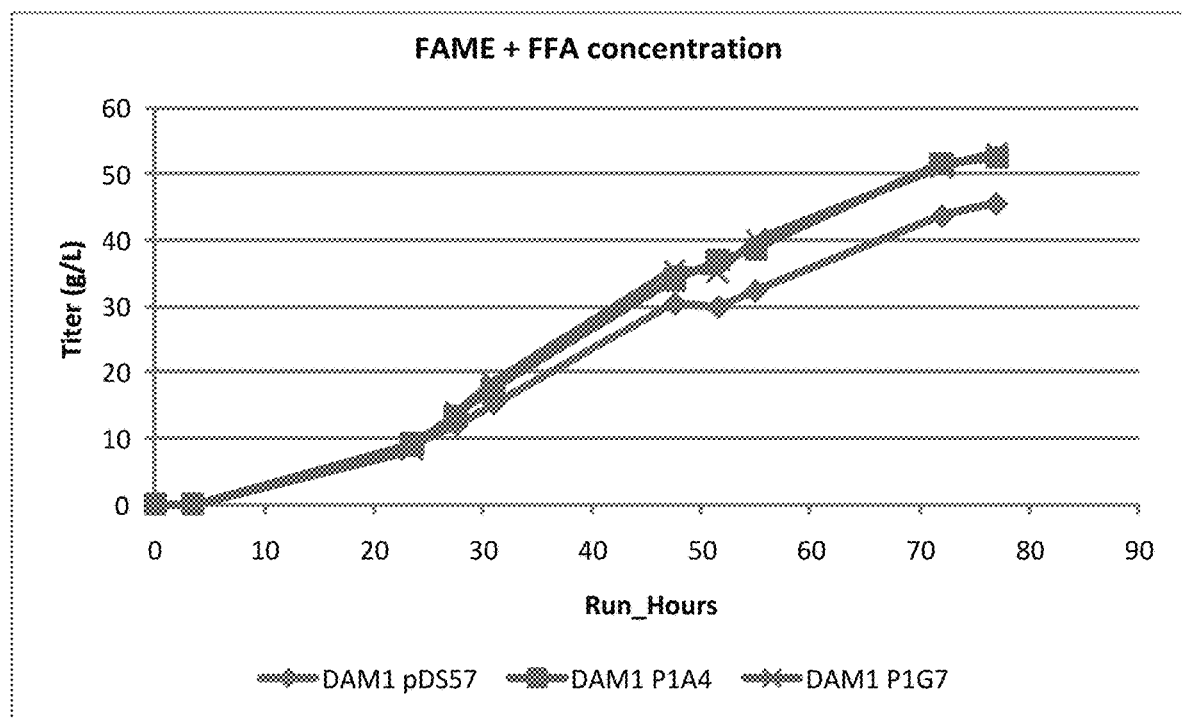

FIG. 10 is a line graph of combined FAME and free fatty acid (FFA) titers in the parental DAM1 pDS57 strain, or RBS library strains P1A4 or P1G7 in bioreactor fermentations at several timepoints following induction of FAME and FFA production, wherein DAM1 P1A4 and DAM1 P1G7 express FadR and DAM1 pDS57 does not express FadR.

Figure 11:
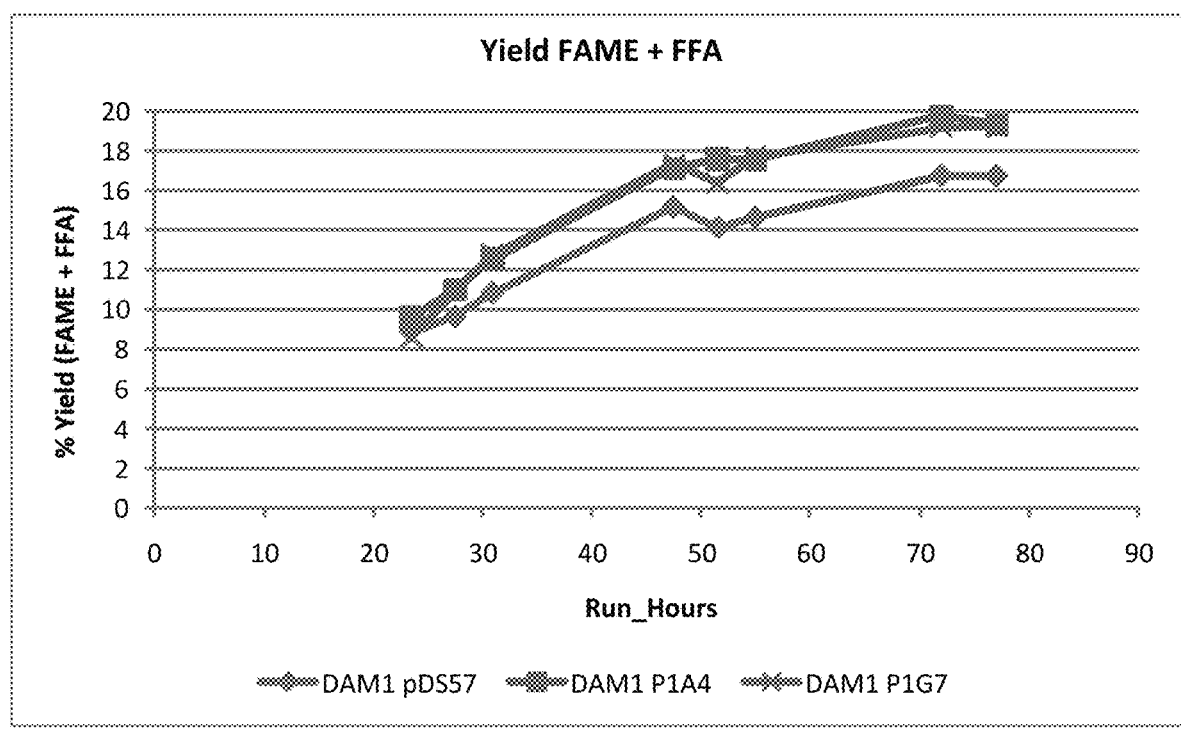

FIG. 11 is a line graph of combined FAME and FFA yields in the parental DAM1 pDS57 strain, or RBS library strains P1A4 or P1G7 in bioreactor fermentations at several time points following induction of FAME and FFA production, wherein DAM1 P1A4 and DAM1 P1G7 express FadR and DAM1 pDS57 does not express FadR.

DETAILED DESCRIPTION OF THE INVENTION

The invention is based, at least in part, on the discovery that altering the level of expression of FadR in a host cell facilitates enhanced production of fatty acids and fatty acid derivatives by the host cell.

The invention provides improved methods of producing a fatty acid or a fatty acid derivative in a host cell. The method comprises (a) providing a host cell which is genetically engineered to have an altered level of expression of a FadR polypeptide as compared to the level of expression of the FadR polypeptide in a corresponding wild-type host cell, (b) culturing the engineered host cell in a culture medium under conditions permissive for the production of a fatty acid or a fatty acid derivative, and (c) isolating the fatty acid or fatty acid derivative from the engineered host cell. As a result of this method, one or more of the titer, yield, or productivity of the fatty acid or fatty acid derivative produced by the engineered host cell is increased relative to that of the corresponding wild-type host cell.

DEFINITIONS

As used in this specification and the appended claims, the singular forms "a," "an" and "the" include plural referents unless the context clearly dictates otherwise. Thus, for example, reference to "a recombinant host cell" includes two or more such recombinant host cells, reference to "a fatty alcohol" includes one or more fatty alcohols, or mixtures of fatty alcohols, reference to "a nucleic acid coding sequence" includes one or more nucleic acid coding sequences, reference to "an enzyme" includes one or more enzymes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

Accession Numbers: Sequence Accession numbers throughout this description were obtained from databases provided by the NCBI (National Center for Biotechnology Information) maintained by the National Institutes of Health, U.S.A. (which are identified herein as "NCBI Adcession Numbers" or alternatively as "GenBank Accession Numbers"), and from the UniProt Knowledgebase (UniProtKB) and Swiss-Prot databases provided by the Swiss Institute of Bioinformatics (which are identified herein as "UniProtKB Accession Numbers").

Enzyme Classification (EC) Numbers: EC numbers are established by the Nomenclature Committee of the International Union of Biochemistry and Molecular Biology (IUBMB), description of which is available on the IUBMB Enzyme Nomenclature website on the World Wide Web. EC. numbers classify enzymes according to the reaction catalyzed.

The term "FadR polypeptide" refers to a polypeptide having biological activity corresponding to that of FadR derived from E. coli MG1655 (SEQ ID NO: 1).

As used herein, the term "fatty acid or derivative thereof" means a "fatty acid" or a "fatty acid derivative." The term "fatty acid" means a carboxylic acid having the formula RCOOH. R represents an aliphatic group, preferably an alkyl group. R can comprise between about 4 and about 22 carbon atoms. Fatty acids can be saturated, monounsaturated, or polyunsaturated. In a preferred embodiment, the fatty acid is made from a fatty acid biosynthetic pathway. A "fatty acid derivative" is a product made in part from the fatty acid biosynthetic pathway of the production host organism. "Fatty acid derivatives" includes products made in part from acyl-ACP or acyl-ACP derivatives. Exemplary fatty acid derivatives include, for example, acyl-CoA, fatty acids, fatty aldehydes, short and long chain alcohols, hydrocarbons, fatty alcohols, esters (e.g., waxes, fatty acid esters, or fatty esters), terminal olefins, internal olefins, and ketones.

A "fatty acid derivative composition" as referred to herein is produced by a recombinant host cell and typically comprises a mixture of fatty acid derivative. In some cases, the mixture includes more than one type of product (e.g., fatty acids and fatty alcohols, fatty acids and fatty acid esters or alkanes and olefins). In other cases, the fatty acid derivative compositions may comprise, for example, a mixture of fatty alcohols (or another fatty acid derivative) with various chain lengths and saturation or branching characteristics. In still other cases, the fatty acid derivative composition comprises a mixture of both more than one type of product and products with various chain lengths and saturation or branching characteristics.

As used herein "acyl-CoA" refers to an acyl thioester formed between the carbonyl carbon of alkyl chain and the sulfhydryl group of the 4'-phosphopantethionyl moiety of coenzyme A (CoA), which has the formula R—C(O)S-CoA, where R is any alkyl group having at least 4 carbon atoms.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

As used herein, the term "fatty acid biosynthetic pathway" means a biosynthetic pathway that produces fatty acids. The fatty acid biosynthetic pathway includes fatty acid synthases that can be engineered to produce fatty acids, and in some embodiments can be expressed with additional enzymes to produce fatty acids having desired carbon chain characteristics.

As used herein, "fatty aldehyde" means an aldehyde having the formula RCHO characterized by a carbonyl group (C=O). In some embodiments, the fatty aldehyde is any aldehyde made from a fatty acid or fatty acid derivative.

As used herein, "fatty alcohol" means an alcohol having the formula ROH. In some embodiments, the fatty alcohol is any alcohol made from a fatty acid or fatty acid derivative.

In certain embodiments, the R group of a fatty acid, fatty aldehyde, or fatty alcohol is at least 5, at least 6, at least 7, at least 8, at least 9, at least 10, at least 11, at least 12, at least 13, at least 14, at least 15, at least 16, at least 17, at least 18, or at least 19, carbons in length. Alternatively, or in addition, the R group is 20 or less, 19 or less, 18 or less, 17 or less, 16 or less, 15 or less, 14 or less, 13 or less, 12 or less, 11 or less, 10 or less, 9 or less, 8 or less, 7 or less, or 6 or less carbons in length. Thus, the R group can have an R group bounded by any two of the above endpoints. For example, the R group can be 6-16 carbons in length, 10-14 carbons in length, or 12-18 carbons in length. In some embodiments, the fatty acid, fatty aldehyde, or fatty alcohol is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ fatty acid, fatty aldehyde, or fatty alcohol. In certain embodiments, the fatty acid, fatty aldehyde, or fatty alcohol is a $C_6$, $C_8$, $C_{10}$, $C_{12}$, $C_{13}$, $C_{14}$, $C_{15}$, $C_{16}$, $C_{17}$, or Cis fatty acid, fatty aldehyde, or fatty alcohol.

The R group of a fatty acid, fatty aldehyde, or fatty alcohol can be a straight chain or a branched chain. Branched chains may have more than one point of branching and may include cyclic branches. In some embodiments, the branched fatty acid, branched fatty aldehyde, or branched fatty alcohol is a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, or a $C_{26}$ branched fatty acid, branched fatty aldehyde, or branched fatty alcohol. In particular embodiments, the branched fatty acid, branched fatty aldehyde, or branched fatty alcohol is a $C_6$, $C_8$, $C_{10}$, $C_{12}$, $C_{13}$, $C_{14}$, $C_{15}$, $C_{16}$, $C_{17}$, or $C_{18}$ branched fatty acid, branched fatty aldehyde, or branched fatty alcohol. In certain embodiments, the hydroxyl group of the branched fatty acid, branched fatty aldehyde, or branched fatty alcohol is in the primary ($C_1$) position.

In certain embodiments, the branched fatty acid, branched fatty aldehyde, or branched fatty alcohol is an iso-fatty acid, iso-fatty aldehyde, or iso-fatty alcohol, or an antesio-fatty acid, an anteiso-fatty aldehyde, or anteiso-fatty alcohol. In exemplary embodiments, the branched fatty acid, branched fatty aldehyde, or branched fatty alcohol is selected from iso-$C_{7:0}$, iso-$C_{8:0}$, iso-$C_{9:0}$, iso-$C_{10:0}$, iso-$C_{11:0}$, iso $C_{12:0}$, iso-$C_{13:0}$, iso-$C_{14:0}$, iso-$C_{15:0}$, iso-$C_{16:0}$, iso-$C_{17:0}$, iso-$C_{18:0}$, iso-$C_{19:0}$, anteiso-$C_{7:0}$, anteiso-$C_{8:0}$, anteiso-$C_{9:0}$, anteiso-$C_{10:0}$, anteiso-$C_{11:0}$, anteiso-$C_{12:0}$, anteiso-$C_{13:0}$, anteiso-$C_{14:0}$, anteiso-$C_{15:0}$, anteiso-$C_{16:0}$, anteiso-$C_{17:0}$, anteiso-$C_{18:0}$, and anteiso-$C_{19:0}$ branched fatty acid, branched fatty aldehyde or branched fatty alcohol.

The R group of a branched or unbranched fatty acid, branched or unbranched fatty aldehyde, or branched or unbranched fatty alcohol can be saturated or unsaturated. If unsaturated, the R group can have one or more than one point of unsaturation. In some embodiments, the unsaturated fatty acid, unsaturated fatty aldehyde, or unsaturated fatty alcohol is a monounsaturated fatty acid, monounsaturated fatty aldehyde, or monounsaturated fatty alcohol. In certain embodiments, the unsaturated fatty acid, unsaturated fatty aldehyde, or unsaturated fatty alcohol is a C6:1, C7:1, C8:1, C9:1, C10:1, C11:1, C12:1, C13:1, C14:1, C15:1, C16:1, C17:1, C18:1, C19:1, C20:1, C21:1, C22:1, C23:1, C24:1, C25:1, or a C26:1 unsaturated fatty acid, unsaturated fatty aldehyde, or unsaturated fatty alcohol. In certain preferred embodiments, the unsaturated fatty acid, unsaturated fatty aldehyde, or unsaturated fatty alcohol is C10:1, C12:1, C14:1, C16:1, or C18:1. In yet other embodiments, the unsaturated fatty acid, unsaturated fatty aldehyde, or unsaturated fatty alcohol is unsaturated at the omega-7 position. In certain embodiments, the unsaturated fatty acid, unsaturated fatty aldehyde, or unsaturated fatty alcohol comprises a cis double bond.

As used herein, the term "alkane" means saturated hydrocarbons or compounds that consist only of carbon (C) and hydrogen (H), wherein these atoms are linked together by single bonds (i.e., they are saturated compounds).

The terms "olefin" and "alkene" are used interchangeably herein, and refer to hydrocarbons containing at least one carbon-to-carbon double bond (i.e., they are unsaturated compounds).

The terms "terminal olefin," "α-olefin", "terminal alkene" and "1-alkene" are used interchangeably herein with reference to α-olefins or alkenes with a chemical formula $C_xH2_x$, distinguished from other olefins with a similar molecular formula by linearity of the hydrocarbon chain and the position of the double bond at the primary or alpha position.

As used herein, the term "fatty ester" may be used in reference to an ester. In a preferred embodiment, a fatty ester is any ester made from a fatty acid, for example a fatty acid ester. In some embodiments, a fatty ester contains an A side and a B side. As used herein, an "A side" of an ester refers to the carbon chain attached to the carboxylate oxygen of the ester. As used herein, a "B side" of an ester refers to the carbon chain comprising the parent carboxylate of the ester. In embodiments where the fatty ester is derived from the fatty acid biosynthetic pathway, the A side is contributed by an alcohol, and the B side is contributed by a fatty acid.

Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied in the fermentation broth in instances where the fatty ester is produced by an organism. Alternatively, a carboxylic acid, such as a fatty acid or acetic acid, can be supplied exogenously in instances Where the fatty ester is produced by an organism that can also produce alcohol.

The carbon chains comprising the A side or B side can be of any length. In one embodiment, the A side of the ester is at least about 1, 2, 3, 4, 5, 6, 7, 8, 10, 12, 14, 16, or 18 carbons in length. When the fatty ester is a fatty acid methyl ester, the A side of the ester is 1 carbon in length. When the fatty ester is a fatty acid ethyl ester, the A side of the ester is 2 carbons in length. The B side of the ester can be at least about 4, 6, 8, 10, 12, 14, 16, 18, 20, 22, 24, or 26 carbons in length. The A side and/or the B side can be straight or branched chain. The branched chains can have one or more points of branching. In addition, the branched chains can include cyclic branches. Furthermore, the A side and/or B side can be saturated or unsaturated. If unsaturated, the A side and/or B side can have one or more points of unsaturation.

In some embodiments, the fatty acid ester is a fatty acid methyl ester (FAME) or a fatty acid ethyl ester (FAEE). In certain embodiments, the FAME is a beta-hydroxy (B-OH) FAME. In one embodiment, the fatty ester is produced biosynthetically. In this embodiment, first the fatty acid is "activated." Non-limiting examples of "activated" fatty acids are acyl-CoA, acyl ACP, and acyl phosphate. Acyl- CoA can be a direct product of fatty acid biosynthesis or degradation. In addition, acyl-CoA can be synthesized from a free fatty acid, a CoA, and an adenosine nucleotide triphosphate (ATP). An example of an enzyme which produces acyl-CoA is acyl-CoA synthase.

After a fatty acid is activated, it can be readily transferred to a recipient nucleophile. Exemplary nucleophiles are alcohols, thiols, or phosphates.

In one embodiment, the fatty ester is a wax. The wax can be derived from a long chain alcohol and a long chain fatty acid. In another embodiment, the fatty ester is a fatty acid thioester, for example, fatty acyl Coenzyme A (CoA). In other embodiments, the fatty ester is a fatty acyl pantothenate, an acyl carrier protein (ACP), or a fatty phosphate ester.

As used herein "acyl CoA" refers to an acyl thioester formed between the carbonyl carbon of alkyl chain and the sulfydryl group of the 4'-phosphopantethionyl moiety of coenzyme A (CoA), which has the formula R—C(O)S-CoA, where R is any alkyl group having at least 4 carbon atoms. In some instances an acyl CoA will be an intermediate in the synthesis of fully saturated acyl CoAs, including, but not limited to 3-keto-acyl CoA, a 3-hydroxy acyl CoA, a delta-2-trans-enoyl-CoA, or an alkyl acyl CoA. In some embodiments, the carbon chain will have about 5, 6, 7, 8, 9, 10, 11, 12, 13, 14, 15, 16, 17, 18, 19, 20, 21, 22, 23, 24, 25, or 26 carbons. In other embodiments the acyl CoA will be branched. In one embodiment the branched acyl CoA is an isoacyl CoA, in another it is an anti-isoacyl CoA. Each of these "acyl CoAs" are substrates for enzymes that convert them to fatty acid derivatives such as those described herein.

The terms "altered level of expression" and "modified level of expression" are used interchangeably and mean that a polynucleotide, polypeptide, or hydrocarbon is present in a different concentration in an engineered host cell as compared to its concentration in a corresponding wild-type cell under the same conditions.

"Polynucleotide" refers to a polymer of DNA or RNA, which can be single-stranded or double-stranded and which can contain non-natural or altered nucleotides. The terms "polynucleotide," "nucleic acid," and "nucleic acid molecule" are used herein interchangeably to refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to plasmid, viral, chromosomal, EST, cDNA, mRNA, and rRNA.

The term "nucleotide" as used herein refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

Polynucleotides described herein may comprise degenerate nucleotides which are defined according to the IUPAC code for nucleotide degeneracy wherein B is C, G, or T; D is A; G, or T; H is A, C, or T; K is G or T; M is A or C; N is A, C, G, or T; R is A or G; S is C or G; V is A, C, or G; W is A or T; and Y is C or T.

The terms "polypeptide" and "protein" refer to a polymer of amino acid residues. The term "recombinant polypeptide" refers to a polypeptide that is produced by recombinant DNA techniques, wherein generally DNA encoding the expressed protein or RNA is inserted into a suitable expression vector that is in turn used to transform a host cell to produce the polypeptide or RNA.

In some embodiments, the polypeptide, polynucleotide, or hydrocarbon having an altered or modified level of expression is "overexpressed" or has an "increased level of expression." As used herein, "overexpress" and "increasing the level of expression" mean to express or cause to be expressed a polynucleotide, polypeptide, or hydrocarbon in a cell at a greater concentration than is normally expressed in a corresponding wild-type cell under the same conditions. For example, a polypeptide can be "overexpressed" in an engineered host cell when the polypeptide is present in a greater concentration in the engineered host cell as compared to its concentration in a non-engineered host cell of the same species under the same conditions.

In other embodiments, the polypeptide, polynucleotide, or hydrocarbon having an altered level of expression is "attenuated" or has a "decreased level of expression." As used herein, "attenuate" and "decreasing the level of expression" mean to express or cause to be expressed a polynucleotide, polypeptide, or hydrocarbon in a cell at a lesser concentration than is normally expressed in a corresponding wild-type cell under the same conditions.

The degree of overexpression or attenuation can be 1.5-fold or more, e.g., 2-fold or more, 3-fold or more, 5-fold or more, 10-fold or more, or 15-fold or more. Alternatively, or in addition, the degree of overexpression or attenuation can be 500-fold or less, e.g., 100-fold or less, 50-fold or less, 25-fold or less, or 20-fold or less. Thus, the degree of overexpression or attenuation can be bounded by any two of the above endpoints. For example, the degree of overexpression or attenuation can be 1.5-500-fold, 2-50-fold, 10-25-fold, or 15-20-fold.

In some embodiments, a polypeptide described herein has "increased level of activity." By "increased level of activity" is meant that a polypeptide has a higher level of biochemical or biological function (e.g., DNA binding or enzymatic activity) in an engineered host cell as compared to its level of biochemical and/or biological function in a corresponding wild-type host cell under the same conditions. The degree of enhanced activity can be about 10% or more, about 20% or more, about 50% or more, about 75% or more, about 100% or more, about 200% or more, about 500% or more, about 1000% or more, or any range therein.

A polynucleotide or polypeptide can be attenuated using methods known in the art. In some embodiments, the expression of a gene or polypeptide encoded by the gene is attenuated by mutating the regulatory polynucleotide sequences which control expression of the gene. In other embodiments, the expression of a gene or polypeptide encoded by the gene is attenuated by overexpressing a repressor protein, or by providing an exogenous regulatory element that activates a repressor protein. In still yet other embodiments, DNA- or RNA-based gene silencing methods are used to attenuate the expression of a gene or polynucleotide. In some embodiments, the expression of a gene or polypeptide is completely attenuated, e.g., by deleting all or a portion of the polynucleotide sequence of a gene.

A polynucleotide or polypeptide can be overexpressed using methods known in the art. In some embodiments, overexpression of a polypeptide is achieved by the use of an exogenous regulatory element. The term "exogenous regulatory element" generally refers to a regulatory element originating outside of the host cell. However, in certain embodiments, the term "exogenous regulatory element" can refer to a regulatory element derived from the host cell whose function is replicated or usurped for the purpok of controlling the expression of an endogenous polypeptide. For example, if the host cell is an *E. coli* cell, and the FadR polypeptide is a encoded by an endogenous fadR gene, then expression of the endogenous fadR can be controlled by a promoter derived from another *E. coli* gene.

In some embodiments, the exogenous regulatory element is a chemical compound, such as a small molecule. As used herein, the term "small molecule" refers to a substance or compound having a molecular weight of less than about 1,000 g/mol.

In some embodiments, the exogenous regulatory element which controls the expression of an endogenous fadR gene is an expression control sequence which is operably linked to the endogenous fadR gene by recombinant integration into the genome of the host cell. Im certain embodiments, the expression control sequence is integrated into a host cell chromosome by homologous recombination using methods known in the art (e.g., Datsenko et al., *Proc. Natl. Acad. Sci. U.S.A.*, 97(12): 6640-6645 (2000)).

Expression control sequences are known in the art and include, for example, promoters, enhancers, polyadenylation signals, transcription terminators, internal ribosome entry sites (IRES), ribosome binding sites (RBS) and the like, that provide for the expression of the polynucleotide sequence in a host cell. Expression control sequences interact specifically with cellular proteins involved in transcription (Maniatis et al., *Science*, 236: 1237-1245 (1987)). Exemplary expression control sequences are described in, for example, Goeddel, *Gene Expression Technology: Methods in Enzymology*, Vol. 185, Academic Press, San Diego, Calif. (1990).

In the methods of the invention, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the polynucleotide sequence is provided to the host cell by way of a recombinant vector, which comprises a promoter operably linked to the polynucleotide sequence. In certain embodiments, the promoter is a developmentally-regulated, an organelle-specific, a tissue-specific, an inducible, a constitutive, or a cell-specific promoter.

As used herein, the term "vector" refers to a nucleic acid molecule capable of transporting another nucleic acid, i.e., a polynucleotide sequence; to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, inasmuch as a plasmid is the most commonly used form of vector. However, also included are such other forms of expression vectors that serve equivalent functions and that become known in the art subsequently hereto.

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

As used herein, the phrase "the expression of said nucleotide sequence is modified relative to the wild type nucleotide sequence," means an increase or decrease in the level of expression and/or activity of an endogenous nucleotide sequence or the expression and/or activity of a heterologous or non-native polypeptide-encoding nucleotide sequence.

As used herein, the term "express" with respect to a polynucleotide is to cause it to function. A polynucleotide which encodes a polypeptide (or protein) will, when expressed, be transcribed and translated to produce that polypeptide (or protein). As used herein, the term "overexpress" means to express or cause to be expressed a polynucleotide or polypeptide in a cell at a greater concentration than is normally expressed in a corresponding wild-type cell under the same conditions.

In some embodiments, the recombinant vector comprises at least one sequence selected from the group consisting of (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence.

The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein.

Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX (Pharmacia Biotech, Inc., Piscataway, N.J.; Smith et al., Gene, 67: 31-40 (1988)), pMAL (New England Biolabs, Beverly, Mass.), and pRITS (Pharmacia Biotech, Inc., Piscataway, N.J.), which fuse glutathione S-transferase (GST), maltose E binding protein, or protein A, respectively, to the target recombinant polypeptide.

Suitable expression systems for both prokaryotic and eukaryotic cells are well known in the art; see, e.g., Sambrook et al., "Molecular Cloning: A Laboratory Manual," second edition, Cold Spring Harbor Laboratory (1989). Examples of inducible, non-fusion E. coli expression vectors include pTrc (Amann et al., Gene, 69: 301-315 (1988)) and PET 11d (Studier et al., Gene Expression Technology: Methods in Enzymology 185, Academic Press, San Diego, Calif., pp. 60-89 (1990)). In certain embodiments, a polynucleotide sequence of the invention is operably linked to a promoter derived from bacteriophage T5. Examples of vectors for expression in yeast include pYepSecl (Baldari et al., EMBO J., 6: 229-234 (1987)), pMFa (Kurjan et al., Cell, 30: 933-943 (1982)), pJRY88 (Schultz et al., Gene, 54: 113-123 (1987)), pYES2 (Invitrogen Corp., San Diego, Calif.), and picZ (Invitrogen Corp., San Diego, Calif.). Baculovirus vectors available for expression of proteins in cultured insect cells (e.g., SD cells) include, for example, the pAc series (Smith et al., Mol. Cell Biol., 3: 2156-2165 (1983)) and the pVL series (Lucklow et al., Virology, 170: 31-39 (1989)). Examples of mammalian expression vectors include pCDM8 (Seed, Nature, 329: 840 (1987)) and pMT2PC (Kaufman et al., EMBO J., 6: 187-195 (1987)).

Vectors can be introduced into prokaryotic or eukaryotic cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in, for example, Sambrook et al. (supra).

For stable transformation of bacterial cells, it is known that, depending upon the expression vector and transformation technique used, only a small fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector. Cells stably transformed with the introduced nucleic acid can be identified by growth in the presence of an appropriate selection drug.

Similarly, for stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to an antibiotic) can be introduced into the host cells along with the gene of interest. Preferred selectable markers include those which confer resistance to drugs, such as G418, hygromycin, and methotrexate. Nucleic acids encoding a selectable marker can be introduced into a host cell on the same vector as that encoding a polypeptide described herein or can be introduced on a separate vector. Cells stably transfected with the introduced nucleic acid can be identified by growth in the presence of an appropriate selection drug.

In some embodiments, the FadR polypeptide has the amino acid sequence of SEQ ID NO: 1.

In other embodiments, the FadR polypeptide is encoded by a fadR gene obtained from microorganisms of the genera *Escherichia, Salmonella, Citrobacter, Enterobacter, Klebsiella, Cronobacter, Yersinia, Serratia, Erwinia*, Pectobacterium, *Photorhabdus, Edwardsiella, Shewanella*, or *Vibrio*.

In other embodiments, the FadR polypeptide is a homologue of FadR having an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 1.

The identity of a FadR polypeptide having at least 80% identity to the amino acid sequence of SEQ ID NO: 1 is not particularly limited, and one of ordinary skill in the art can readily identify homologues of E. coli MG1655 derived-FadR using the methods described herein as well as methods known in the art.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 2%, 93%, 94%, 95%, 96%, 97%, 98% or at least about 99% homology to the corresponding amino acid sequence or polynucleotide sequence. As used herein the terms sequence "homology" and sequence "identity" are used interchangeably.

Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps and the length of each gap, which need to be introduced for optimal alignment of the two sequences.

The comparison of sequences and determination of percent homology between two sequences can be accomplished using a mathematical algorithm, such as BLAST (Altschul et al., *J. Mol. Biol.*, 215(3): 403-410 (1990)). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, *J. Mol. Biol.*, 48: 444-453 (1970)). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring Matrix with a gap penalty of 12, a gap extend penalty of 4, and a frameshift gap penalty of 5. Additional methods of sequence alignment are known in the biotechnology arts (see, e.g., Rosenberg, *BMC Bioinformatics*, 6: 278 (2005); Altschul et al., *FEBS J.*, 272(20): 5101-5109 (2005)).

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either method can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2.X SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions unless otherwise specified.

In some embodiments, the polypeptide is a fragment of any of the polypeptides described herein. The term "fragment" refers to a shorter portion of a full-length polypeptide or protein ranging in size from four amino acid residnes to the entire amino acid sequence minus one amino acid residue. In certain embodiments of the invention, a fragment refers to the entire amino acid sequence of a domain of a polypeptide or protein (e.g., a substrate binding domain or a catalytic domain).

An "endogenous" polypeptide refers to a polypeptide encoded by the genome of the parental microbial cell (also termed "host cell") from which the recombinant cell is engineered (or "derived").

An "exogenous" polypeptide refers to a polypeptide which is not encoded by the genome of the parental microbial cell. A variant (i.e., mutant) polypeptide is an example of an exogenous polypeptide.

The term "heterologous" as used herein typically refers to a nucleotide sequence or a protein not naturally present in an organism. For example, a polynucleotide sequence endogenous to a plant can be introduced into a host cell by recombinant methods, and the plant polynucleotide is then a heterologous polynucleotide in a recombinant host cell.

In some embodiments, the polypeptide is a mutant or a variant of any of the polypeptides described herein. The terms "mutant" and "variant" as used herein refer to a polypeptide having an amino acid sequence that differs from a wild-type polypeptide by at least one amino acid. For example, the mutant can comprise one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the mutant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions.

As used herein, the term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g.; such sequences include but are not limited to ribosome binding sites or translational control sequences).

In certain embodiments, the FadR polypeptide comprises a mutation at an amino acid residue corresponding to amino acid 219 of SEQ ID NO: 1. In certain embodiments, the mutation results in a substitution of the amino acid residue corresponding to amino acid 219 of SEQ ID NO: 1 with an asparagine residue. The FadR(S219N) mutation has been previously described (Raman et al., *J. Biol. Chem.*, 270: 1092-1097 (1995)).

Preferred fragments or mutants of a polypeptide retain some or all of the biological function (e.g., enzymatic activity) of the corresponding wild-type polypeptide. In some embodiments, the fragment or mutant retains at least 75%, at least 80%, at least 90%, at least 95%, or at least 98% or more of the biological function of the corresponding wild-type polypeptide. In other embodiments, the fragment or mutant retains about 100% of the biological function of the corresponding wild-type polypeptide. Guidance in determining which amino acid residues may be substituted, inserted, or deleted without affecting biological activity may be found using computer programs well known in the art, for example, LASERGENE' software (DNASTAR, Inc., Madison, Wis.).

In yet other embodiments, a fragment or mutant exhibits increased biological function as compared to a corresponding wild-type polypeptide. For example, a fragment or mutant may display at least a 10%, at least a 25%, at least a 50%, at least a 75%, or at least a 90% improvement in enzymatic activity as compared to the corresponding wild-type polypeptide. In other embodiments, the fragment or mutant displays at least 100% (e.g., at least 200%, or at least 500%) improvement in enzymatic activity as compared to the corresponding wild-type polypeptide.

It is understood that the polypeptides described herein may have additional conservative or non-essential amino acid substitutions, which do not have a substantial effect on the polypeptide function. Whether or not a particular substitution will be tolerated (i.e., will not adversely affect desired biological function, such as DNA binding or enzyme activity) can be determined as described in Bowie et al. (*Science*, 247: 13061310 (1990)).

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Variants can be naturally occurring or created in vitro. In particular, such variants can be created using genetic engineering techniques, such as site directed mutagenesis, random chemical mutagenesis, Exonuclease III deletion procedures, or standard cloning techniques. Alternatively, such variants, fragments, analogs, or derivatives can be created using chemical synthesis or modification procedures.

Methods of making variants are well known in the art. These include procedures in which nucleic acid sequences obtained from natural isolates are modified to generate nucleic acids that encode polypeptides having characteristics that enhance their value in industrial or laboratory applications. In such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be prepared by using random and site-directed mutagenesis (see, e.g., Arnold, *Curr. Opin. Biotech.*, 4: 450-455 (1993)). Random mutagenesis can be achieved using error prone PCR (see, e.g., Leung et al., *Technique*, 1: 11-15 (1989); and Caldwell et al., *PCR Methods Applic.*, 2: 28-33 (1992)). Site-directed mutagenesis can be achieved using oligonucleotide-directed mutagenesis to generate site-specific mutations in any cloned DNA of interest (see, e.g., Reidhaar-Olson et al., *Science*, 241: 53-57 (1988)). Other methods for generating variants include, e.g., assembly PCR (see, e.g., U.S. Pat. No. 5,965,408), sexual PCR mutagenesis (see, e.g., Stemmer, *Proc. Natl. Acad. Sci., U.S.A.*, 91: 10747-10751 (1994) and U.S. Pat. Nos. 5,965,408 and 5,939,250), recursive ensemble mutagenesis (see, e.g., Arkin et al., *Proc. Natl. Acad. Sci.,* *U.S.A.*, 89: 7811-7815 (1992)), and exponential ensemble mutagenesis (see, e.g., Delegrave et al., *Biotech. Res*, 11: 1548-. 1552 (1993).

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence (e.g., a polynucleotide sequence encoding a PPTase) in one of these strains will eventually generate random mutations within the DNA. Mutator strains suitable for use for in vivo mutagenesis are described in, for example, International Patent Application Publication No. WO 1991/016427.

Variants can also be generated using cassette mutagenesis. In cassette mutagenesis, a small region of a double-stranded DNA molecule is replaced with a synthetic oligonucleotide "cassette" that differs from the native sequence. The oligonucleotide often contains a completely and/or partially randomized native sequence.

As used herein, a "host cell" is a cell used to produce a product described herein (e.g., a fatty aldehyde or a fatty alcohol). In any of the aspects of the invention described herein, the host cell can be selected from the group consisting of a mammalian cell, plant cell, insect cell, fungus cell. (e.g., a filamentous fungus cell or a yeast cell), and bacterial cell. A host cell is referred to as an "engineered host cell" or a "recombinant host cell" if the expression of one or more polynucleotides or polypeptides in the host cell are altered or modified as compared to their expression in a corresponding wild-type host cell under the same conditions.

In some embodiments, the host cell is a Gram-positive bacterial cell. In other embodiments, the host cell is a Gram-negative bacterial cell.

In some embodiments, the host cell is selected from the genus *Escherichia, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Thametes, Chrysosporium, Saccharomyces, Stenotrophamonas, Schizosaccharomyces, Yarrowia,* or *Streptomyces.*

In other embodiments, the host cell is a *Bacillus lentus* cell, a *Bacillus brevis* cell, a *Bacillus stearothermophilus* cell, a *Bacillus lichen* formis cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell.

In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus* fumigates cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcus opacus* cell, a *Rhizomucor miehei* cell, or a *Mucor* michei cell.

In yet other embodiments, the host cell is a *Streptomyces lividans* cell or a *Streptomyces murinus* cell.

In yet other embodiments, the host cell is an Actinomycetes cell.

In some embodiments, the host cell is a *Saccharomyces cerevisiae* cell. In some embodiments, the host cell is a *Saccharomyces cerevisiae* cell.

In still other embodiments, the host cell is a CHO cell, a COS cell, a VERO cell, a BHK cell, a HeLa cell, a Cvl cell, an MDCK cell, a 293 cell, a 3T3 cell, or a PC12 cell.

In other embodiments, the host cell is a cell from a eukaryotic plant, algae, cyanobacterium, green-sulfur bacterium, green non-sulfur bacterium, purple sulfur bacterium, purple non-sulfur bacterium, extremophile, yeast, fungus, an engineered organism thereof, or a synthetic organism. In some embodiments, the host cell is light-dependent or fixes carbon. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Avabidopsis thaliana, Panicum virgatum, Miscanthus giganteus, Zea mays, Bortyococcuse braunii, Chlamlydomonas reinhardtii, Dunaliela salina, Synechococcus* Sp. PCC 7002, *Synechococcus* Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridiuthermocellum, Penicillium chyrsogenum, Pichia pastoris, Saccharomyces cerevisiae, Schizosaccharomyces pombe, Pseudomonasjhorescens*, or *Zymomonas mobilis*.

In certain preferred embodiments, the host cell is an *E. coli* cell. In some embodiments, the *E. coli* cell is a strain B, a strain C, a strain K, or a strain W *E. coli* cell.

In other embodiments, the host cell is a *Pantoea citrea* cell.

As used herein, the term "conditions permissive for the production" means any conditions that allow a host cell to produce a desired product, such as a fatty acid or a fatty acid derivative. Similarly, the term "conditions in which the polynucleotide sequence of a vector is expressed" means any conditions that allow a host cell to synthesize a polypeptide. Suitable conditions include, for example, fermentation conditions. Fermentation conditions can comprise many parameters, such as temperature ranges, levels of aeration, and media composition. Each of these conditions, individually and in combination, allows the host cell to grow. Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source.

As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, and turanose; cellulosic material and variants such as methyl cellulose and sodium carboxymethyl cellulose; saturated or unsaturated fatty acid esters, succinate, lactate, and acetate; alcohols, such as ethanol, methanol, and glycerol, or mixtures thereof. The carbon source can also be a product of photosynthesis, such as glucose. In certain preferred embodiments, the carbon source is biomass. In other preferred embodiments, the carbon source is glucose. In still other preferred embodiments, the carbon source is sucrose.

As used herein, the term "biomass" refers to any biological material from which a carbon source is derived. In some embodiments, a biomass is processed into a carbon source, which is suitable for bioconversion. In other embodiments, the biomass does not require further processing into a carbon source. The carbon source can be converted into a biofuel. An exemplary source of biomass is plant matter or vegetation, such as corn, sugar cane, or switchgrass. Another exemplary source of biomass is metabolic waste products, such as animal matter (e.g., cow manure). Further exemplary sources of biomass include algae and other marine plants. Biomass also includes waste products from industry, agriculture, forestry, and households, including, but not limited to, fermentation waste, ensilage, straw, lumber, sewage, garbage, cellulosic urban waste, and food leftovers. The term "biomass" also can refer to sources of carbon, such as carbohydrates (e.g., monosaccharides, disaccharides, or polysaccharides).

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells, reproducing in a predetermined culture media under controlled conditions, for example, a culture of recombinant host cells grown in liquid media comprising a selected carbon source and nitrogen.

"Culturing" or "cultivation" refers to growing a population of recombinant host cells under suitable conditions in a liquid or solid medium. In particular embodiments, culturing refers to the fermentative bioconversion of a substrate to an end-product. Culturing media are well known and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium.

To determine if conditions are sufficient to allow production of a product or expression of a polypeptide, a host cell can be cultured, for example, for about 4, 8, 12, 24, 36, 48, 72, or more hours. During and/or after culturing, samples can be obtained and analyzed to determine if the conditions allow production or expression. For example, the host cells in the sample or the medium in which the host cells were grown can be tested for the presence of a desired product. When testing for the presence of a fatty acid or fatty acid derivative, assays, such as, but not limited to, mass spectrometry (MS), thin layer chromatography (TLC), high-performance liquid chromatography (HPLC), liquid chromatography (LC), GC coupled with a flame ionization detector (FID), and liquid chromatography-mass spectrometry (LC-MS) can be used. When testing for the expression of a polypeptide, techniques such as, but not limited to, Western blotting and dot blotting may be used.

In the compositions and methods of the invention, the production and isolation of fatty acids and fatty acid derivatives can be enhanced by optimizing fermentation conditions. In some embodiments, fermentation conditions are optimized to increase the percentage of the carbon source that is converted to hydrocarbon products. During normal cellular lifecycles, carbon is used in cellular functions, such as producing lipids, saccharides, proteins, organic acids, and nucleic acids. Reducing the amount of carbon necessary for growth-related activities can increase the efficiency of carbon source conversion to product. This can be achieved by, for example, first growing host cells to a desired density (for example, a density achieved at the peak of the log phase of growth). At such a point, replication checkpoint genes can be harnessed to stop the growth of cells. Specifically, quorum sensing mechanisms (reviewed in Camilli et al., *Science* 311: 1113 (2006); *Venturi, FEMS MicrobioL Rev.*, 30: 274-291 (2006); and Reading et al., *FEMS Microbiol. Lett.*, 254: 1-11 (2006)) can be used to activate checkpoint genes, such as p53, p21, or other checkpoint genes.

Genes that can be activated to stop cell replication and growth in *E. coli* include umuDC genes. The overexpression of umuDC genes stops the progression from stationary phase to exponential growth (Murli et al., *J. Bacteriol.*, 182: 1127-1135 (2000)). UmuC is a DNA polymerase that can carry out translesion synthesis over non-coding lesions which commonly result from ultraviolet (UV) and chemical mutagenesis. The umuDC gene products are involved in the process of translesion synthesis and also serve as a DNA sequence damage checkpoint. The umuDC gene products include UmuC, UmuD, umuD', UmuD'$_2$C, UmuD'$_2$, and UmuD$_2$. Simultaneously, product-producing genes can be activated, thereby minimizing the need for replication and maintenance pathways to be used while a fatty aldehyde or fatty alcohol is being made. Host cells can also be engineered to express umuC and umuD from *E. coli* in pBAD24 under the prpBCDE promoter system through de novo synthesis of this gene with the appropriate end-product production genes.

The host cell can be additionally engineered to express a recombinant cellulosome, which can allow the host cell to use cellulosic material as a carbon source. Exemplary cellulosomes suitable for use in the methods of the invention include, e.g., the cellulosomes described in International Patent Application Publication WO 2008/100251. The host cell also can be engineered to assimilate carbon efficiently and use cellulosic materials as carbon sources according to methods described in U.S. Pat. Nos. 5,000,000; 5,028,539; 5,424,202; 5,482,846; and 5,602,030. In addition, the host cell can be engineered to express an invertase so that sucrose can be used as a carbon source.

In some embodiments of the fermentation methods of the invention, the fermentation chamber encloses a fermentation that is undergoing a continuous reduction, thereby creating a stable reductive environment. The electron balance can be maintained by the release of carbon dioxide (in gaseous form). Efforts to augment the NAD/H and NADP/H balance can also facilitate in stabilizing the electron balance. The availability of intracellular NADPH can also be enhanced by engineering the host cell to express an NADH:NADPH transhydrogenase. The expression of one or more NADH:NADPH transhydrogenases converts the NADH produced in glycolysis to NADPH, which can enhance the production of fatty aldehydes and fatty alcohols.

For small scale production, the engineered host cells can be grown in batches of, for example, about 100 mL, 500 mL, 1 L, 2 L, 5 L, or 10 L; fermented; and induced to express a desired polynucleotide sequence, such as a polynucleotide sequence encoding a PPTase. For large scale production, the engineered host cells can be grown in batches of about 10 L, 100 L, 1000 L, 10,000 L, 100,000 L, 1,000,000 L or larger; fermented; and induced to express a desired polynucleotide sequence.

The fatty acids and derivatives thereof produced by the methods of invention generally are isolated from the host cell. The term "isolated" as used herein with respect to products, such as fatty acids and derivatives thereof, refers to products that are separated from cellular components, cell culture media, or chemical or synthetic precursors. The fatty acids and derivatives thereof produced by the methods described herein can be relatively immiscible in the fermentation broth, as well as in the cytoplasm. Therefore, the fatty acids and derivatives thereof can collect in an organic phase either intracellularly or extracellularly. The collection of the products in the organic phase can lessen the impact of the fatty acid or fatty acid derivative on cellular function and can allow the host cell to produce more product.

In some embodiments, the fatty acids and fatty acid derivatives produced by the methods of invention are purified. As used herein, the term "purify," "purified," or "purification" means the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of a fatty aldehyde or a fatty alcohol in a sample. For example, when a fatty aldehyde or a fatty alcohol is produced in a host cell, the fatty aldehyde or fatty alcohol can be purified by the removal of host cell proteins. After purification, the percentage of a fatty acid or derivative thereof in the sample is increased.

As used herein, the terms "purify," "purified," and "purification" are relative terms which do not require absolute purity. Thus, for example, when a fatty acid or derivative thereof is produced in host cells, a purified fatty acid or derivative thereof is a fatty acid or derivative thereof that is substantially separated from other cellular components (e.g., nucleic acids, polypeptides, lipids, carbohydrates, or other hydrocarbons).

Additionally, a purified fatty acid preparation or a purified fatty acid derivative preparation is a fatty acid preparation or a fatty acid derivative preparation in which the fatty acid or derivative thereof is substantially free from contaminants, such as those that might be present following fermentation. In some embodiments, a fatty acid or derivative thereof is purified when at least about 50% by weight of a sample is composed of the fatty acid or fatty acid derivative. In other embodiments, a fatty acid or derivative thereof is purified when at least about 60%, e.g., at least about 70%, at least about 80%, at least about 85%, at least about 90%, at least about 92% or more by weight of a sample is composed of the fatty acid or derivative thereof. Alternatively, or in addition, a fatty acid or derivative thereof is purified when less than about 100%, e.g., less than about 99%, less than about 98%, less than about 95%, less than about 90%, or less than about 80% by weight of a sample is composed of the fatty acid or derivative thereof. Thus, a purified fatty acid or derivative thereof can have a purity level bounded by any two of the above endpoints. For example, a fatty acid or derivative thereof can be purified when at least about 80%-95%, at least about 85%-99%, or at least about 90%-98% of a sample is composed of the fatty acid or fatty acid derivative.

The fatty acid or derivative thereof may be present in the extracellular environment, or it may be isolated from the extracellular environment of the host cell. In certain embodiments, a fatty acid or derivative thereof is secreted from the host cell. In other embodiments, a fatty acid or derivative thereof is transported into the extracellular environment. In yet other embodiments, the fatty acid or derivative thereof is passively transported into the extracellular environment. A fatty acid or derivative thereof can be isolated from a host cell using methods known in the art, such as those disclosed in International Patent Application Publications WO 2010/042664 and WO 2010/062480.

The methods described herein can result in the production of homogeneous compounds wherein at least about 60%, at least about 70%, at least about 80%, at least about 90%, or at least about 95%, of the fatty acids or fatty acid derivatives produced will have carbon chain lengths that vary by less than 6 carbons, less than 5 carbons, less than 4 carbons, less than 3 carbons, or less than about 2 carbons. Alternatively, or in addition, the methods described herein can result in the production of homogeneous compounds wherein less than about 98%, less than about 95%, less than about 90%, less than about 80%, or less than about 70% of the fatty acids or fatty acid derivatives produced will have carbon chain lengths that vary by less than 6 carbons, less than 5 carbons, less than 4 carbons, less than 3 carbons, or less than about 2 carbons. Thus, the fatty acids or fatty acid derivatives can have a degree of homogeneity bounded by any two of the above endpoints. For example, the fatty acid or fatty acid derivative can have a degree of homogeneity wherein about 70%-95%, about 80%-98%, or about 90%-95% of the fatty acids or fatty acid derivatives produced will have carbon chain lengths that vary by less than 6 carbons, less than 5 carbons, less than 4 carbons, less than 3 carbons, or less than about 2 carbons. These compounds can also be produced with a relatively uniform degree of saturation.

As a result of the methods of the present invention, one or more of the titer, yield, or productivity of the fatty acid or derivative thereof produced by the engineered host cell having an altered level of expression of a FadR polypeptide is increased relative to that of the corresponding wild-type host cell.

The term "titer" refers to the quantity of fatty acid or fatty acid derivative produced per unit volume of host cell culture. In any aspect of the compositions and methods described herein, a fatty acid or a fatty acid derivative such as a terminal olefin, a fatty aldehyde, a fatty alcohol, an alkane, a fatty ester, a ketone or an internal olefins is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 g/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 rng/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L, or a range bounded by any two of the foregoing values. In other embodiments, a fatty acid or fatty acid derivative is produced at a titer of more than 2000 mg/L, more than 5000 mg/L, more than 10,000 mg/L, or higher, such as 50 g/L, 70 g/L, 100 g/L, 120 g/L, 150 g/L, or 200 g/L.

As used herein, the "yield of fatty acid derivative produced by a host cell" refers to the efficiency by which an input carbon source is converted to product (i.e., fatty alcohol or fatty aldehyde) in a host cell. Host cells engineered to produce fatty acid derivatives according to the methods of the invention have a yield of at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% or a range bounded by any two of the foregoing values. In other embodiments, a fatty acid derivative or derivatives is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of a fatty acid derivative or derivatives produced by the recombinant host cell according to the methods of the invention can be 5% to 15%, 10% to 25%, 10% to 22%, 15% to 27%, 18% to 22%, 20% to 28%, or 20% to 30%. The yield may refer to a particular fatty acid derivative or a combination of fatty acid derivatives produced by a given recombinant host cell culture.

In one approach, the term "productivity of the fatty acid or derivative thereof produced by a host cell" refers to the quantity of fatty acid or fatty acid derivative produced per unit volume of host cell culture per unit density of host cell culture. In any aspect of the compositions and methods described herein, the productivity of a fatty acid or a fatty acid derivative such as an olefin, a fatty aldehyde, a fatty alcohol, an alkane, a fatty ester, or a ketone produced by an engineered host cells is at least about at least about 3 mg/L/OD$_{600}$, at least about 6 mg/L/OD$_{600}$, at least about 9 mg/L/OD$_{600}$, at least about 12 mg/L/OD$_{600}$, or at least about 15 mg/L/OD$_{600}$. Alternatively, or in addition, the productivity is about 50 ing/UOD600 or less, about 40 mg/L/OD$_{600}$ or less, about 30 mg/L/OD$_{600}$ or less, or about 20 mg/L/OD$_{600}$ or less. Thus, the productivity can be bounded by any two of the above endpoints. For example, the productivity can be about 3 to about 30 mg/L/OD$_{600}$, about 6 to about 20 mg/L/OD$_{600}$, or about 15 to about 30 mg/L/OD$_{600}$.

In another approach, the term "productivity" refers to the quantity of a fatty acid derivative or derivatives produced per unit volume of host cell culture per unit time. In any aspect of the compositions and methods described herein, the productivity of a fatty acid derivative or derivatives produced by a recombinant host cell is at least 100 mg/L/hour, at least 200 mg/L/hour 0, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/ hour, at least 2300 mg/L/hour, at least 2400 mg/L/hour, or at least 2500 mg/L/hour. Alternatively, or in addition, the productivity is 2500 mg/L/hour or less, 2000 mg/L/OD600 or less, 1500 mg/L/OD600 or less, 120 mg/L/hour, or less, 1000 mg/L/hour or less, 800 mg/L/hour, or less, or 600 mg/L/hour or less. Thus, the productivity can be bounded by any two of the above endpoints. For example, the productivity can be 3 to 30 mg/L/hour, 6 to 20 mg/L/hour, or 15 to 30 mg/L/hour. For example, the productivity of a fatty acid derivative or derivatives produced by a recombinant host cell according to the methods of the may be from 500 mg/L/hour to 2500 mg/L/hour, or from 700 mg/L/hour to 2000 mg/L/hour. The productivity may refer to a particular fatty acid derivative or a combination of fatty acid derivatives produced by a given recombinant host cell culture.

In the compositions and methods of the invention, the production and isolation of a desired fatty acid or derivative thereof (e.g., acyl-CoA, fatty acids, terminal olefins, fatty aldehydes, fatty alcohols, alkanes, alkenes, wax esters, ketones and internal olefins) can be enhanced by altering the expression of one or more genes involved in the regulation of fatty acid, fatty ester, alkane, alkene, olefin fatty alcohol production, degradation and/or secretion in the engineered host cell.

FadR is known to modulate the expression and/or activity of numerous genes, including fabA, fabB, iclR, fadA, fadB, fadD, fadE, fadI, fadJ, fadL, fadM, uspA, aceA, aceB, and aceK. In some embodiments of the methods described herein, the engineered host cell further comprises an altered level of expression of one or more genes selected from the group consisting of fabA, fabB, iclR, fadA, fadB, fadD, fadE, fadI, fadJ, fadL, fadM, uspA, aceA, aceB, and aceK as compared to the level of expression of the selected gene(s) in a corresponding wild-type host cell. Exemplary accession numbers for polypeptides encoded by the FadR target genes include fabA (NP_415474), fabB (BAA16180), (NP_418442), fadA (YP_026272.1), fadB (NP_418288.1), fadD (AP_002424), fadE (NP_414756.2), fadI (NP_416844.1), fadJ (NP_416843.1), fadL (AAC75404), fadM (NP_414977.1), uspA (AAC76520), aceA (AAC76985.1), aceB (AAC76984.1), and aceK (AAC76986.1).

Exemplary enzymes and polypeptides for use in practicing the invention are listed in FIG. 1. One of ordinary skill in the art will understand that depending upon the purpose (e.g., desired fatty acid or fatty acid derivative product), specific genes (or combinations of genes) listed in FIG. 1 may be overexpressed, modified, attenuated or deleted in an engineered host cell which has an altered level of expression of a FadR polypeptide.

In some embodiments, the method comprises modifying the expression of a gene encoding one or more of a thioesterase (e.g., TesA), a decarboxylase, a carboxylic acid reductase (CAR; e.g., CarB), an alcohol dehydrogenase (aldehyde reductase); an aldehyde decarbonylase, a fatty alcohol forming acyl-CoA reductase (FAR), an acyl ACP reductase (AAR), an ester synthase, an acyl-CoA reductase (ACR1), OleA, OleCD and OleBCD.

In certain embodiments of the invention, the engineered host cell having an altered level of expression of a FadR polypeptide may be engineered to further comprise a polynucleotide sequence encoding a polypeptide: (1) having thioesterase activity (EC 3.1.2.14), wherein the engineered host cell synthesizes fatty acids; (2) having decarboxylase activity, wherein the engineered host cell synthesizes terminal olefins; (3) having carboxylic acid reductase activity, wherein the engineered host cell synthesizes fatty aldehydes; (4) having carboxylic acid reductase and alcohol dehydrogenase activity (EC 1.1.1.1), wherein the engineered host cell synthesizes fatty alcohols; (5) having carboxylic acid reductase and aldehyde decarbonylase activity (EC 4.1.99.5), wherein the engineered host cell synthesizes alkanes; (6) having acyl-CoA reductase activity (EC 1.2.1.50), wherein microorganism synthesizes fatty aldehydes; (7) having acyl-CoA reductase activity (EC 1.2.1.50) and alcohol dehydrogenase activity (EC 1.1.1.1), wherein the engineered host cell synthesizes fatty alcohols; (8) having acyl-CoA reductase activity (EC 1.2.1.50) and aldehyde decarbonylase activity (EC 4.1.99.5), wherein the engineered host cell synthesizes alkanes; (9) having alcohol forming acyl CoA reductase activity wherein the engineered host cell synthesizes fatty aldehydes and fatty alcohols; (10) having carboxylic acid reductase activity, wherein the engineered host cell synthesizes fatty aldehydes; (11) having acyl ACP reductase activity, wherein the engineered host cell synthesizes fatty aldehydes; (12) having acyl ACP reductase activity and alcohol dehydrogenase activity (EC 1.1.1.1), wherein engineered host cell synthesizes fatty alcohols; (13) having acyl ACP reductase activity and aldehyde decarbonylase activity (EC 4.1.99.5), wherein engineered host cell synthesizes alkanes; (14) having ester synthase activity (EC 3.1.1.67), wherein the engineered host cell synthesizes fatty esters; (15) having ester synthase activity (EC 3.1.1.67) and (a) carboxylic acid reductase activity, (b) acyl-CoA reductase activity, (c) acyl ACP reductase activity, or (d) alcohol dehydrogenase activity (EC 1.1.1.1), wherein the engineered host cell synthesizes wax esters; (16) having OleA activity, wherein the engineered host cell synthesizes 2-alkyl-3-keto-acyl CoA and ketones; or (17) having OleCD or OleBCD activity, wherein the engineered host cell synthesizes internal olefins.

In some embodiments, the method further comprises modifying the expression of a gene encoding a fatty acid synthase in the host cell. As used herein, "fatty acid synthase" means any enzyme involved in fatty acid biosynthesis. In certain embodiments, modifying the expression of a gene encoding a fatty acid synthase includes expressing a gene encoding a fatty acid synthase in the host cell and/or increasing the expression or activity of an endogenous fatty acid synthase in the host cell. In alternate embodiments, modifying the expression of a gene encoding a fatty acid synthase includes attenuating a gene encoding a fatty acid synthase in the host cell and/or decreasing the expression or activity of an endogenous fatty acid synthase in the host cell. In some embodiments, the fatty acid synthase is a thioesterase (EC 3.1.1.5 or EC 3.1.2.14). In particular embodiments, the thioesterase is encoded by tesA, tesA without leader sequence, tesB, fatB, fatB2, fatB3, fatA, or fatA1.

In other embodiments, the host cell is genetically engineered to express an attenuated level of a fatty acid degradation enzyme relative to a wild-type host cell. As used herein, the term "fatty acid degradation enzyme" means an enzyme involved in the breakdown or conversion of a fatty acid or fatty acid derivative into another product, such as, but not limited to, an acyl-CoA synthase. In some embodiments, the host cell is genetically engineered to express an attenuated level of an acyl-CoA synthase relative to a wild-type host cell. In particular embodiments, the host cell expresses an attenuated level of an acyl-CoA synthase encoded by fadD, fadK, BH3103, yhfl, PJI-4354, EAV15023, fadD1, fadD2, RPC 4074, fadDD35, fadDD22, faa3p, or the gene encoding the protein YP_002028218. In certain embodiments, the genetically engineered host cell comprises a knockout of one or more genes encoding a fatty acid degradation enzyme, such as the aforementioned acyl-CoA synthase genes.

The fatty acid biosynthetic pathway in host cells uses the precursors acetyl-CoA and malonyl-CoA. The steps in this pathway are catalyzed by enzymes of the fatty acid biosynthesis (fab) and acetyl-CoA carboxylase (acc) gene families (see, e.g., Heath et al., *Prog. Lipid Res.* 40(6): 467-97 (2001)). Acetyl-CoA is carboxylated by acetyl-CoA carboxylase (EC 6.4.1.2), which is a multisubunit enzyme encoded by four separate genes (accA, accB, accC, and accD) in most prokaryotes, to form malonyl-CoA. In some bacteria, such as *Corynebacterium glutamicus*, acetyl-CoA carboxylase is consisted two subunits, AccDA [YP_225123.1] and AccBC [YP_224991], encoded by accDA and accBC, respectively. Depending upon the desired fatty acid or fatty acid derivative product, specific fab and/or acc genes (or combinations thereof) may be overexpressed, modified, attenuated or deleted in an engineered host cell.

In some embodiments, an acetyl-CoA carboxylase complex is overexpressed in the engineered host cell. In certain embodiments, the acetyl-CoA carboxylase subunit genes are obtained from one or more of *Corynebacterium glutamicum*, *Escherichia coli*, *Lactococcus lactis*, *Kineococcus radiotolerans*, *Desulfovibrio desulfuricans*, *Erwinia amylovora*, *Rhodospirillum rubrum*, *Vibrio furnissii*, *Stenotrophomonas maltophilia*, *Synechocystis* sp. PCC6803, and *Synechococcus elongatus*.

Biotin protein ligase (EC 6.3.4.15) is an enzyme that catalyzes the covalent attachment of biotin to the biotin carboxyl carrier protein (BCCP) subunit of acetyl-CoA carboxylase. In some embodiments of the present invention, a biotin protein ligase is expressed or overexpressed in the engineered host cell. In certain embodiments, the biotin protein ligase is birA from Corynebacterium *glutamicum* (YP_225000) or bpll from *Saccharomyces cerevisiae* (NP_010140).

The production of fatty acid esters such as FAMEs or FAEEs in a host cell can be facilitated by expression or overexpression of an ester synthase (EC 2.3.1.75 or EC 3.1.1.67) in an engineered host cell. In some embodiments, the ester synthase is ES9 from *Marinobacter hydrocarbonoclasticus* (SEQ ID NO: 2), ES8 from *Marinobacter hydrocarbonoclasticus* (SEQ ID NO: 3), AtfA1 from *Alcanivorax borkumensis* SK2 (SEQ ID NO: 4), AtfA2 from *Alcanivorax borkumensis* SK2 (SEQ ID NO: 5), diacylglycerol O-acyltransferase from *Marinobacter aquaeolei* VT8 (SEQ ID NO: 6 or SEQ ID NO: 7), a wax synthase, or a bifunctional wax ester synthase/acyl-CoA:diacylglycerol acyltransferase (wax-dgaT).

In certain embodiments, a gene encoding a fatty aldehyde biosynthetic polypeptide is expressed or overexpressed in the host cell. Exemplary fatty aldehyde biosynthetic polypeptides suitable for use in the methods of the invention are disclosed, for example, in International Patent Application Publication WO 2010/042664. In preferred embodiments, the fatty aldehyde biosynthetic polypeptide has carboxylic acid reductase (EC 6.2.1.3 or EC 1.2.1.42) activity, e.g., fatty acid reductase activity.

In the methods of the invention, the polypeptide having carboxylic acid reductase activity is not particularly limited. Exemplary polypeptides having carboxylic acid reductase activity which are suitable for use in the methods of the present invention are disclosed, for example, in International Patent Application Publications WO 2010/062480 and WO 2010/042664. In some embodiments, the polypeptide having carboxylic acid reductase activity is CarB from *M. smegmatis* (YP_889972) (SEQ ID NO: 8). In other embodiments, the polypeptide having carboxylic acid reductase activity is CarA [ABK75684] from M smeginatis, FadD9 [AAK46980] from *M. tuberculosis*, CAR [AAR91681] from *Nocardia* sp. NRRL 5646, CAR [YP-001070587] from *Mycobacterium* sp. JLS, or CAR [YP-118225] from *Streptomyces griseus*. The terms "carboxylic acid reductase," "CAR," and "fatty aldehyde biosynthetic polypeptide" are used interchangeably herein.

In certain embodiments, a thioesterase and a carboxylic acid reductase are expressed or overexpressed in the engineered host cell.

In some embodiments, a gene encoding a fatty alcohol biosynthetic polypeptide is expressed or overexpressed in the host cell. Exemplary fatty alcohol biosynthetic polypeptides suitable for use in the methods of the invention are disclosed, for example, in International Patent Application Publication WO 2010/062480. In certain embodiments, the fatty alcohol biosynthetic polypeptide has aldehyde reductase or alcohol dehydrogenase activity (EC 1.1.1.1). Exemplary fatty alcohol biosynthetic polypeptides include, but are not limited to AlrA of *Acenitobacter* sp. M-1 (SEQ ID NO: 9) or AlrA homologs and endogenous *E. coli* alcohol dehydrogenases such as YjgB, (AAC77226) (SEQ ID NO: 10), DkgA (NP_417485), DkgB (NP_414743), YdjL (AAC74846), YdjJ (NP_416288), AdhP (NP_415995), YhdH (NP_417719), YahK (NP_414859), YphC (AAC75598), YqhD (446856) and YbbO [AAC73595.1].

As used herein, the term "alcohol dehydrogenase" is a peptide capable of catalyzing the conversion of a fatty aldehyde to an alcohol (e.g., fatty alcohol). One of ordinary skill in the art will appreciate that certain alcohol dehydrogenases are capable of catalyzing other reactions as well. For example, certain alcohol dehydrogenases will accept other substrates in addition to fatty aldehydes, and these non-specific alcohol dehydrogenases also are encompassed by the term "alcohol dehydrogenase." Exemplary alcohol dehydrogenases suitable for use in the methods of the invention are disclosed, for example, in International Patent Application Publication WO 2010/062480.

In some embodiments, a thioesterase, a carboxylic acid reductase, and an alcohol dehydrogenase are expressed or overexpressed in the engineered host cell. In certain embodiments, the thioesterase is tesA (SEQ ID NO: 11), the carboxylic acid reductase is carB (SEQ ID NO: 8), and the alcohol dehydrogenase is YjgB (SEQ ID NO: 10) or AlrAadpl (SEQ ID NO: 9).

Phosphopantetheine transferases (PPTases) (EC 2.7.8.7) catalyze the transfer of 4'-phosphopantetheine from CoA to a substrate. *Nocardia* CAR and several of its homologues contain a putative attachment site for 4'-phosphopantetheine (PPT) (He et al., *Appl. Environ. Microbiol.*, 70(3): 1874-1881 (2004)). In some embodiments of the invention, a PPTase is expressed or overexpressed in an engineered host cell. In certain embodiments, the PPTase is EntD from *E. coli* MG1655 (SEQ ID NO: 12).

In some embodiments, a thioesterase, a carboxylic acid reductase, a PPTase, and an alcohol dehydrogenase are expressed or overexpressed in the engineered host cell. In certain embodiments, the thioesterase is tesA (SEQ ID NO: 11), the carboxylic acid reductase is carB (SEQ ID NO: 8); the PPTase is entD (SEQ ID NO: 12), and the alcohol dehydrogenase is yjgB (SEQ ID NO: 10) or alrAadpl (SEQ ID NO: 9).

The invention also provides a fatty acid or a fatty derivative produced by any of the methods described herein. A fatty acid or derivative thereof produced by any of the methods described herein can be used directly as fuels, fuel additives, starting materials for production of other chemical compounds (e.g., polymers, surfactants, plastics, textiles, solvents, adhesives, etc.), or personal care additives. These compounds can also be used as feedstock for subsequent reactions, for example, hydrogenation, catalytic cracking (e.g., via hydrogenation, pyrolisis, or both), to make other products.

In some embodiments, the invention provides a biofuel composition comprising the fatty acid or derivative thereof produced by the methods described herein. As used herein, the term "biofuel" refers to any fuel derived from biomass. Biofuels can be substituted for petroleum-based fuels. For example, biofuels are inclusive of transportation fuels (e.g., gasoline, diesel, jet fuel, etc.), heating fuels, and electricity-generating fuels. Biofuels are a renewable energy source. As used herein, the term "biodiesel" means a biofuel that can be a substitute of diesel, which is derived from petroleum. Biodiesel can be used in internal combustion diesel engines in either a pure form, which is referred to as "neat" biodiesel, or as a mixture in any concentration with petroleum-based diesel. Biodiesel can include esters or hydrocarbons, such as alcohols. In certain embodiments, the biofuel is selected from the group consisting of a biodiesel, a fatty alcohol, a fatty ester, a triacylglyceride, a gasoline, or a jet fuel.

Fuel additives are used to enhance the performance of a fuel or engine. For example, fuel additives can be used to alter the freezing/gelling point, cloud point, lubricity, viscosity, oxidative stability, ignition quality, octane level, and/or flash point of a fuel. In the United States, all fuel additives must be registered with Environmental Protection Agency (EPA). The names of fuel additives and the companies that sell the fuel additives are publicly available by contacting the EPA or by viewing the EPA's website. One of ordinary skill in the art will appreciate that a biofuel produced according to the methods described herein can be mixed with one or more fuel additives to impart a desired quality.

The invention also provides a surfactant composition or a detergent composition comprising a fatty alcohol produced by any of the methods described herein. One of ordinary skill in the art will appreciate that, depending upon the intended purpose of the surfactant or detergent composition, different fatty alcohols can be produced and used. For example, when the fatty alcohols described herein are used as a feedstock for surfactant or detergent production, one of ordinary skill in the art will appreciate that the characteristics of the fatty alcohol feedstock will affect the characteristics of the surfactant or detergent composition produced. Hence, the characteristics of the surfactant or detergent composition can be selected for by producing particular fatty alcohols for use as a feedstock.

A fatty alcohol-based surfactant and/or detergent composition described herein can be mixed with other surfactants and/or detergents well known in the art. In some embodiments, the mixture can include at least about 10%, at least about 15%, at least about 20%, at least about 30%, at least about 40%, at least about 50%, at least about 60%, or a range bounded by any two of the foregoing values, by weight of the fatty alcohol. In other examples, a surfactant or detergent composition can be made that includes at least about 5%, at least about 10%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of a fatty alcohol that includes a carbon chain that is 8, 9, 10, 11, 12, 13, 14, 15, 16, 17, 18, 19, 20, 21, or 22 carbons in length. Such surfactant or detergent compositions also can include at least one additive, such as a microemulsion or a surfactant or detergent from nonmicrobial sources such as plant oils or petroleum, which can be present in the amount of at least about 5%, at least about 10%, at least about 15%, at least about 20%, at least about 30%, at least about 40%, at least about 50%, at least about 60%, at least about 70%, at least about 80%, at least about 85%, at least about 90%, at least about 95%, or a range bounded by any two of the foregoing values, by weight of the fatty alcohol.

Bioproducts (e.g., fatty acids, acyl-CoAs, hydrocarbons, fatty aldehydes, fatty alcohols, fatty esters, surfactant compositions, and biofuel compositions) produced according to the methods of the invention can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588).

The ability to distinguish bioproducts from petroleum-based organic compounds is beneficial in tracking these materials in commerce. For example, organic compounds or chemicals comprising both biologically-based and petroleum-based carbon isotope profiles may be distinguished from organic compounds and chemicals made only of petroleum-based materials. Hence, the materials prepared in accordance with the inventive methods may be followed in commerce on the basis of their unique carbon isotope profile.

Bioproducts can be distinguished from petroleum-based organic compounds by comparing the stable carbon isotope ratio ($^{13}C/^{12}C$) in each fuel. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway.

The $^{13}C$ measurement scale was originally defined by a zero set by Pee Dee Belemnite (PDB) limestone, where values are given in parts per thousand deviations from this material. The "$\delta^{13}C$" values are expressed in parts per thousand (per mil), abbreviated, ‰, and are calculated as follows:

$$\delta^{13}C\%o) = [(^{13}C/^{12}C)_{sample} - (^{13}C/^{12}C)_{standard}]/(^{13}C/^{12}C)_{standard} \times 1000$$

In some embodiments, a bioproduct produced according to the methods of the invention has a $\delta^{13}C$ of about −30 or greater, about −28 or greater, about −27 or greater, about −20 or greater, about −18 or greater, about −15 or greater, about −13 or greater, or about −10 or greater. Alternatively, or in addition, a bioproduct has a $\delta^{13}C$ of about −4 or less, about −5 or less, about −8 or less, about −10 or less, about −13 or less, about −15 or less, about −18 or less, or about −20 or less. Thus, the bioproduct can have a $\delta^{13}C$ bounded by any two of the above endpoints. For example, the bioproduct can have a $\delta^{13}C$ of about −30 to about −15, about −27 to about −19, about −25 to about −21, about −15 to about −5, about −13 to about −7, or about −13 to about −10. In some embodiments, the bioproduct can have a $\delta^{13}C$ of about −10, −11, −12, or −12.3. In other embodiments, the bioproduct has a $\delta^{13}C$ of about −15.4 or greater. In yet other embodiments, the bioproduct has a $\delta^{13}C$ of about −15.4 to about −10.9, or a $\delta^{13}C$ of about −13.92 to about −13.84.

Bioproducts can also be distinguished from petroleum-based organic compounds by comparing the amount of $^{14}C$ in each compound. Because $^{14}C$ has a nuclear half life of 5730 years, petroleum based fuels containing "older" carbon can be distinguished from bioproducts which contain "newer" carbon (see, e.g., Currie, "Source Apportionment of Atmospheric Particles", *Characterization of Environmental Particles, J. Buffle and H. P. van Leeuwen, Eds., Vol. I of the IUPAC Environmental Analytical Chemistry Series, Lewis Publishers, Inc., pp.* 3-74 (1992)).

$^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C. As used herein, "fraction of modern carbon" or $f_M$ has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is approximately 1.1.

In some embodiments, a bioproduct produced according to the methods of the invention has a $f_M^{14}C$ of at least about 1, e.g., at least about 1.003, at least about 1.01, at least about 1.04, at least about 1.111, at least about 1.18, or at least about 1.124. Alternatively, or in addition, the bioproduct has an $f_M^{14}C$ of about 1.130 or less, e.g., about 1.124 or less, about 1.18 or less, about 1.111 or less, or about 1.04 or less. Thus, the bioproduct can have a $f_M^{14}C$ bounded by any two of the above endpoints. For example, the bioproduct can have a $f_M^{14}C$ of about 1.003 to about 1.124, a $f_M^{14}C$ of about 1.04 to about 1.18, or a $f_M^{14}C$ of about 1.111 to about 1.124.

Another measurement of $^{14}C$ is known as the percent of modern carbon, i.e., pMC. For an archaeologist or geologist using $^{14}C$ dates, AD 1950 equals "zero years old." This also represents 100 pMC. "Bomb carbon" in the atmosphere reached almost twice the normal level in 1963 at the peak of thermo-nuclear weapons testing. Its distribution within the atmosphere has been approximated since its appearance, showing values that are greater than 100 pMC for plants and animals living since AD 1950. *It has gradually decreased over time with today's value being near* 107.5 pMC. This means that a fresh biomass material, such as corn, would give a $^{14}C$ signature near 107.5 pMC. Petroleum-based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum-based products, the measured pMC value for that material will reflect the proportions of the two component types. For example, a material derived 100% from present day soybeans would have a radiocarbon signature near 107.5 pMC. If that material was diluted 50% with petroleum-based products, the resulting mixture would have a radiocarbon signature of approximately 54 pMC.

A biologically-based carbon content is derived by assigning "100%" equal to 107.5 pMC and "0%" equal to 0 pMC. For example, a sample measuring 99 pMC will provide an equivalent biologically-based carbon content of 93%. This value is referred to as the mean biologically-based carbon result and assumes that all of the components within the analyzed material originated either from present day biological material or petroleum-based material.

In some embodiments, a bioproduct produced according to the methods of the invention has a pMC of at least about 50, at least about 60, at least about 70, at least about 75, at least about 80, at least about 85, at least about 90, at least about 95, at least about 96, at least about 97, or at least about 98. Alternatively, or in addition, the bioproduct has a pMC of about 100 or less, about 99 or less, about 98 or less, about 96 or less, about 95 or less, about 90 or less, about 85 or less, or about 80 or less. Thus, the bioproduct can have a pMC bounded by any two of the above endpoints. For example, a bioproduct can have a pMC of about 50 to about 100; about 60 to about 100; about 70 to about 100; about 80 to about 100; about 85 to about 100; about 87 to about 98; or about 90 to about 95. In other embodiments, a bioproduct described herein has a pMC of about 90, about 91, about 92, about 93, about 94, or about 94.2.

The following examples further illustrate the invention but, of course, should not be construed as in any way limiting its scope.

EXAMPLE 1

This example demonstrates a method to identify engineered host cells which display enhanced production of fatty acids and derivatives thereof.

ALC310 is a previously characterized *E. coli* strain having the genotype MG1655 (ΔfadE::FRT ΔfhuA::FRT fabB [A329V] ΔentD::$P_{T5}$-entD) which carries the plasmid ALC310 (pCL1920_$P_{TRC}$_carBopt_13G04_alrA_sthA) (SEQ ID NO: 13) and produces fatty acids and derivatives thereof. To identify strains which display an improved titer or yield of fatty acids or derivatives thereof, transposon mutagenesis of ALC310 was performed followed by high-throughput screening.

The transposon DNA was prepared by cloning a DNA fragment into the plasmid EZ-Tn5™ pMOD™<R6K ori/MCS> (Epicentre Biotechnologies, Madison, Wis.). The DNA fragment contains a T5 promoter and a chloramphenicol resistance gene (cat) flanked by loxP sites. The resulting plasmid was named p100.38 (SEQ ID NO: 14). The p100.38 plasmid was optionally digested with PshAI restriction enzyme, incubated with EZ-Tn5™ Transposase enzyme (Epicentre Biotechnologies, Madison, Wis.), and electroporated into electrocompetent ALC310 cells as per the manufacturer's instructions. The resulting colonies contained the transposon DNA inserted randomly into the chromosome of ALC310.

Transposon clones were then subjected to high-throughput screening to measure production of fatty alcohols. Briefly, colonies were picked into deep-well plates containing Luria-Bertani (LB) medium. After overnight growth, each culture was inoculated into fresh LB. After 3 hours growth, each culture was inoculated into fresh FA-2 media. Spectinomycin (100 µg/mL) was included in all media to maintain selection of the 7P36 plasmid. FA-2 medium is M9 medium with 3% glucose supplemented with antibiotics, 10 µg/L iron citrate, 1 ytg/L thiamine, 0.1 M Bis-Tris buffer (pH 7.0), and a 1:1000 dilution of the trace mineral solution described in Table 1.

TABLE 1

Trace mineral solution
(filter sterilized)

2 g/L ZnCl·4H$_2$O
2 g/L CaCl$_2$·6H$_2$O
2 g/L Na$_2$MoO$_4$·2H$_2$O
1.9 g/L CuSO$_4$·5H$_2$O
0.5 g/L H$_3$BO$_3$
100 mL/L concentrated HCl
q.s. Milli-Q water After 20 hours growth in FA-2, the cultures were extracted with butyl acetate. The crude extract was derivatized with BSTFA (N,O-bis[Trimethylsilyl]trifluoroacetamide) and total fatty species (e.g., fatty alcohols, fatty aldehydes, and fatty acids) were measured with GC-FID as described in International Patent Application Publication WO 2008/119082.

Clones that produced 15% more total fatty species than ALC310 were subjected to further verification using a shake-flask fermentation. Briefly, the clones were grown in 2 mL of LB medium supplemented with spectinomycin (100 mg/L) at 37° C. After overnight growth, 100 µL of culture was transferred into 2 mL of fresh LB supplemented with antibiotics. After 3 hours growth, 2 mL of culture was transferred into a 125 mL-flask containing 18 mL of FA-2 medium supplemented with spectinomycin (100 mg/L). When the OD$_{600}$ of the culture reached 2.5, 1 mM of IPTG was added to each flask. After 20 hours of growth at 37° C., a 400 µL sample from each flask was removed, and total fatty species were extracted with 400 µL butyl acetate. The crude extracts were analyzed directly with GC-FID as described above.

Figure 2:
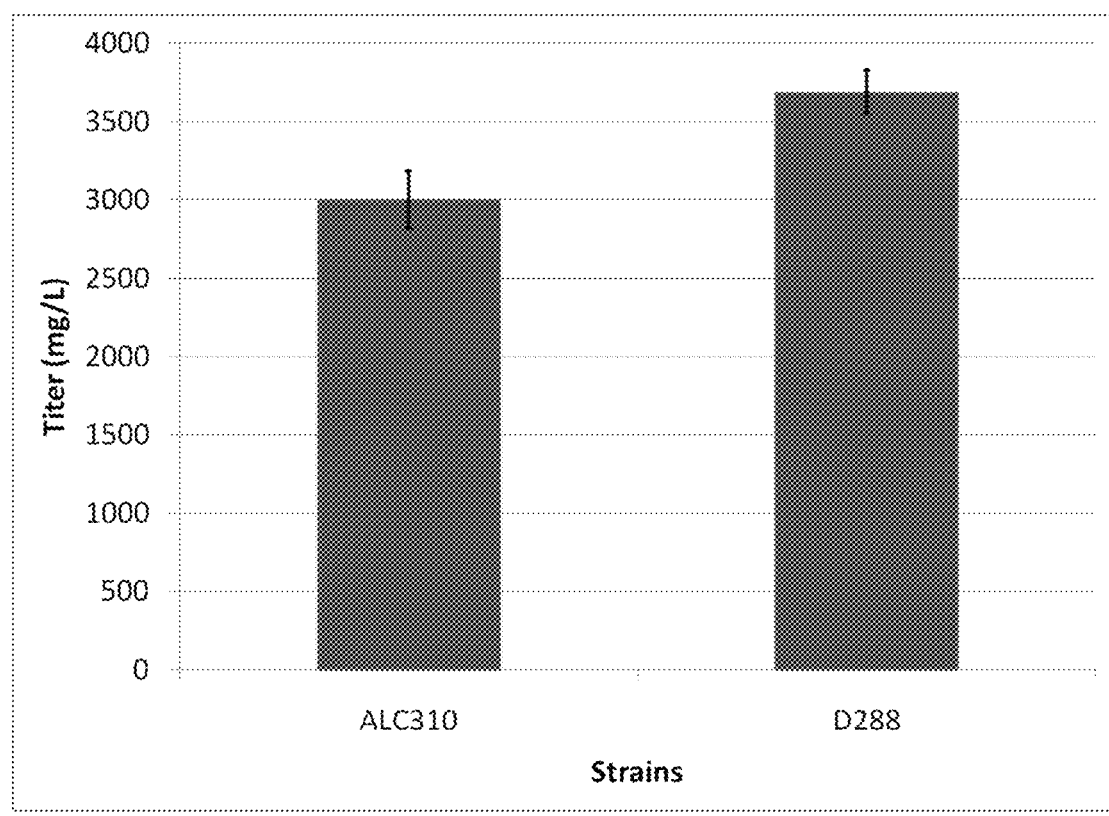
FIG. 2 is a graph of fatty species production in a control E. coli strain (ALC310) or the transposon insertion strain, D288.

A transposon clone (termed D288) was identified which displayed increased titers of total fatty species as compared to the parental ALC310 strain (FIG. 2).

The results of this example demonstrate a method to identify engineered host cells which display enhanced production of fatty acids and derivatives thereof as compared to a corresponding wild-type host cell.

EXAMPLE 2

This example demonstrates that an engineered host cell with a transposon insertion in the nhaB gene displays enhanced production of fatty acids and derivatives thereof as compared to a corresponding wild-type host cell.

Sequence analysis was performed to identify the location of the transposon insertion in the D288 strain identified in Example 1. To do so, genomic DNA was purified from a 3-mL overnight LB culture of D288 cells using the ZR Fungal/Bacterial DNA MiniPrep™ kit (Zymo Research) according to the manufacturer's instructions. The purified genomic DNA was sequenced outward from the transposon using the primers DG150 (GCAGTTATTGGTGCCCT-TAAACGCCTGGTTGCTACGCCTG) (SEQ ID NO: 15) and DG153 (CCCAGGGCTTCCCGGTAT-CAACAGGGACACCAGG) (SEQ ID NO: 16), internal to the transposon.

Figure 3:
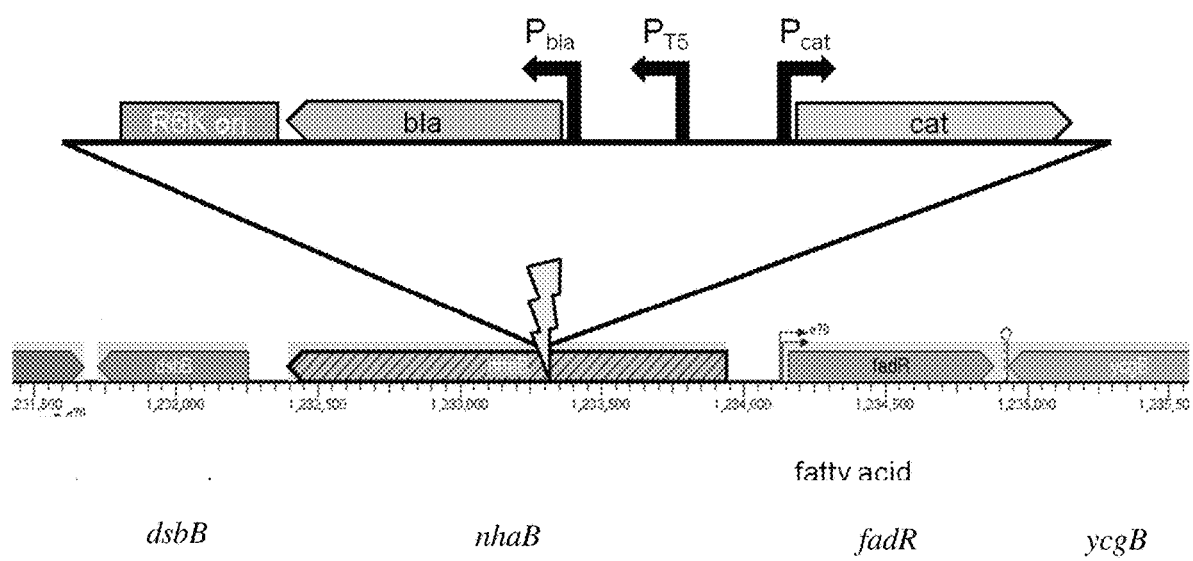
FIG. 3 is a diagram depicting the location of the transposon insertion in the D288 strain.

The D288 strain was determined to have a transposon insertion in the nhaB gene (FIG. 3).

The results of this example demonstrate an engineered *E. coli* host cell with a transposon insertion in the nhaB gene displays enhanced production of fatty acids and derivatives thereof as compared to a corresponding wild-type *E. coli* host cell.

EXAMPLE 3

This example demonstrates that engineered host cells having an altered level of production of FadR display enhanced production of fatty acids and derivatives thereof.

The nhaB gene is proximal to the gene encoding the fatty acid degradation regulator, FadR (FIG. 3). To determine if altering the expression of FadR affects the production of fatty acids or derivatives thereof in host cells, a FadR expression library was cloned and screened.

To clone the expression library, the wild-type fadR gene was amplified from genomic DNA of *E. coli* MG1655 by PCR using primers DG191 (SEQ ID NO: 17) and DG192 (SEQ ID NO: 18). A mutant fadR gene containing amino acid change S219N was also amplified from *E. coli* MG1655 fadR[S219N] genomic DNA using the DG191 and DG192 primer set. The primers used in this example are listed in Table 2.

TABLE 2

| Primer | Sequence | Sequence Identifier |
|---|---|---|
| DG191 | ATGGTCATTAAGGCGCAAAGCCCGG | SEQ ID NO: 17 |
| DG192 | GAGACCCCACACTACCATCCTCGAGTTATCG CCCCTGAATGGCTAAATCACCC | SEQ ID NO: 18 |
| SL03 | CTCGAGGATGGTAGTGTGGGGTCTCCC | SEQ ID NO: 19 |
| SL23 | GAGACCGTTTCTCGAATTTAAATATGATACG CTCGAGCTTCGTCTGTTTCTACTGGTATTGG CACAAAC | SEQ ID NO: 20 |
| DG193 | TGAAAGATTAAATTTNHHARNDDHDDNWAGGA GNNNNNNNATGGTCATTAAGGCGCAAAGCCCGG | SEQ ID NO: 21 |

A gene cassette encoding for kanamycin resistance (kan) was PCR amplified from plasmid pKD13 using primers SLO3 (SEQ ID NO: 19) and SL23 (SEQ ID NO: 20). Each fadR cassette (i.e., wild-type and S219N mutant) was separately joined with the kanamycin resistance cassette using splicing by overlap extension (SOE) PCR using primers SL23 and DG193 (SEQ ID NO: 21). The DG193 primer contained degenerate nucleotides for the generation of expression variants.

Plasmid p100.487 (pCL1920_P$_{TRC}$_carBopt_13G04_alrA_fabB[A329G]) (SEQ ID NO: 22) was linearized via restriction digestion with enzymes SwaI and XhoI. Each of the two SOE PCR fadR-kan products were separately cloned into linearized plasmid p100.487 using the INFUSION' system (Clontech, Mountain View, Calif.), and then the plasmids were transformed into chemically competent NEB TURBO' cells (New England Biolabs, Ipswich, Mass.). Transformants were plated on LB agar containing 50 µg/mL kanamycin.

Thousands of colonies were obtained for fadR and fadR [S219N]. Colonies were scraped from plates and the plasmids were isolated by miniprepping according to standard protocols. The resulting pool of plasmids was transformed into an *E. coli* EG149 strain having a genotype of MG1655 (ΔfadE::FRT ΔthuA::FRT fabB[A329V] ΔentD::P$_{T5}$-entD)), and selected on LB plates containing 100 µg/mL spectinomycin.

Figure 4:
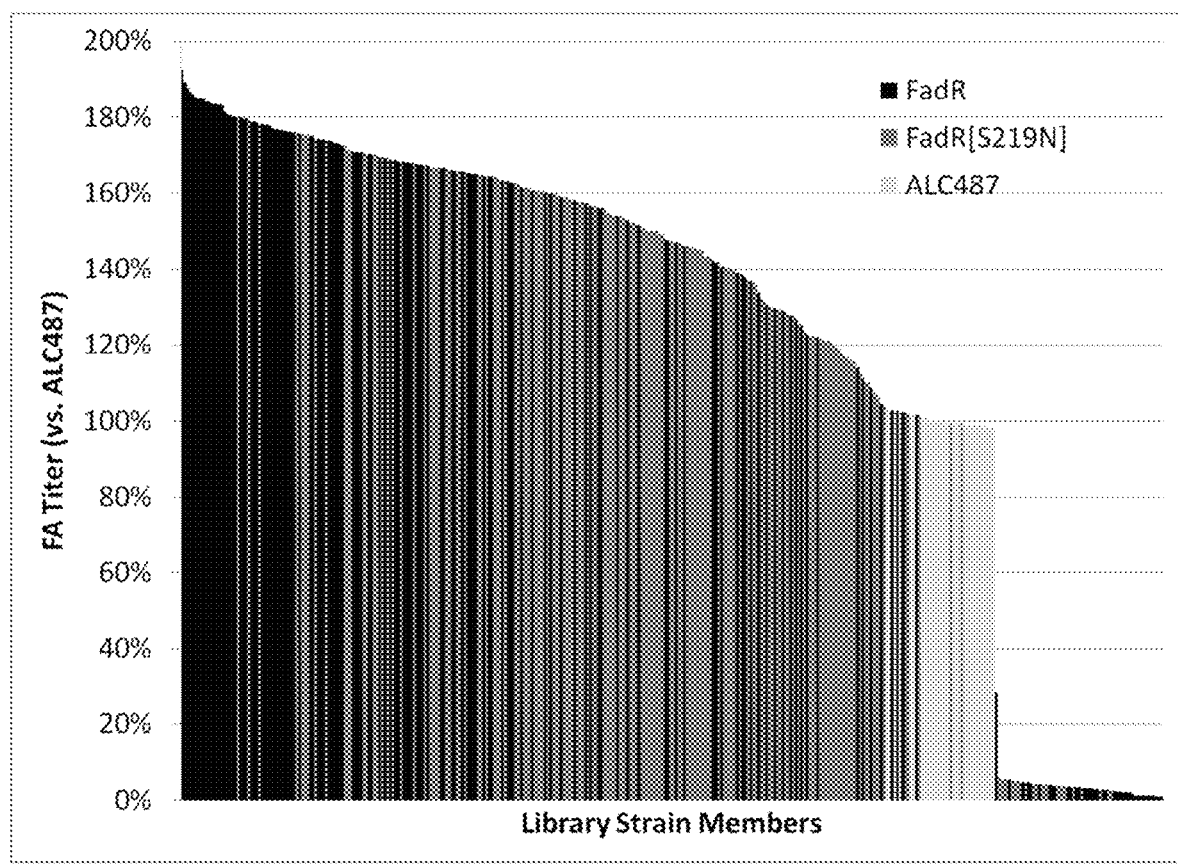
FIG. 4 is a bar graph of total fatty species (FA) titers in expression library E. coli strains having altered expression of wild-type FadR or mutant FadR[S219N] as compared to FA titers in the control E. coli strain (ALC487).

Transformants were then screened for production of total fatty species (e.g., fatty acids, fatty aldehydes, and fatty alcohols) using the deep-well procedure described in Example 1. Numerous strains were identified which displayed enhanced production of total fatty species as compared to the control ALC487 strain (EG149 strain carrying plasmid p100.487) (FIG. 4). Strains expressing either wild-type fadR or fadR [S219N] displayed enhanced production of total fatty species as compared to the ALC487 strain, although the highest titers were observed in strains expressing wild-type FadR (FIG. 4).

Figure 5:
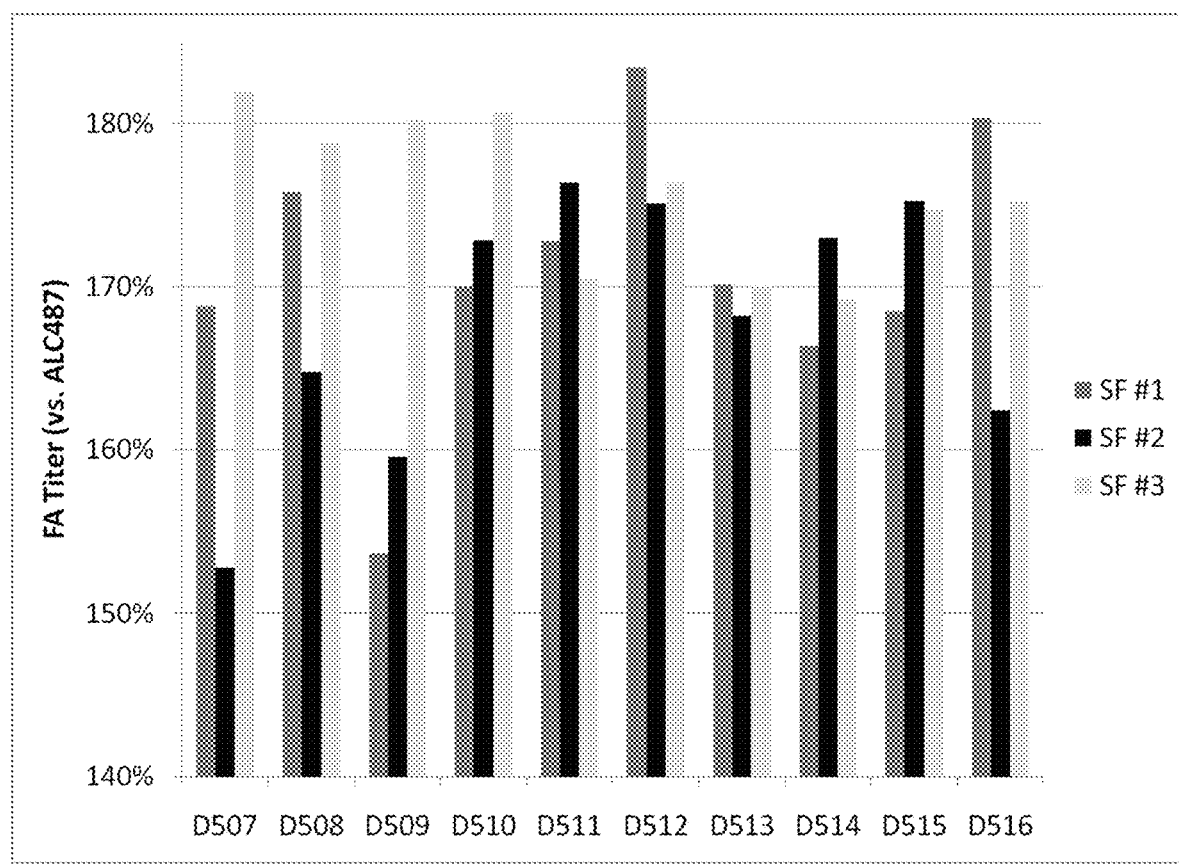
FIG. 5 is a bar graph of total fatty species (FA) titers in three separate shake flask (SF) fermentations of E. coli strain D512 having altered expression of wild-type FadR as compared to FA titers in the control ALC487 strain.

Several of the top producing strains expressing wild-type FadR identified in the initial screen were assigned strain IDs and validated in a shake flask fermentation. Briefly, each strain was streaked for single colonies, and three separate colonies from each strain were grown in three separate flasks according to the shake flask fermentation protocol described in Example 1. Total fatty species were measured using GC-FID as described in Example 1. All of the strains expressing wild-type FadR displayed higher total fatty species titers as compared to the control ALC487 strain (FIG. 5).

Figure 6:
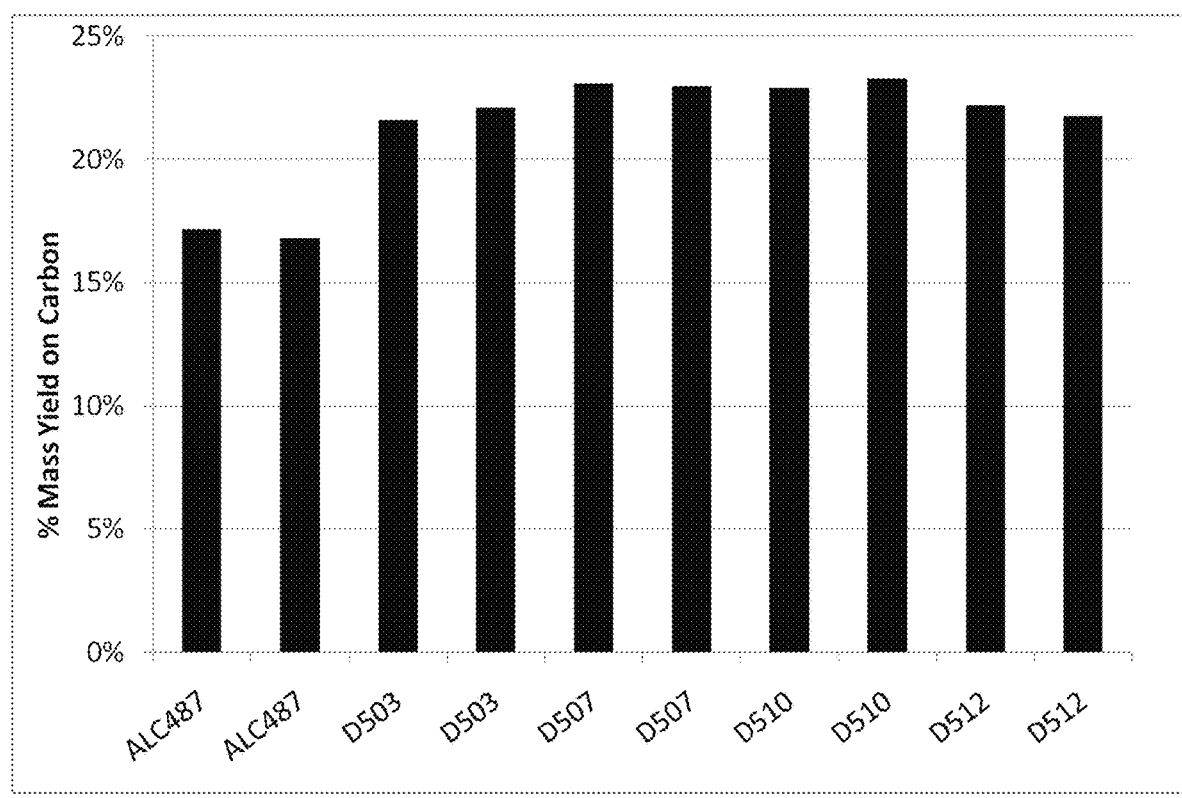
FIG. 6 is a bar graph of total fatty species yield on carbon in shake flask fermentations of the control ALC487 strain or E. coli strain D512 having altered expression of wild-type FadR.

Several of the top producing strains expressing wild-type FadR were then further characterized in order to determine the yield of fatty species. To do so, a shake flask fermentation was performed as described above, except that (i) the temperature was held at 32° C., (ii) additional glucose was added after 18 hours and 43 hours, and (iii) extraction was performed at 68.5 hours. The total fatty species produced was divided by the total glucose consumed to calculate the fatty species yield. All of the strains expressing wild-type FadR displayed a higher yield of total fatty species as compared to the control ALC487 strain (FIG. 6).

The D512 strain was then further characterized by evaluating total fatty species titer and yield following fermentation in a 5 L bioreactor. At a glucose feed rate of 10 g/L/hr glucose, the D512 strain produced higher titers of fatty acids and fatty alcohols as compared to the control ALC487 strain (FIG. 7). In addition, the total yield on all fatty species increased in the D512 strain as compared to the ALC487 strain (FIG. 7). At a higher glucose feed rate of 15 g/L/hr, the D512 strain produced approximately 68.5 g/L total fatty species at a yield of approximately 20% (FIG. 7). The D512 strain produced a higher total fatty species titer and yield at 15 g/L/hr as compared to 10 g/L/hr (FIG. 7).

Plasmid DNA was isolated from the D512 strain and sequenced according to standard protocols. The plasmid obtained from the D512 strain, termed pDG109, was determined to have the sequence corresponding to SEQ ID NO: 23.

The results of this example demonstrate that engineered host cells having an altered level of expression of FadR produce higher titers and yields of fatty acids and derivatives thereof as compared to corresponding wild-type host cells.

EXAMPLE 4

This example demonstrates a method to produce high titers of fatty acids in engineered host cells having an altered level of expression of FadR.

The *E. coli* EG149 strain utilized in Example 3 overexpresses the entD gene, which encodes a phosphopantetheine transferase (PPTase) involved in the activation of the CarB enzyme that catalyzes the reduction of fatty acids to fatty aldehydes and fatty alcohols.

To assess the effect of entD expression on fatty acid and fatty alcohol production in the D512 strain, a D512 variant was generated which contained a deletion of the entD gene (D512 ΔentD). Shake flask fermentations were performed with the D512 strain and the D512 ΔentD strain as described in Example 1. The D512 strain produced high titers of fatty alcohols and comparatively lower titers and yields of fatty acids (FIG. 7). In contrast, the D512 ΔentD strain produced high titers and yields of fatty acids, and relatively low titers of fatty alcohols (FIG. 8). The titers of total fatty species were similar between the D512 strain and the D512 ΔentD strain (FIG. 8).

The results of this example demonstrate that engineered host cells having an altered level of FadR expression produce high titers of fatty acids when the entD gene is deleted.

EXAMPLE 5

This example demonstrates a method to identify engineered host cells which display enhanced production of fatty acids and derivatives thereof.

To further assess the effect of altered FadR expression on the production of fatty acids and derivatives thereof, ribosome binding site (RBS) libraries of FadR (S219N) and wild-type FadR were prepared and screened in *E. coli* host cells.

An RBS library was inserted upstream of the fadR (S219N) gene in pDS57 as follows. The genomic DNA of a strain containing the fadR(S219N) allele Moniker stEP005; id: s26z7 was amplified by PCR using the DG191 (SEQ ID NO: 17) and fadR (S219N)_pme319rc (SEQ ID NO: 24) primer set. The primers used in this example are listed in Table 3.

TABLE 3

| Primer | Sequence | Sequence Identifier |
|---|---|---|
| DG191 | ATGGTCATTAAGGCGCAAAGCCCGG | SEQ ID NO: 17 |
| fadR (S219N)_pme 319rc | CAAAACAGCCAAGCTGGAGACCGT TTTTATCGCCCCTGAATGGCTAAA TCACC | SEQ ID NO: 24 |
| 377-rbs- fadR (S219N)f | GCCCGAACCCGCAAGTAANHHARND DHDDNWAGGARNNNNNNNATGGTCA TTAAGGCGCAAAGCCCGG | SEQ ID NO: 25 |
| NH246 | AAAAACGGTCTCCAGCTTGGCTGT TTTGGCGGATGAGAGAAGATTTTC | SEQ ID NO: 26 |
| 377-3r | TTACTTGCGGGTTCGGGCGC | SEQ ID NO: 27 |

After the fadR (S219N) template was made, the RBS was added by PCR using the 377-rbs-fadR (S219N)f (SEQ ID NO: 25) and fadR (S219N)-pme319rc (SEQ ID NO: 24) primer set. The 377-rbs-fadR (5219N)f primer contained degenerate nucleotides to introduce variability into the RBS library. The RBS-fadR (S219N) was ligated with a pDS57 vector backbone (described in Example 5), using the commercial available CLONEZ™ kit from Genscript (Piscataway, N.J.) with the NH246 (SEQ ID NO: 26) and 377-3r (SEQ ID NO: 27) primer set.

An RBS library also was inserted upstream of the wild-type fadR gene in pDS57 using s similar protocol, except that the wild-type fadR gene was amplified by PCR using *E. coli* DV2 genomic DNA.

The ligated pDS57-rbs-fadR (S219N) and pDS57-rbs-fadR constructs were transformed separately into an *E. coli* DAM1 strain by electroporation. Strain DAM1 was produced as a derivative of strain DV2 (MGI 655 ΔfadE, ΔfluA), where the lacI$^q$-T$_{rce}$-tesA-fadD genes were integrated into the chromosome using the Tn7-based delivery system present in plasmid pGRG25 (described in McKenzie et al., *BMC Microbiology* 6: 39 (2006)). After transformation, the cells were recovered for 1 hour at 37° C. followed by plating on LB agar containing spectinomycin. After overnight incubation at 37° C., single colonies were picked to screen in 96 deep well-plates containing 300 μL/well LB with spectinomycin. The plates were incubated in a 32° C. shaker with 80% humidity and shaking at 250 RPM for approximately 5 hours. After 5 hours of growth, 30 μL/well of LB culture was transferred to 300 μL/well FA2 (2 g/L nitrogen) medium containing spectinomycin. Plates were incubated again in a 32° C. shaker with 80% humidity and shaking at 250 RPM overnight. 30 μL/well of the overnight culture was inoculated into 300 μL/well FA2 (1 g/L nitrogen) medium containing spectinomycin, 1 mM IPTG, and 2% methanol. One replicate plate was incubated in 32° C. shaker and another was incubated in a 37° C. shaker with 80% humidity and shaking at 250 RPM overnight. The recipe for FA2 medium is listed in Table 4.

TABLE 4

| Reagent | mL Reagent per 1000 mL FA2 |
| --- | --- |
| 5X Salt Solution | 200 |
| Thiamine (10 mg/mL) | 0.1 |
| 1M MgSO$_4$ | 1 |
| 1M CaCl$_2$ | 0.1 |
| 50% glucose | 60 |
| TM2 (trace minerals no iron) | 1 |
| 10 g/L ferric citrate | 1 |
| 2M Bis-Tris buffer | 50 |
| NH$_4$Cl* | 10 |
| Water | q.s. to 1000 mL |

*eliminated for FA2 (1 g/L nitrogen) medium

After approximately 24 hours of incubation, the plates were extracted by adding 40 μL/well 1M HCl and 300 μL/well butyl acetate. The plates were shaken for 15 minutes at 2000 RPM, and then centrifuged for 10 minutes at 4500 RPM at room temperature. 50 μL of the organic layer per well was transferred to a shallow well 96-well plate containing 50 μL/well BSTFA (Sigma Aldrich, St. Louis, Mo.), and the extracts were analyzed by GC-FID.

Several clones of *E. coli* DAM1 transformed with pDS57-rbs-fadR were identified as producing substantially higher titers of FAMEs and free fatty acids as compared to control *E. coli* DAM1 transformed with pDS57 alone. In general, the FadR variants produced low C14 to C16 ratios and displayed overall higher titers at 32° C. as compared to 37° C.

Numerous clones of *E. coli* DAM1 transformed with pDS57-rbs-FadR(S219N) also were identified as producing substantially higher titers of FAMEs and free fatty acids as compared to control *E. coli* DV2 or *E. coli* DANE transformed with pDS57 alone.

Two of the clones transformed with pDS57-rbs-FadR (S219N) identified in the initial screen (designated as P1A4 and P1G7) were further characterized in shake flask fermentations. Briefly, each colony was inoculated into 5 mL of LB containing spectinomycin and incubated at 37° C. with shaking at approximately 200 RPM for about 5 hours. 1.5 mL of the LB culture was transferred into 13.5 mL FA2 (2 g/L nitrogen) medium containing 0.05% Triton X-100 and spectinomycin in a 125 mL baffled flask. The flask cultures were incubated overnight at 32° C., 80% humidity and 250 RPM. 1.5 mL of the overnight culture was transferred into a new 125 mL baffled flask that contained 13.5 mL FA2 (1 g/L nitrogen) medium containing 0.05% Triton X-100, 1 mM IPTG, 2% methanol, and spectinomycin. The flask cultures were then incubated at 32° C., 80% humidity and 250 RPM. After 56 hours of incubation, 500 μL samples were taken out from each flask. 100 μL of each sample was diluted with 900 μL water to measure the OD of the culture, 100 μL of each sample was diluted with 900 μL water to measure remaining glucose, and 300 μL of each sample was extracted and analyzed using GC-FID as described above.

Both of the two FadR variants (i.e., P1A4 and P1G7) produced higher titers and yields of total fatty species as compared to the control strain transformed with pDS57 alone in the shake flask fermentation (FIG. 9).

Production of fatty species by PIA4 and P1G7 was also measured in large scale fermentations. To do so, cells from a frozen stock were grown in LB media for a few hours and then transferred to a defined media consisting of 3 g/L KH$_2$PO4, 6 g/L Na$_2$HPO4 dihydrate, 2 g/L NH$_4$Cl, 0.24 g/L MgSO4×7 H$_2$O, 20 g/L glucose, 200 mM Bis-Tris buffer (pH 7.2), 1.0 ml/L trace metals solution, and 1.0 mg/L thiamine, and cultured overnight. The trace metals solution was composed of 27 g/L FeCl$_3$×6 H2O, 2 g/L ZnCl2×4H$_2$O, 2 g/L CaCl$_2$×6 H$_2$O, 2 g/L Na$_2$MoO$_4$×2H$_2$O, 1.9 g/L CuSO$_4$×5 H$_2$O, 0.5 g/L H$_3$BO$_3$, and 40 mL/L of concentrated HCl.

50 mL of each overnight culture was inoculated into 1 liter of production medium in a fermentor with temperature, pH, agitation, aeration and dissolved oxygen control. The medium composition was as follows: 1 g/L KH$_2$PO4, 0.5 g/L (NH4)$_2$SO$_4$, 0.5 g/L MgSO4×7 H$_2$O, 5 g/L Bacto casaminoacids, 0.034 g/L ferric citrate, 0.12 ml/L 1M HCl, 0.02 g/L ZnCl2×4 H2O, 0.02 g/L CaCl9×2H$_2$O, 0.02 g/L Na$_2$MoO$_4$×2H$_2$O, 0.019 g/L CuSO$_4$×5 H$_2$O, 0.005 g/L H$_3$BO$_3$ and 1.25 mL/L of a vitamin solution. The vitamin solution contained 0.06 g/L *riboflavina*, 5.40 g/L pantothenic acid, 6.0 g/L niacine, 1.4 g/L piridoxine and 0.01 g/L folic acid.

The fermentations were performed at 32° C., pH 6.8, and dissolved oxygen (DO) equal to 25% of saturation. pH was maintained by addition of NH$_4$OH, which also served as nitrogen source for cell growth. When the initial 5 g/L of glucose had been almost consumed, a feed consisting of 500 g/L glucose, 1.6 g/L of KH$_2$PO$_4$, 3.9 g/L MgSO$_4$.7H$_2$O, 0.13 g/L ferric citrate, and 30 ml/L of methanol was supplied to the fermentor.

In the early phase of growth, the production of FAME was induced by the addition of 1 mM IPTG and 20 ml/L of pure methanol. After most of the cell growth was completed, the feed rate was maintained at a rate of 7.5 g glucose/L/hour. After induction, methanol was continuously supplied with the glucose feed. The fermentation was continued for a period of 3 days, and samples were taken at several timepoints for analysis of fatty species as described above.

P1A4 and P1G7 produced higher titers of total fatty species (FAMEs and free fatty acids) as compared to the control strain transformed with pDS57 alone in the large scale fermentations (FIG. 10). In addition, P1A4 and P1G7 produced higher yields of total fatty species as compared to the control strain in the large scale fermentations (FIG. 11).

The results of this example demonstrate methods to produce engineered host cells having altered FadR expression which display enhanced titers and yields of FAMEs and fatty acids as compared to corresponding wild-type cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing a fatty acid, fatty acid ester, fatty aldehyde or a fatty alcohol, the method comprising:
(a) providing a host cell which is genetically engineered to have an increased level of expression of FadR polypeptide comprising the amino acid sequence of SEQ ID NO:1, optionally comprising a mutation at the amino acid residue serine 219 of SEQ ID NO:1 which is substituted by asparagine, compared to corresponding wild-type host cell, wherein the engineered host cell is a bacterial cell,
(b) culturing the engineered host cell in a culture medium comprising a carbohydrate carbon source under conditions permissive for the production of the fatty acid, fatty acid ester, fatty aldehyde or the fatty alcohol, and
(c) isolating the fatty acid, fatty acid ester, fatty aldehyde or the fatty alcohol, from the engineered host cell, wherein the engineered host cell produces 15% or more total fatty acid species compared to corresponding wild-type host cell under the same cultivation condition, wherein the fatty acid species are the fatty acid, fatty acid ester, fatty aldehyde and/or fatty alcohol.

2. The method of claim 1, wherein the FadR polypeptide comprises the mutation which is a substitution of the amino acid 219 of SEQ D NO:1 with an asparagine residue.

3. The method of claim 1, wherein the expression level of the FadR polypeptide in the engineered host cell is regulated by an exogenous element comprising an expression control sequence operably linked to the gene encoding the FadR polypeptide in said genetically engineered host cell.

4. The method of claim 3, wherein the expression control sequence is a promoter.

5. The method of claim 3, wherein the expression control sequence is a ribosome binding site.

6. The method of claim 1, wherein the engineered host cell further comprises an altered level of expression of one or more gene selected from the group consisting of fabA, fabB, iclR, fadA, fadB, fadD, fadE, fadI, fadJ, fadL, fadM, uspA, aceA, aceB, and aceK as compared to the level of expression of the selected gene in a corresponding wild-type host cell.

7. The method of claim 1, wherein the fatty acid ester is a fatty acid methyl ester (FAME) or a fatty acid ethyl ester (FAEE).

8. The method of claim 1, wherein an ester synthase is expressed in the engineered host cell at a greater concentration than is normally expressed in a corresponding wild-type cell under the same conditions.

9. The method of claim 8, wherein the ester synthase is ES9 from *Marinobacter hydrocarbonoclasticus* (SEQ ID NO: 2), ES8 from *Marinobacter hydrocarbonoclasticus* (SEQ ID NO: 3), AtfA1 from *Alcanivorax borkumensis* SK2 (SEQ ID NO: 4), AtfA2 from *Alcanivorax borkumensis* SK2 (SEQ ID NO: 5), diacylglycerol O-acyltransferase from *Marinobacter aquaeolei* VT8 (SEQ ID NO: 6 or SEQ ID NO: 7), a wax synthase, or a bifunctional wax ester synthase/acyl-CoA:diacylglycerol acyltransferase (wax-dgaT).

10. The method of claim 1, wherein an acetyl-CoA carboxylase complex is overexpressed in the engineered host cell.

11. The method of claim 10, wherein the acetyl-CoA carboxylase complex is encoded by two or more acetyl-CoA carboxylase subunit genes obtained from one or more of *Corynebacterium glutamicum, Escherichia coli, Lactococcus lactis, Kineococcus radiotolerans, Desulfovibrio desul-*

*furicans, Erwinia amylovora, Rhodospirillum rubrum, Vibrio furnissii, Stenotrophomonas maltophilia, Synechocystis* sp. PCC6803, or *Synechococcus elongatus*.

12. The method of claim 10, wherein a biotin protein ligase is overexpressed in the engineered host cell.

13. The method of claim 1, wherein a carboxylic acid reductase and a thioesterase are overexpressed in the engineered host cell.

14. The method of claim 13, wherein an alcohol dehydrogenase 1s overexpressed in the engineered host cell.

15. The method of claim 14, wherein the carboxylic acid reductase is carB (SEQ ID NO: 8), the thioesterase is tesA (SEQ ID NO: 11) and the alcohol dehydrogenase is YjgB (SEQ ID NO: 10) or AlrAadpl (SEQ ID NO: 9).

16. The method of claim 15, wherein a phosphopantheteinyl transferase (PPTase) is overexpressed in the engineered host cell.

17. The method of claim 16, wherein the PPTase is EntD from *E. coli* MG1655 (SEQ ID NO: 12).

18. The method of claim 1, wherein the bacterial cell is selected from the group consisting of an *E. coli* cell, a *Bacillus lentus* cell, a *Bacillus brevis* cell, a *Bacillus stearothermophilus* cell, a *Bacillus* lichen formis cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, and a *Bacillus amyloliquefaciens* cell.

19. A fatty alcohol produced by the method of claim 1 which is a C6, C8, C10, C12, C13, C14, C15, C16, C17, or C18 fatty alcohol.

20. The fatty alcohol of claim 19, wherein the fatty alcohol is a C10:1, C2:1, C4:1, C6:1, or C8:1 unsaturated fatty alcohol.

21. A surfactant composition comprising the fatty alcohol of claim 19.

* * * * *